(12) United States Patent
Barres et al.

(10) Patent No.: US 10,240,156 B2
(45) Date of Patent: *Mar. 26, 2019

(54) MODULATION OF SYNAPTIC MAINTENANCE

(71) Applicant: The Board of Trustees of the Leland Stanford Junior University, Stanford, CA (US)

(72) Inventors: Ben A. Barres, Palo Alto, CA (US); Alexander H. Stephan, Stanford, CA (US); Beth A. Stevens, Milton, MA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 49 days.

This patent is subject to a terminal disclaimer.

(21) Appl. No.: 15/222,603

(22) Filed: Jul. 28, 2016

(65) Prior Publication Data

US 2016/0326534 A1 Nov. 10, 2016

Related U.S. Application Data

(63) Continuation of application No. 13/586,556, filed on Aug. 15, 2012, now Pat. No. 9,480,658, which is a continuation-in-part of application No. 13/326,180, filed on Dec. 14, 2011, now Pat. No. 9,149,444, which is a continuation of application No. 11/636,001, filed on Dec. 8, 2006, now Pat. No. 8,148,330.

(60) Provisional application No. 61/523,702, filed on Aug. 15, 2011, provisional application No. 60/749,071, filed on Dec. 9, 2005.

(51) Int. Cl.
| | | |
|---|---|---|
| C12N 15/113 | (2010.01) | |
| A61K 31/00 | (2006.01) | |
| A61K 31/727 | (2006.01) | |
| A61K 45/06 | (2006.01) | |
| G01N 33/50 | (2006.01) | |
| G01N 33/564 | (2006.01) | |
| G01N 33/68 | (2006.01) | |
| A61K 38/17 | (2006.01) | |
| A61K 38/48 | (2006.01) | |
| A61K 31/7088 | (2006.01) | |
| A61K 48/00 | (2006.01) | |

(52) U.S. Cl.
CPC .......... *C12N 15/1138* (2013.01); *A61K 31/00* (2013.01); *A61K 31/7088* (2013.01); *A61K 31/727* (2013.01); *A61K 38/177* (2013.01); *A61K 38/1774* (2013.01); *A61K 38/482* (2013.01); *A61K 45/06* (2013.01); *G01N 33/5058* (2013.01); *G01N 33/564* (2013.01); *G01N 33/6872* (2013.01); *G01N 33/6896* (2013.01); *A61K 48/00* (2013.01); *C12N 2310/11* (2013.01); *C12N 2310/14* (2013.01); *C12N 2320/30* (2013.01); *G01N 2333/4716* (2013.01); *G01N 2500/04* (2013.01); *G01N 2800/28* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 8,148,330 B2 | 4/2012 | Barres et al. | |
| 9,149,444 B2 | 10/2015 | Barres et al. | |
| 9,382,313 B2 * | 7/2016 | Barres .................... | A61K 31/00 |
| 9,382,314 B2 * | 7/2016 | Barres .................... | A61K 31/00 |
| 9,388,238 B2 | 7/2016 | Barres et al. | |
| 9,480,658 B2 * | 11/2016 | Barres .................... | A61K 31/00 |
| 9,493,555 B2 | 11/2016 | Barres et al. | |
| 2002/0066117 A1 | 5/2002 | Nilsson et al. | |
| 2002/0104104 A1 | 8/2002 | Games et al. | |
| 2005/0241008 A1 | 10/2005 | Bredesen et al. | |
| 2012/0195880 A1 | 8/2012 | Barres et al. | |
| 2012/0328601 A1 | 12/2012 | Barres et al. | |
| 2015/0368324 A1 | 12/2015 | Barres et al. | |
| 2015/0368325 A1 | 12/2015 | Barres et al. | |
| 2015/0368326 A1 | 12/2015 | Barres et al. | |
| 2017/0059559 A1 | 3/2017 | Barres et al. | |

FOREIGN PATENT DOCUMENTS

| | | | |
|---|---|---|---|
| WO | WO 2014/186599 A2 | 11/2014 | |
| WO | WO 2015/006507 A1 | 1/2015 | |

OTHER PUBLICATIONS http://www.lifeextension.com/Protocols/Neurological/Age-Related-Cognitive-Decline/Page-03 (Year: 2018).*
https://www.healthandwellnessalerts.berkeley.edu/alerts/memory/Warning-Signs-of-Mild- . . . (Year: 2018).*
Salthouse, Neurobiol Aging., Apr. 2009; 30(4): 507-514 (Year: 2009).*

(Continued)

*Primary Examiner* — Satyanarayana R Gudibande

(74) *Attorney, Agent, or Firm* — Wolf, Greenfield & Sacks, P.C.

(57) ABSTRACT

C1q is shown to be expressed in neurons, where it acts as a signal for synapse elimination. Methods are provided for protecting or treating an individual suffering from adverse effects of synapse loss. These findings have broad implications for a variety of clinical conditions, including treating and preventing neurodegenerative diseases such as Alzheimer's disease.

21 Claims, 56 Drawing Sheets
(31 of 56 Drawing Sheet(s) Filed in Color)
Specification includes a Sequence Listing.

(56) References Cited

OTHER PUBLICATIONS

International Search Report and Written Opinion, dated Mar. 18, 2008, in connection with PCT/US2006/046857.

International Preliminary Report on Patentability, dated Mar. 24, 2009, in connection with PCT/US2006/046857.

[No Author Listed] Alzheimer's Disease Education and Referral Center. 2015. Retrieved from https://www.nia.nih.gov I alzheimers/ publication/ alzheimers-disease-fact-sheet on Nov. 13, 2015.

[No Author Listed] Amyotrophic Lateral Sclerosis (ALS) Fact Sheet. 2015. National Institute Neurological Disorders Stroke. Retrieved from http://www.ninds. nih. gov /disorders/ am yo trophiclateralsclerosis/ detail_ALS .htm on Nov. 15, 2015.

[No Author Listed] Amyotropohic lateral sclerosis. Mayo Clinic. Apr. 2014. Retrieved from http://www.mayoclinic.org/ diseases-conditions/amyotrophic-lateral-sclerosis/basics/treatment/con-20024 3Cf7 on Nov. 15, 2015.

[No Author Listed] Huntington's disease. Diseases conditions. Mayo clinic. Jul. 24, 2014. Retrieved from http://www.mayoclinic.org/ diseases-conditions/huntingtons-disease/basics/treatment/con-20030685 on Nov. 18, 2015.

[No Author Listed] Treatments for Alzheimer's disease. Alzheimer's association. Retrieved from http://www.alz.org/alzheimers disease_ treatments. asp on Nov. 13, 2015.

Campochiaro et al., Adenoviral vector-delivered pigment epithelium-derived factor for neovascular age-related macular degeneration: results of a phase I clinical trial. Hum Gene Ther. Feb. 2006;17(2):167-76.

Choi et al., Expression of Complement Regulator Genes in $A\beta_{1-42}$ Stimulated Human Neuroblastoma Cell. J Korean Neurol Assoc. Oct. 2003;21:513-20.

Christopherson et al., Thrombospondins are astrocyte-secreted proteins that promote CNS synaptogenesis. Cell. Feb. 11, 2005;120(3):421-33.

Cockett, Crib (NGF delivery) Cyto Therapeutics Inc. IDrugs. Jul. 1998;1(3):362-7. Abstract only.

Coleman et al., Synaptic slaughter in Alzheimer's disease. Neurobiol Aging. Dec. 2003;24(8):1023-7. Review. Abstract only.

Fonseca et al., Absence of C1q Leads to Less Neuropathology in Transgenic Mouse Models of Alzheimer's Disease. J Neurosci. 2004;24(29):6457-65.

Fu et al., Synaptic degeneration of retinal ganglion cells in a rat ocular hypertension glaucoma model. Cell Mol Neurobiol. Jun. 2009;29(4):575-81. doi: 10.1007/s10571-009-9349-7. Epub Jan. 27, 2009. Abstract only.

Galvan et al., Deficiency in complement C1q improves histological and functional locomotor outcome after spinal cord injury. J Neurosci. Dec. 17, 2008;28(51):13876-88. doi: 10.1523/JNEUROSCI.2823-08.2008.

Gupta et al., Glaucoma as a neurodegenerative disease. Curr Opin Ophthalmol. Mar. 2007;18(2):110-4. Review. Abstract only.

Hirai et al., Cbln1 is essential for synaptic integrity and plasticity in the cerebellum. Nat Neurosci. Nov. 2005;8(11):1534-41. Epub Oct. 23, 2005.

Jacobs et al., Immunoglobulins inhibit pathophysiological effects of anti-GQ1b-positive sera at motor nerve terminals through inhibition of antibody binding. Brain. Oct. 2003;126(Pt 10):2220-34. Epub Jul. 22, 2003.

Johnson et al., Perforant Path Transection Induces Complement C9 Deposition in Hippocampus. Exp Neurol. 1996;138:198-205.

Kaplitt et al., Safety and tolerability of gene therapy with an adeno-associated virus (AAV) borne GAD gene for Parkinson's disease: an open label, phase I trial. Lancet. Jun. 23, 2007;369(9579):2097-105. Abstract only.

Kumar et al., Transvascular delivery of small interfering RNA to the central nervous system. Nature. Jul. 5, 2007;448(7149):39-43.

Loos et al., Immunofluorescence studies on the subcomponents of the first component of complement (C1): detection of C1q and C1s in different cells of biopsy material and on human as well as on guinea pig peritoneal macrophages. Immunobiology. 1981;158(3):213-24.

Masliah et al., Synaptic and neuritic alterations during the progression of Alzheimer's disease. Neurosci Lett. Jun. 6, 1994;174(1):67-72. Abstract only.

McGeer et al., The future use of complement inhibitors for the treatment of neurological diseases. Drugs. Jun. 1998;55(6):739-46.

Morgan et al., The role of complement in disorders of the nervous system. Immunopharmacology. Dec. 1997;38(1-2):43-50.

Naito et al., Complement C1q activates canonical Wnt signaling and promotes aging-related phenotypes. Cell. Jun. 8, 2012;149(6):1298-313. doi: 10.1016/j.cell.2012.03.047. Erratum in: Cell. Aug. 3, 2012;150(3):659-60.

O'Reilly et al., RNA interference-mediated suppression and replacement of human rhodopsin in vivo. Am J Hum Genet. Jul. 2007;81(1):127-35.

O'Kusky et al., Neuronal degeneration in the basal ganglia and loss of pallido-subthalamic synapses in mice with targeted disruption of the Huntington's disease gene. Brain Res. Feb. 13, 1999;818(2):468-79.

Pfrieger et al., Synaptic efficacy enhanced by glial cells in vitro. Science. Sep. 12, 1997;277(5332):1684-7.

Raisler et al., Adeno-associated virus type-2 expression of pigmented epithelium-derived factor or Kringles 1-3 of angiostatin reduce retinal neovascularization. Proc Natl Acad Sci U S A. Jun. 25, 2002;99(13):8909-14.

Reich et al., Small interfering RNA (siRNA) targeting VEGF effectively inhibits ocular neovascularization in a mouse model. Mol Vis. May 30, 2003;9:210-6.

Ricklin et al., Complement-targeted therapeutics. Nat Biotechnol. Nov. 2007;25(11):1265-75.

Roos et al., Specific inhibition of the classical complement pathway by C1q-binding peptides. J Immunol. Dec. 15, 2001;167(12):7052-9.

Sahu et al., Complement inhibitors: a resurgent concept in anti-inflammatory therapeutics. Immunopharm. 2000;49:133-48. Review.

Spencer et al., Targeted delivery of proteins across the blood-brain barrier. Proc Natl Acad Sci U S A. May 1, 2007;104(18):7594-9.

Stasi et al., Complement Component 1Q (C1Q) Upregulation in Retina of Murine, Primate, and Human Glaucomatous Eyes. Invest Ophthalmol Vis Sci. Mar. 2006;47(3):1024-9. doi:10.1167/iovs.05-0830.

Stevens et al., The Classical Complement Cascade Mediates CNS Synapse Elimination. Cell. Dec. 14, 2007;131(6):1164-78. doi: 10.1016/j.cell.2007.10.036.

Tao et al., Encapsulated cell-based delivery of CNTF reduces photoreceptor degeneration in animal models of retinitis pigmentosa. Invest Ophthalmol Vis Sci. Oct. 2002;43(10):3292-8.

Terry et al., Physical basis of cognitive alterations in Alzheimer's disease: synapse loss is the major correlate of cognitive impairment. Ann Neurol. Oct. 1991;30(4):572-80. Abstract only.

Ullian et al., Control of synapse number of glia. Science. Jan. 26, 2001;291(5504):657-61.

Ullian et al., Schwann cells and astrocytes induce synapse formation by spinal motor neurons in culture. Mol Cell Neurosci. Feb. 2004;25(2):241-51.

Veerhuis et al., Complement C1-inhibitor expression in Alzheimer's disease. Acta Neuropathol. 1998;96:287-96.

Wishart et al., Synaptic vulnerability in neurodegenerative disease. J Neuropathol Exp Neurol. Aug. 2006;65(8):733-9.

Woodruff et al., Role of complement in motor neuron disease: animal models and therapeutic potential of complement inhibitors. Adv Exp Med Biol. 2008;632:143-58.

Yasojima et al., Complement regulators C1 inhibitor and CD59 do not significantly inhibit complement activation in Alzheimer disease. Brain Res. 1999;833:297-301.

\* cited by examiner

Figure 1
A
|  | Signal level | | Signal level | | Fold-change |
|---|---|---|---|---|---|
|  | -Astros | | +Astros | |  |
| C1qA | 213.4 | A | 823.8 | P | 4.2 |
| C1qB | -109 | A | 1309.5 | P | ~26.9 |
| C1qB | -72.9 | A | 512.9 | P | ~11.0 |
| C1qC | -135.8 | A | 614.8 | P | ~16.6 |
B
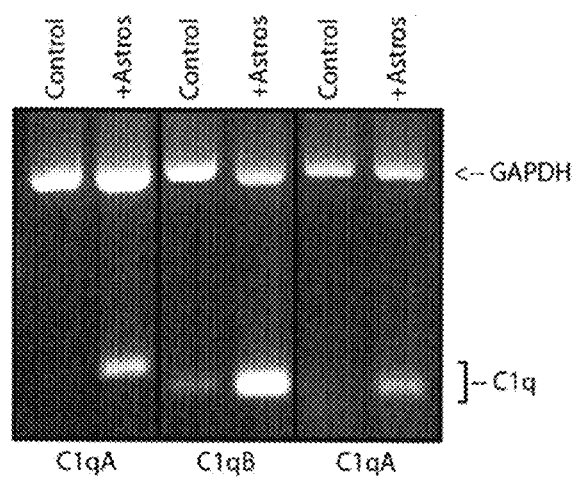
C
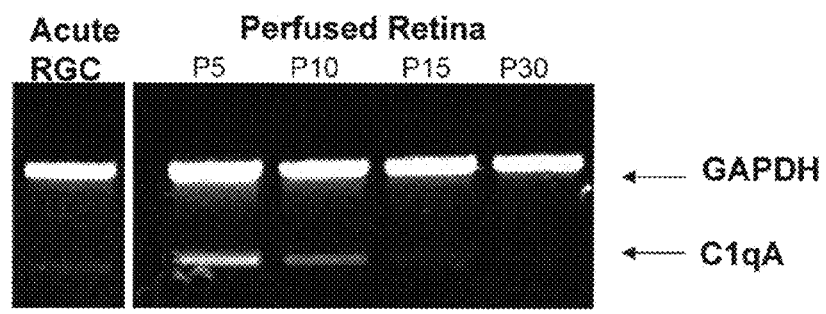

Figure 3
A
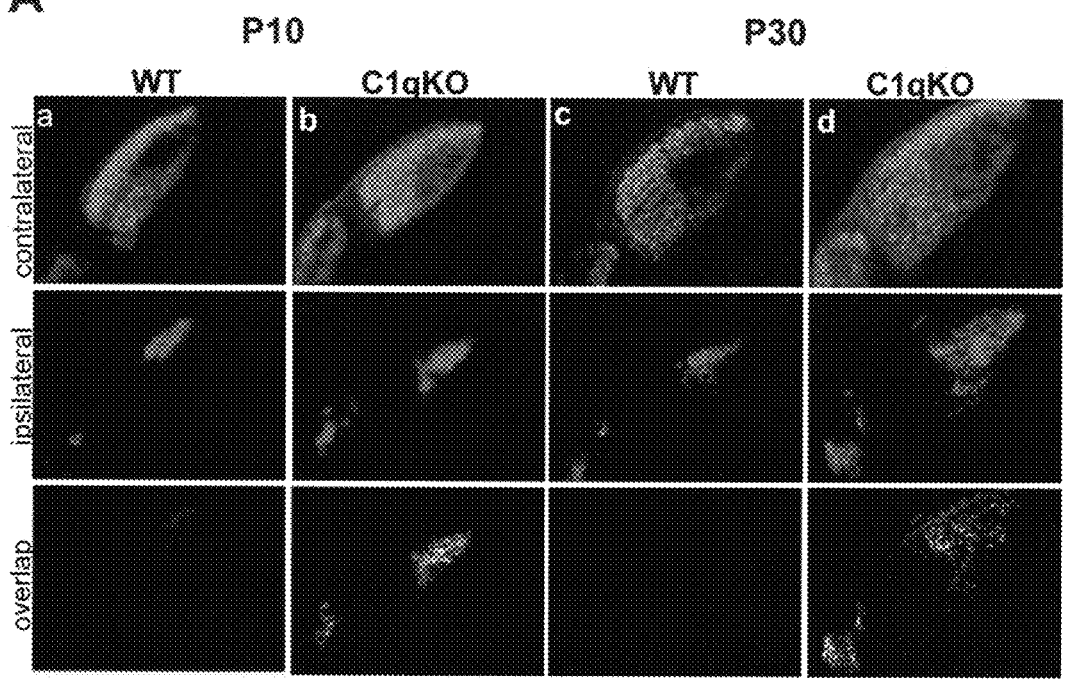
B 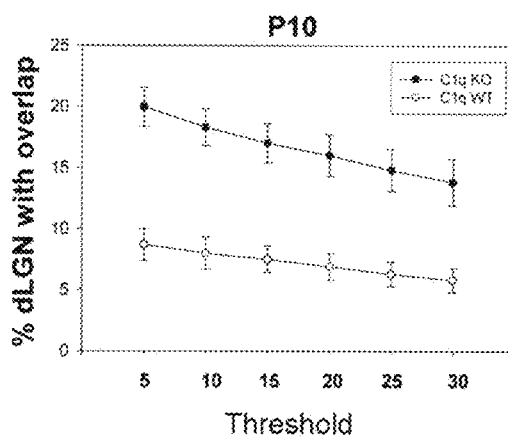
C 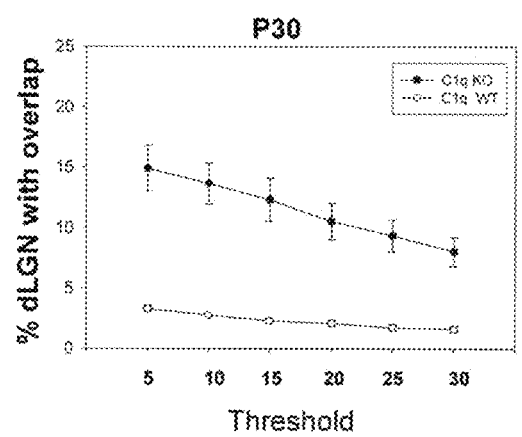

Figure 6
A.
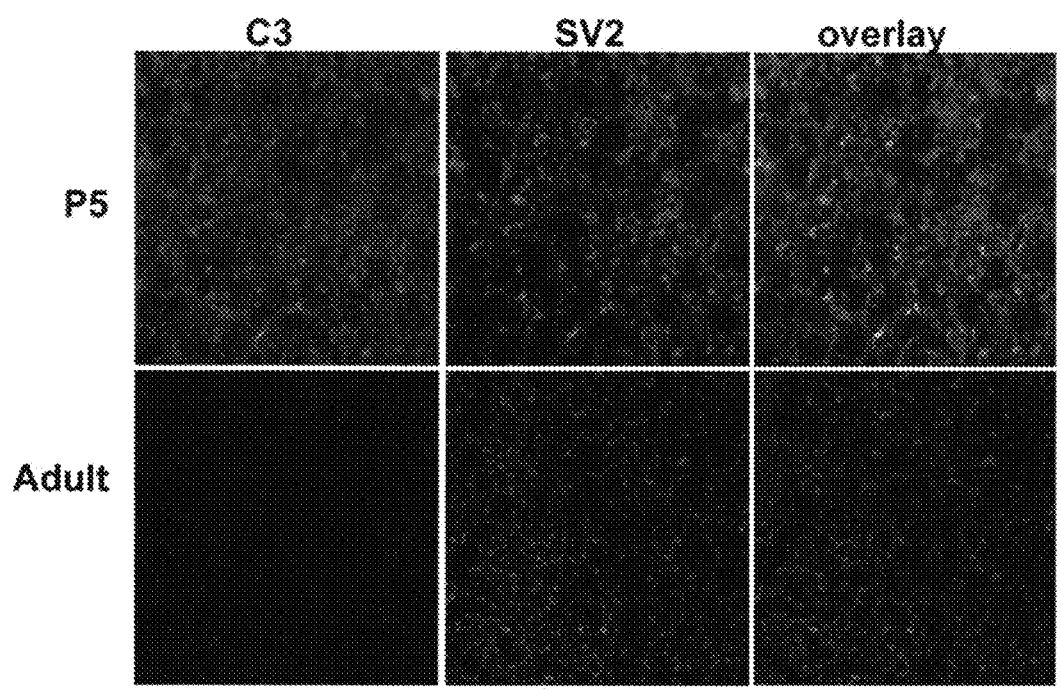
B.
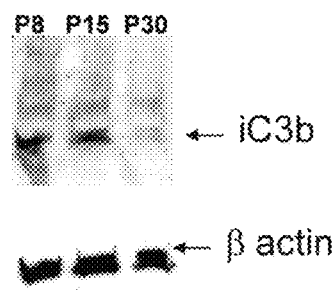

Figure 7
A
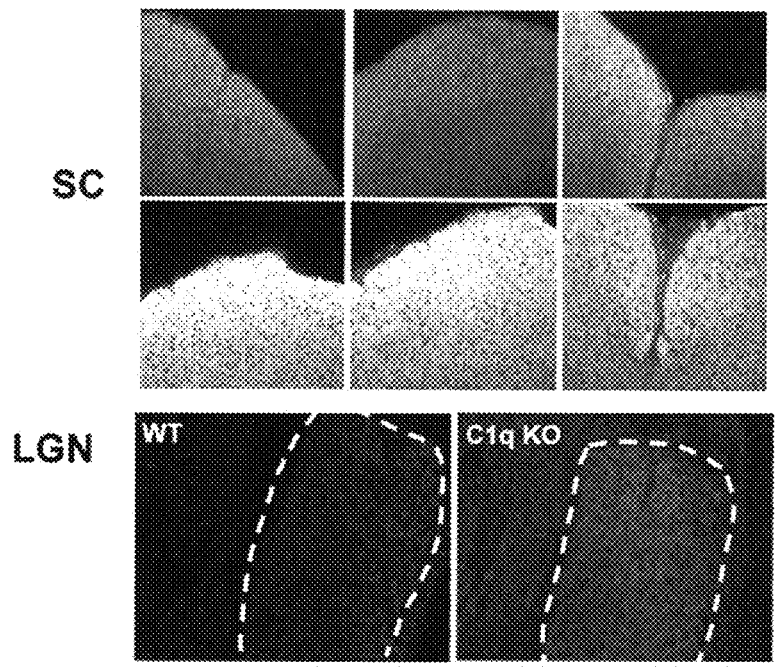
SC
LGN
B
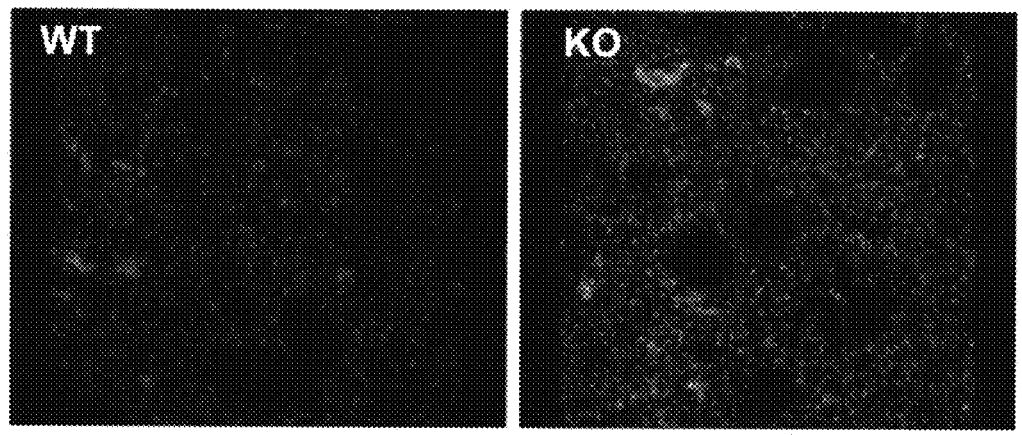

Figure 9
A
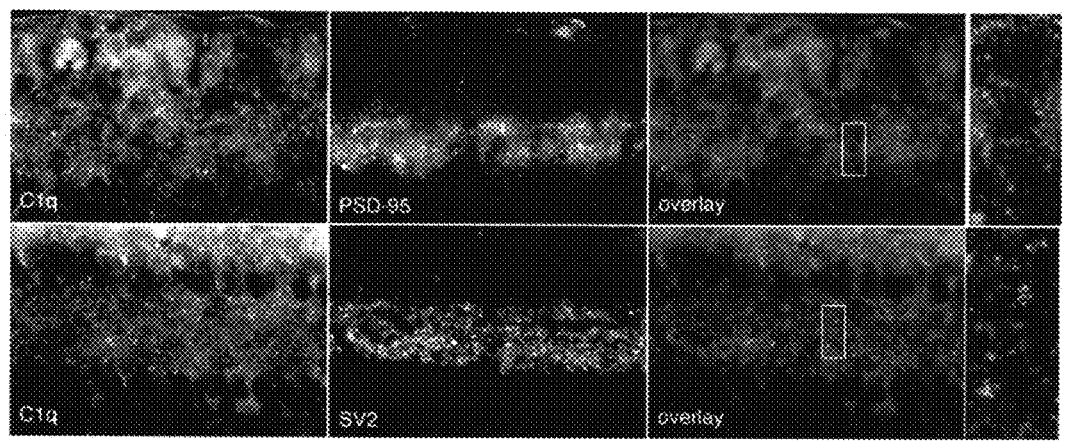
B
C1q immunoreactivity (P5 retina)
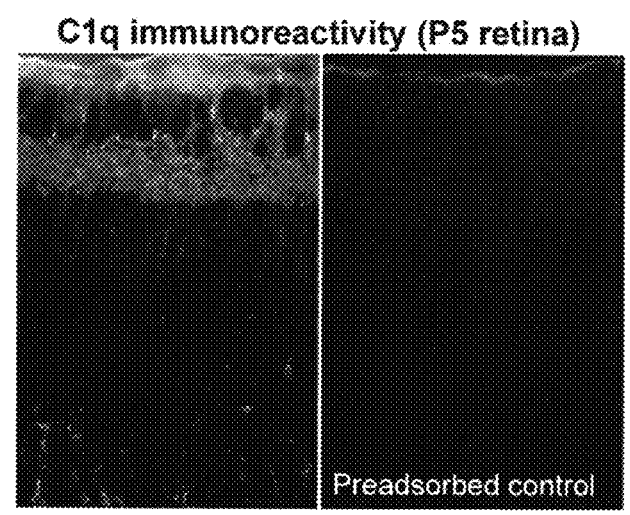

In both WT and KO retinas, neighboring ganglion cells are more correlated in their firing than those located at further distances from one another

Figure 12
A
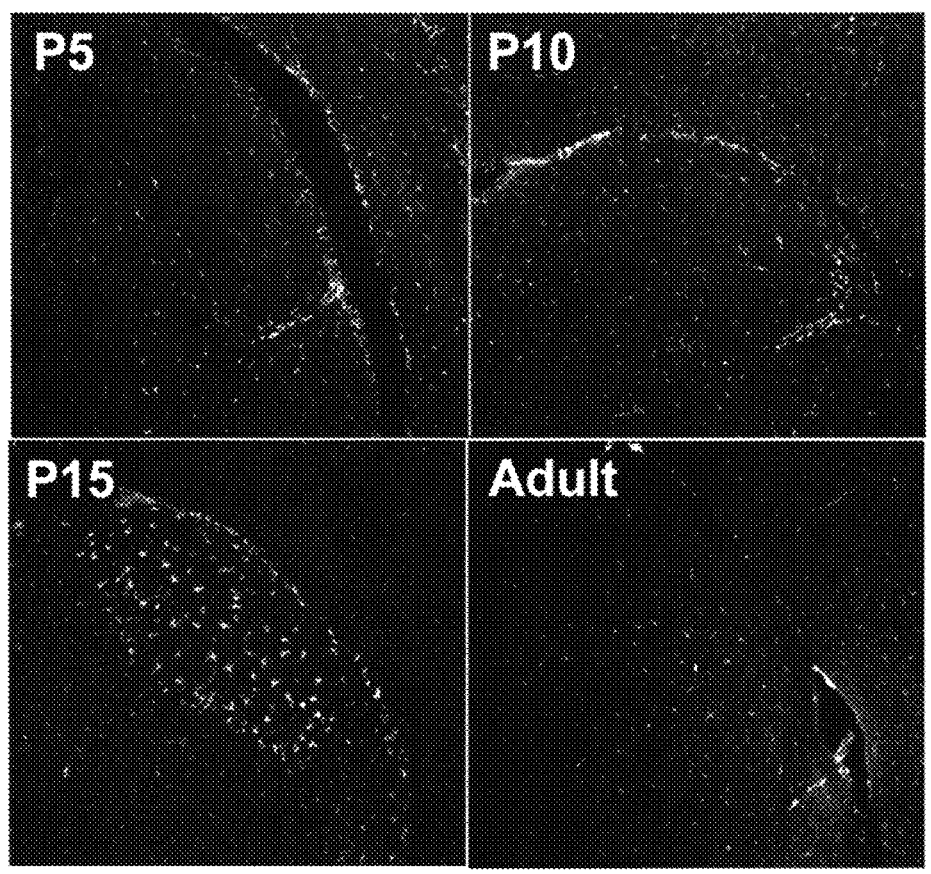
B
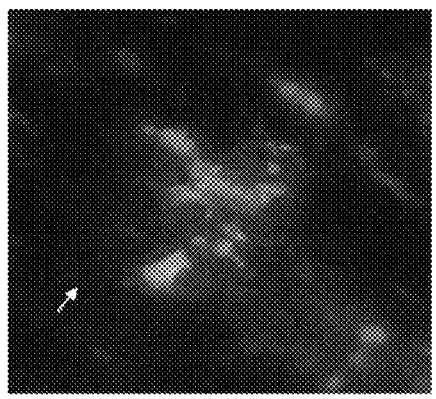

Figure 15
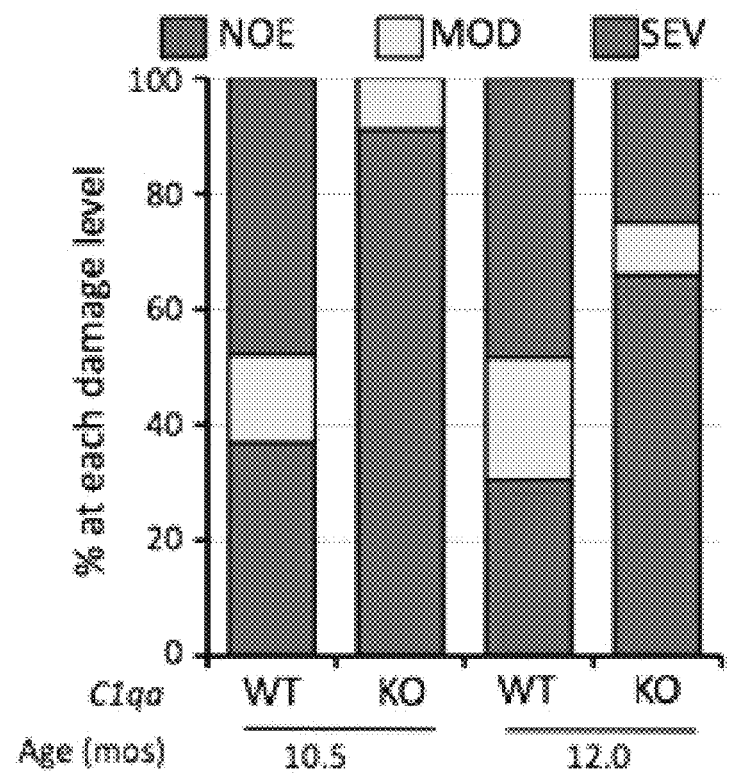
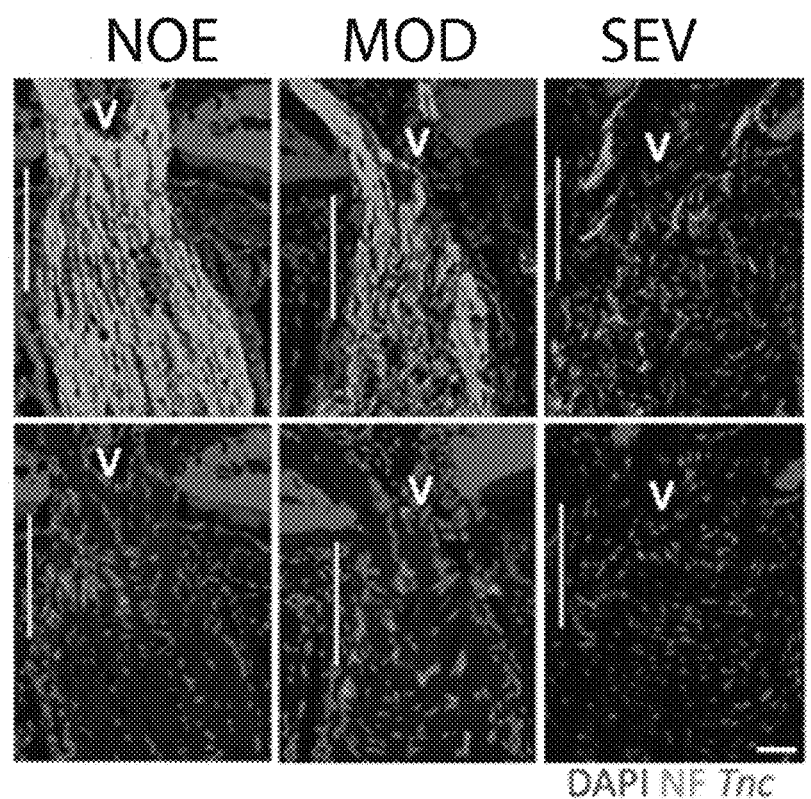

Figure 18 (continued)
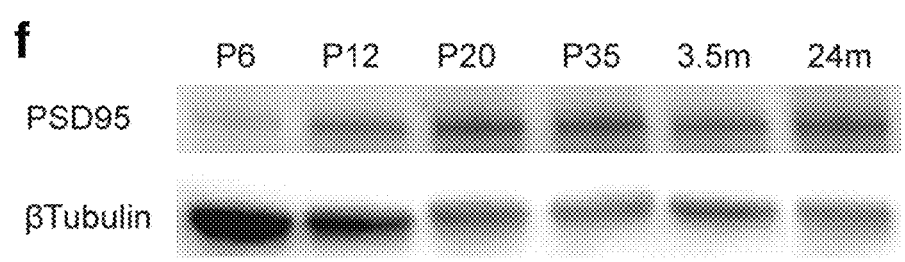
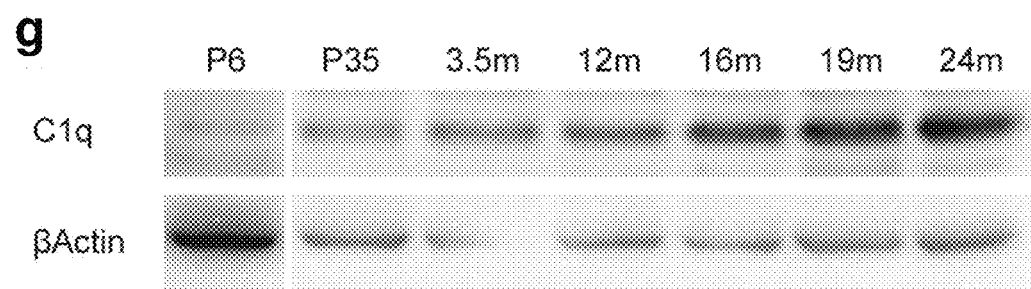
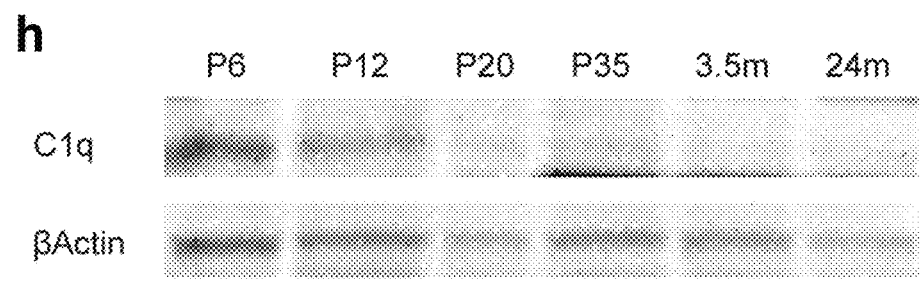

C1q – high exposure

C1q – high exposure

Figure 24
A
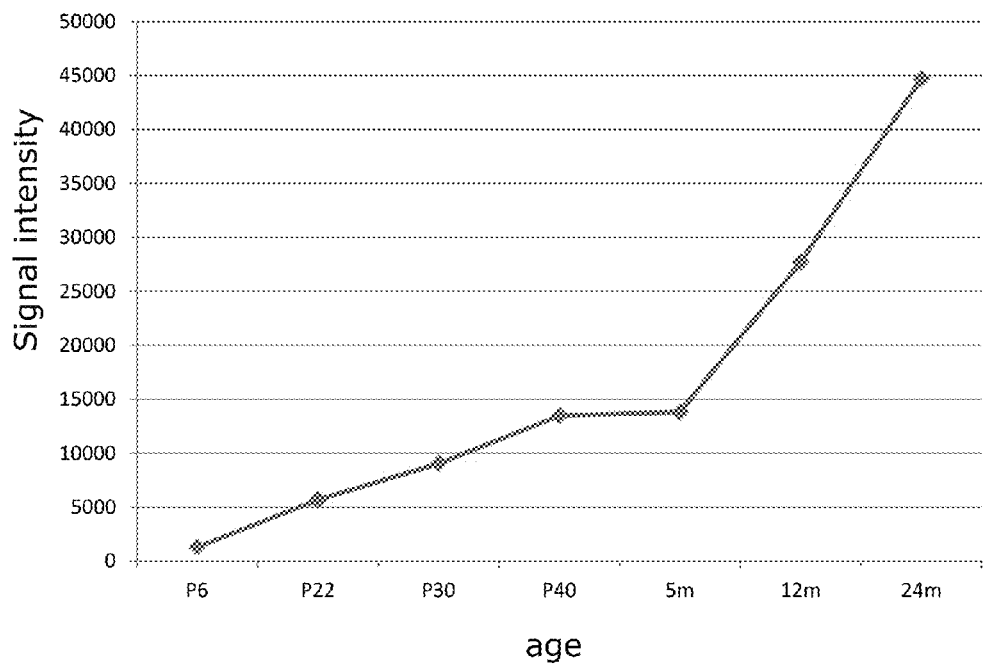
B
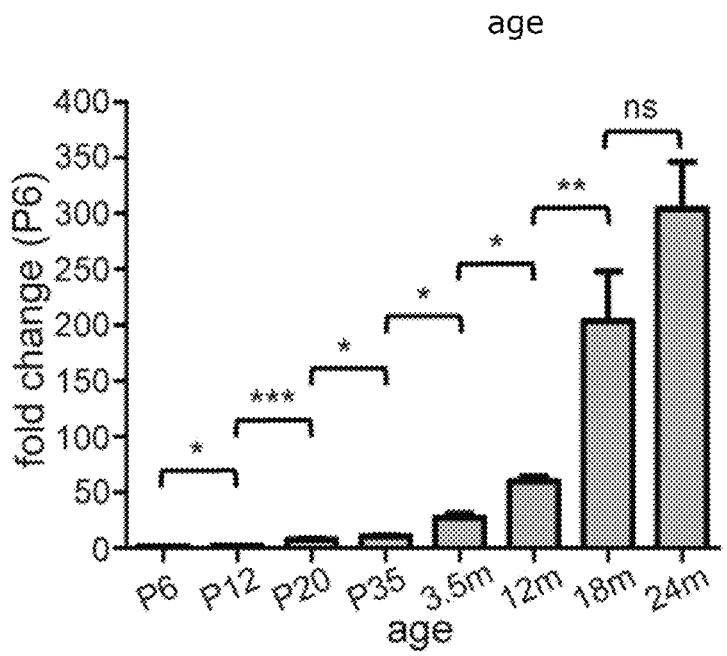

b

Figure 39
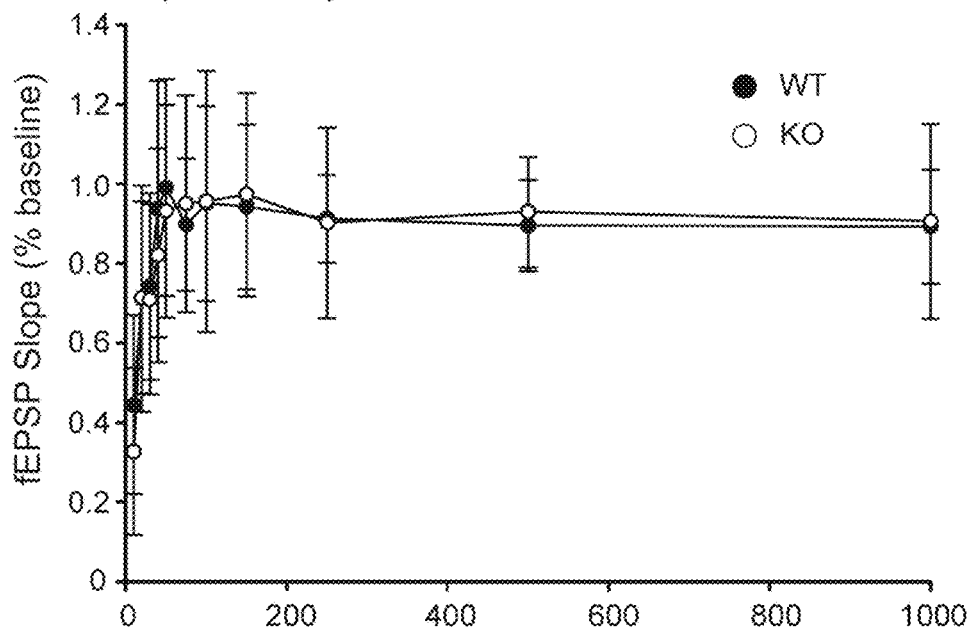
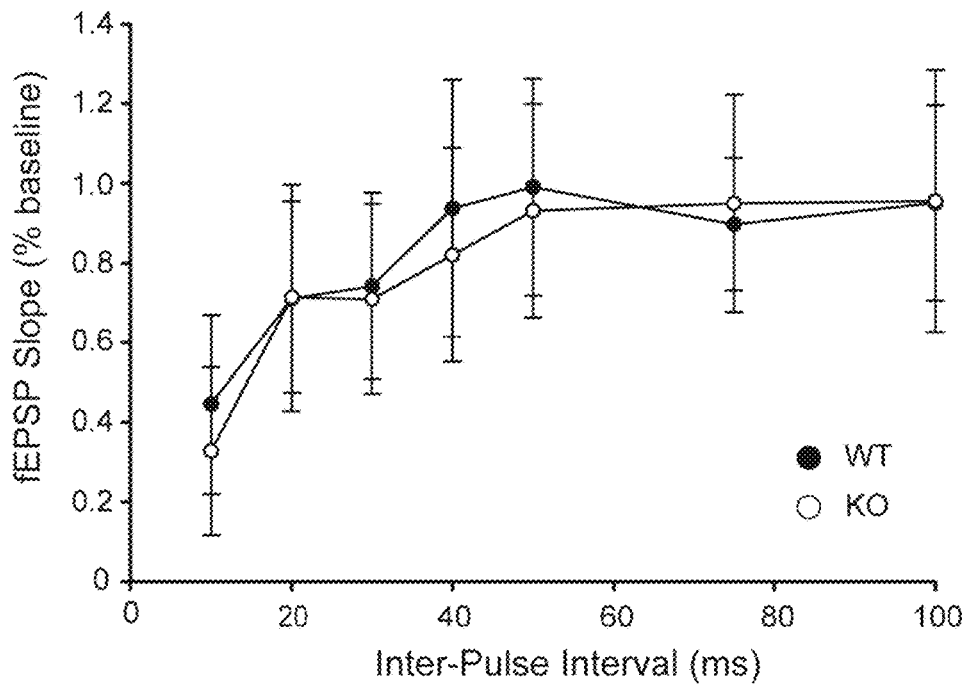

Figure 39 (continued)
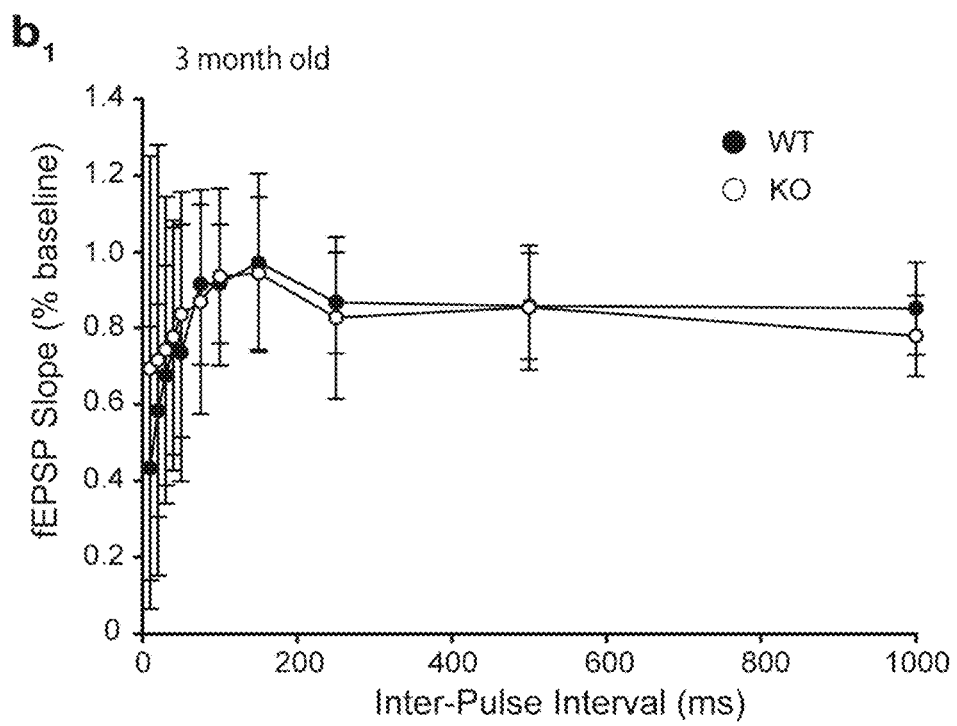
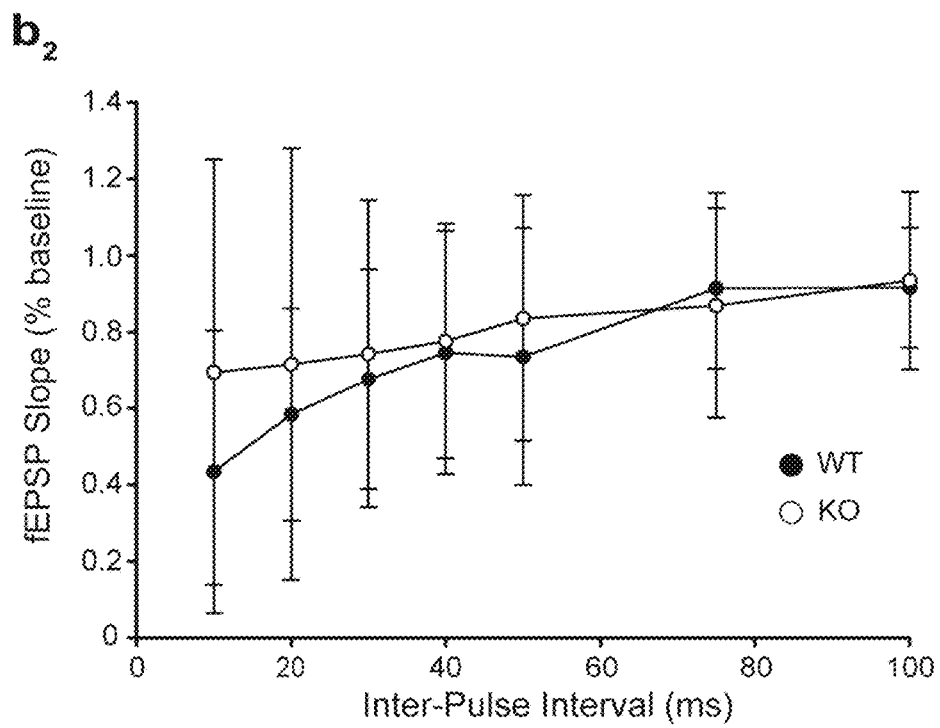

Figure 40 a

| | WT (n=11) | | KO (n=14) | | Bio Ctrl (n=10) | |
|---|---|---|---|---|---|---|
| Behavior in Viewing Jar | MEAN | SEM | MEAN | SEM | MEAN | SEM |
| Body Position (0-2) | 1.00 | 0.00 | 1.29 | 0.13 | 0.90 | 0.10 |
| Tremor (0-1) | 0.09 | 0.09 | 0.29 | 0.13 | 0.10 | 0.10 |
| Palpebral Closure (0-1) | 0.00 | 0.00 | 0.00 | 0.00 | 0.00 | 0.00 |
| Coat Appearance (0-1) | 0.00 | 0.00 | 0.00 | 0.00 | 0.10 | 0.10 |
| Whiskers (0-1) | 0.00 | 0.00 | 0.00 | 0.00 | 0.00 | 0.00 |
| Lacrimation (0-1) | 0.00 | 0.00 | 0.00 | 0.00 | 0.00 | 0.00 |
| Defecation (0-1) | 0.64 | 0.15 | 0.57 | 0.14 | 0.70 | 0.15 |
| | | | | | | |
| Behavior In Arena | MEAN | SEM | MEAN | SEM | MEAN | SEM |
| Transfer Arousal (0-2) | 1.36 | 0.15 | 1.71 | 0.13 | 1.80 | 0.13 |
| Locomoter Activity | 22.09 | 1.35 | 21.86 | 1.49 | 19.10 | 1.95 |
| Gait (0-1) | 0.00 | 0.00 | 0.00 | 0.00 | 0.00 | 0.00 |
| Tail Elevation (0-2) | 1.09 | 0.09 | 1.07 | 0.07 | 1.00 | 0.00 |
| Startle Response (0-2) | 1.18 | 0.12 | 1.07 | 0.07 | 0.90 | 0.10 |
| Touch Escape (0-2) | 1.45 | 0.21 | 1.43 | 0.14 | 1.70 | 0.15 |
| | | | | | | |
| Behavior Above Arena | MEAN | SEM | MEAN | SEM | MEAN | SEM |
| Positional Passivity (0-3) | 2.27 | 0.30 | 2.50 | 0.25 | 2.90 | 0.10 |
| Skin Color (0-2) | 1.64 | 0.15 | 1.50 | 0.14 | 1.00 | 0.00 |
| Trunk Curl (0-1) | 0.73 | 0.14 | 0.57 | 0.14 | 0.00 | 0.00 |
| Limb Grasping (0-1) | 0.00 | 0.00 | 0.00 | 0.00 | 0.00 | 0.00 |
| Pinna Reflex (0-1) | 0.00 | 0.00 | 0.07 | 0.07 | 0.20 | 0.13 |
| Corneal Reflex (0-1) | 0.09 | 0.09 | 0.00 | 0.00 | 0.00 | 0.00 |
| Contact Righting Reflex (0-1) | 0.00 | 0.00 | 0.00 | 0.00 | 0.00 | 0.00 |
| Evidence of Biting (0-1) | 0.09 | 0.09 | 0.07 | 0.07 | 0.00 | 0.00 |
| Vocalization (0-1) | 0.27 | 0.14 | 0.29 | 0.13 | 0.70 | 0.15 |
| Visual Reaching (0-2) | 1.00 | 0.27 | 1.36 | 0.20 | 2.00 | 0.00 |

SEQUENCE LISTING

<160> NUMBER OF SEQ ID NOS: 9

<210> SEQ ID NO 1
<211> LENGTH: 39
<212> TYPE: DNA
<213> ORGANISM: Artificial Sequence
<220> FEATURE:
<223> OTHER INFORMATION: Synthetic primer

<400> SEQUENCE: 1
ggccagtgaa ttgtaatacg actcactata gggaggcgg                                 39

<210> SEQ ID NO 2
<211> LENGTH: 29
<212> TYPE: DNA
<213> ORGANISM: Artificial Sequence
<220> FEATURE:
<223> OTHER INFORMATION: Synthetic primer

<400> SEQUENCE: 2
cggaattccc ttctctgccc tgaggacgg                                            29

<210> SEQ ID NO 3
<211> LENGTH: 29
<212> TYPE: DNA
<213> ORGANISM: Artificial Sequence
<220> FEATURE:
<223> OTHER INFORMATION: Synthetic primer

<400> SEQUENCE: 3
cgggatcctt tctgcatgcg gtctcggtc                                            29

<210> SEQ ID NO 4

```
<211> LENGTH: 29
<212> TYPE: DNA
<213> ORGANISM: Artificial Sequence
<220> FEATURE:
<223> OTHER INFORMATION: Synthetic primer

<400> SEQUENCE: 4
cggaattcga caaggtcctc accaaccag                                    29

<210> SEQ ID NO 5
<211> LENGTH: 25
<212> TYPE: DNA
<213> ORGANISM: Artificial Sequence
<220> FEATURE:
<223> OTHER INFORMATION: Synthetic primer

<400> SEQUENCE: 5
cgggatccgg ggtccttctc gatcc                                        25

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
ccgggggagc caggtgtgga g                                            21

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gcacaggttg gccgtatgcg                                              20

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8
ggtcttactc cttggaggcc atgt                                         24

<210> SEQ ID NO 9
<211> LENGTH: 25
<212> TYPE: DNA
<213> ORGANISM: Artificial Sequence
<220> FEATURE:
<223> OTHER INFORMATION: Synthetic primer

<400> SEQUENCE: 9
gaccccttca ttgacctcaa ctaca                                        25
```

MODULATION OF SYNAPTIC MAINTENANCE

CROSS REFERENCE TO RELATED APPLICATIONS

This application is a continuation of and claims priority under 35 U.S.C. § 120 to U.S. Application, U.S. Ser. No. 13/586,556, filed Aug. 15, 2012, which claims priority under 35 U.S.C. § 119(e) to U.S. provisional application, U.S. Ser. No. 61/523,702, filed Aug. 15, 2011, and is also a continuation-in-part of and claims priority under 35 U.S.C. § 120 to U.S. Application, U.S. Ser. No. 13/326,180, filed Dec. 14, 2011, granted as U.S. Pat. No. 9,149,444, which is a continuation of and claims priority under 35 U.S.C. § 120 to U.S. Application, U.S. Ser. No. 11/636,001, filed Dec. 8, 2006, granted as U.S. Pat. No. 8,148,330, which claims priority under 35 U.S.C. § 119(e) to U.S. provisional application, U.S. Ser. No. 60/749,071, filed on Dec. 9, 2005, each of which is incorporated herein by reference.

ACKNOWLEDGEMENT OF GOVERNMENT SUPPORT

This invention was made with Government support under contracts EY011310 and DA015043 awarded by the National Institutes of Health The Government has certain rights in this invention.

BACKGROUND

The formation of precise neuronal circuits during development is a highly regulated and dynamic process. Excess numbers of synapses are first generated to establish the initial wiring pattern of the brain, but the formation of mature, precise neuronal circuits requires the selective elimination and pruning of specific synapses. Neuronal activity plays a critical role in this refinement phase, but surprisingly, the specific molecular mechanisms underlying synapse elimination remain a mystery. In the adult brain, synapse loss often occurs long before the pathology and clinical symptoms in many neurodegenerative diseases. Identification of the instructive molecule(s) that mark synapses for elimination during development could also provide important clinical insight about therapeutic targets for devastating diseases such as Alzheimer's.

Synapses are specialized cell adhesions that are the fundamental functional units of the nervous system, and they are generated during development with amazing precision and fidelity. During synaptogenesis, synapses form, mature, and stabilize and are also eliminated by a process that requires intimate communication between pre- and postsynaptic partners. In addition, there may be environmental determinants that help to control the timing, location, and number of synapses.

Synapses occur between neuron and neuron and, in the periphery, between neuron and effector cell, e.g. muscle. Functional contact between two neurons may occur between axon and cell body, axon and dendrite, cell body and cell body, or dendrite and dendrite. It is this functional contact that allows neurotransmission. Many neurologic and psychiatric diseases are caused by pathologic overactivity or underactivity of neurotransmission; and many drugs can modify neurotransmission, for examples hallucinogens and antipsychotic drugs.

Glial cells associated with synapses, either astrocytes in the CNS or Schwann cells in the PNS, are thought to provide synaptic insulation by preventing neurotransmitter spillover to neighboring synapses and they also help to terminate neurotransmitter action. In addition, glial cells supply synapses with energetic substrates. The possible requirement of glia for synapse formation is suggested by the temporal association of synaptic development with glial development: although most neurons are born prior to the birth of most glia, the vast majority of synapses develop during the first few weeks of postnatal life, during the period of glial generation. For example, axons of retinal ganglion cells (RGCs) reach their target in the superior colliculus by embryonic day 16, but they do not form many synapses until the second postnatal week, coinciding with glial generation. Therefore the formation of many or most synapses is delayed until glial cells are present.

During development, competition between axons causes permanent removal of synaptic connections. The synapses to be eliminated become progressively weaker, are eliminated, and then the competing axon extends axonal processes to occupy those sites. These findings have lead to a simple model in which synaptic transmission produces two postsynaptic signals: a short range protective signal and a longer range elimination (punishment) signal. Functionally weak synapses are not protected from the elimination signal of neighboring stronger synapses, resulting in the disappearance of postsynaptic receptors and withdrawal of the axon. This withdrawal then provides the opportunity for the stronger axon to expand into the vacated territory. The identity of the punishment and protection signals have heretofore been unknown.

Shortly after birth, neonatal brains undergo a period of intense synaptic proliferation to levels far greater than those seen in adult brains. Later in infancy there is a spontaneous, normal period of synaptic pruning or reduction. In rhesus monkeys the synaptic density (i.e., the number of synapses per unit of brain tissue volume) peaks at 2 to 4 months of age and then gradually declines until about age 3 years, where it remains at adult levels. The proliferation and pruning appear to occur uniformly throughout the rhesus cortex.

Data on human brains suggest that these programmed fluctuations in synaptic density also occur, but they vary by brain region. Synaptogenesis in the visual cortex, for example, begins its rapid growth at about age 2 months, peaks at 8 to 10 months, and then declines gradually until about age 10 years. By contrast, synaptogenesis in the frontal cortex begins and peaks later, and pruning is not complete until adolescence. Interpretation of these findings about synaptic density counts is further complicated because synaptogenesis and pruning may occur at different rates in different structures within the same brain region or even for a particular group of neurons in different parts of their dendritic fields.

Two phenomena thought to be related to this process of synaptogenesis and pruning are those of so-called "critical periods" and neural plasticity, both of which have been studied extensively over the past 30 years. Deprivation of adequate sensory or motor input during particular times in a specific brain system's development (i.e., the critical period) can lead to impairments in that system's functioning, both at that time and in the future.

It is now thought that the need for appropriate sensory input is greatest during a brain system's period of rapid synaptogenesis and that experiential input helps shape the particular synaptic connections that are formed and also which ones are eliminated. This process corresponds to the "experience-expectant" type of neural plasticity that is tied to the brain's developmental timetable. By contrast, "experience-dependent" plasticity allows incorporation of useful but idiosyncratic information throughout life. The onset of critical periods and their durations vary widely over the different neural systems in the brain. At present, it is not known whether there are critical periods during which particular types of stimulation are needed and after which plasticity is greatly reduced. Nor is it known whether neuronal plasticity responsiveness is present in discreet, sensitive periods versus demonstrating more gradual decrease over time.

Although there are varied etiologies among neurodegenerative diseases, one cellular commonality which exists among all neurons is the synapse. Degeneration of functional synapses is of crucial importance to understanding the primary mechanisms of overall neurodegeneration. Evidence suggests that synapse loss precedes neuron loss, e.g. in early Alzheimer's Disease (AD). Several studies have correlated synapse loss with clinically defined neurological impairment. For example, statistical analysis has shown that synapse loss is more closely correlated with cognitive impairment in AD than are plaques and tangles. Moreover, a variety of proteins found in pathological hallmarks of neurodegenerative diseases are synaptic proteins or cleavage products of synaptic proteins. These include APP, amyloid precursor protein, alpha-synuclein, the precursor of NAC peptide found in Lewy bodies in Parkinson's Disease, and PrP.

These observations emphasize that synapse loss is a central event in neurodegeneration and that synaptic proteins have been involved in the neuropathology of disease. Despite this fundamental understanding, there has been little systematic study of synapse loss or the role of synaptic proteins associated with pathology. The modulation of synapse maintenance and loss is of great interest for the treatment of a variety of nervous system disorders. The present invention addresses this issue.

SUMMARY OF THE INVENTION

Methods are provided for the modulation of synaptic development, including synapse elimination. It has been found that specific complement proteins are expressed by neurons, and are involved in the pathway for elimination of synapses. Agents that inhibit complement activation, including agents that block specific components, such as C1q, can prevent synapse elimination from neurons. Neurons affected by synapse loss may be central nervous system neurons, or peripheral nervous system neurons.

In some aspects of the invention, methods are provided for protecting or treating an individual from synapse loss, e.g. an individual suffering from adverse effects of synapse loss, or an individual at risk of suffering from the adverse effects of synapse loss. These findings have broad implications for a variety of clinical conditions, including neurodegenerative conditions involving synaptic loss, which conditions may include aging, Alzheimer's disease; amyotrophic lateral sclerosis; multiple sclerosis, glaucoma, myotonic dystrophy, Down syndrome; Parkinson's disease, Huntington's disease; and the like. The loss of synapses is inhibited by contacting neurons with agents that block complement, including specific components, such as C1q.

In some aspects of the invention, methods are provided for screening candidate agents for the ability to modulate synaptic development, including synapse elimination. In one embodiment of the invention the neurons are neurons in the central nervous system. In another embodiment, the neurons are peripheral nervous system neurons. Screening methods are also provided for determining signaling molecules involved in the synapse elimination pathway, e.g. molecules expressed by astrocytes, including immature astrocytes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 demonstrates that astrocytes up-regulate C1q expression in neurons. A. Gene chip analysis (Affymetrix) of RNA prepared from purified RGCs showed C1q was the only gene significantly (10-30 fold) up-regulated by astrocytes. B. RT-PCR validated that all three chains (A, B, C) of C1q were significantly up-regulated in RGCs upon exposure to astrocytes. C. C1q is highly expressed in retinal ganglion cells in vivo. RT-PCR analysis of mRNA isolated from RGCs that were acutely isolated from P5 retina (left lane), and perfused postnatal mouse retina.

FIG. 3 demonstrate that C1q-deficient mice have defects in synaptic refinement and eye-specific segregation. A. C1q KO mice at P10 (left two rows) and P30 (last two rows) have expanded ipsilateral projections (red) and significant intermingling (overlap) between RGC axons from left and right eyes (yellow) compared to littermate WT controls. Retinogeniculate projection patterns were visualized after injecting βcholera toxin conjugated to Alexa 594 (CTb-594) dye (red) and CTb-488 (green) into left and right eyes of WT and C1q KO mice. Quantification of the percentage of dLGN receiving overlapping inputs from the ipsilateral eye in C1q KO vs WT controls at P10 (B) and P30 (C). C1q KO mice exhibit significantly more overlap than WT mice, regardless of threshold.

FIG. 6 illustrates that complement C3 is expressed at developing CNS synapses. A Double immunohistochemistry with the synaptic antibody SV2, revealed that many C3-positive puncta co-localized with synaptic puncta in the developing (P5), but not the adult brain (P60). B. Western blot analysis of protein lysates prepared from perfused, developing cortex. A clear band for iC3b (43 kD) was observed in postnatal cortex, and C3b levels were significantly down-regulated by P30.

FIG. 7 demonstrates that Complement—deficient mice have more synapses. A. Immunohistochemistry of pre-synaptic protein, vGLUT2 in the superior colliculi (SC) and dLGN of P16 C1q KO and control mice indicate an increase in average intensity of staining in C1q KOs. Sections were processed and immunostained in parallel and all images were collected at identical cameral exposures. B. High resolution confocal microscopy imaging revealed a higher density of postsynaptic PSD95 puncta (green) in dLGNs of P16 C1q KO mice compared to littermate controls.

FIG. 9 illustrates the localization of C1q within the synapseA. C1q-positive puncta in the IPL of postnatal mice were in close apposition with synaptic puncta identified by co-immunostaining with pre and post-synaptic markers, PSD95 (top) and SV2 (bottom). B. The synaptic pattern of C1q immunoreactivity in the retina (left) was not detected after preadsorbing C1q antibodies with purified C1q protein (right).

FIG. 12 demonstrates that microglia, the resident phagocytes in the brain, express receptors for complement (C3 and C1q). Phagocytic microglia in dLGN were stained with anti-CD68 at different developmental timepoints. CD68+ microglia most strongly label the dLGN at P15, a time of active synapse elimination. B. An example of engulfment of RGC terminals (red, CTR) by CD68+ microglia (green) were observed in the dLGN during the synapse elimination period (P10-P15).

FIG. 24 demonstrates quantification of C1q protein levels dramatically increasing in the aging mouse brain. (A) Quantification of Western blot signals in FIG. 21. (B) Quantification of Western blot signals, normalized to β Tubulin loading controls. Quantification confirmed that C1q protein dramatically increased with age to about 300 fold at 24 month of age when normalized to postnatal day six (P6) levels (301+/−33.32, P=0.003, unpaired t-test; n=3 animals/age). Every age analyzed revealed a significant increase in C1q-protein levels when compared to the next younger age from P6 to 18 month of age C1q levels, normalized to P6 levels: P6: 1-fold, +/−0.02; P12: 3-fold+/−0.24; P20: 8-fold+/−0.60; P35: 12-fold+/−1.04; 3.5 month: 27-fold+/−3.73; 12 month old: 59-fold+/−3.10; 18 month old: 204-fold+/−12.29; n=3 animals/age. Significance: P12 versus P6: P=0.019; P20 versus P12: P=0.0005; P35 versus P20: P=0.019; 3.5 month versus P35: P=0.043; 12 month versus 3.5 month: P=0.012; 18 month versus 12 month: P=0.0017). C1q levels in 24 month old brains were not significantly different to the levels measured at 18 month (P=0.104). P—postnatal day; m—month; per.—perfused; n.p.—not perfused; scale bars: a, b, 1 mm; c, d, 100 μm; ns—not significant, *P<0.05, **P<0.01. Values represent mean+/−S.E.M. Error bars represent S.E.M.

FIG. 39 demonstrates that C1q-deficiency did not affect paired-pulse facilitation in the murine hippocampus. a, b, Paired-pulse facilitation analyses in the mouse Dentae Gyrus molecular layer from early postnatal mice (a, postnatal day 14-17) and adult mice (b, 3 month old) did not reveal any differences in presynaptic activity between C1q KO (KO) and their wild-type littermates (WT). a1 and b1: data for all inter-pulse interval ranges recorded, a2 and b2: higher resolution of the short inter-pulse interval data points. All data points represent group averages from C1q KO or C1q wild-type littermate cohorts. Postnatal day 14-17: n=6 (C1q WT), 6 (C1q KO); 3 month old: n=10 (C1q WT), 12 (C1q KO); Error bars represent S.E.M.

DETAILED DESCRIPTION OF THE INVENTION

Figure 2:
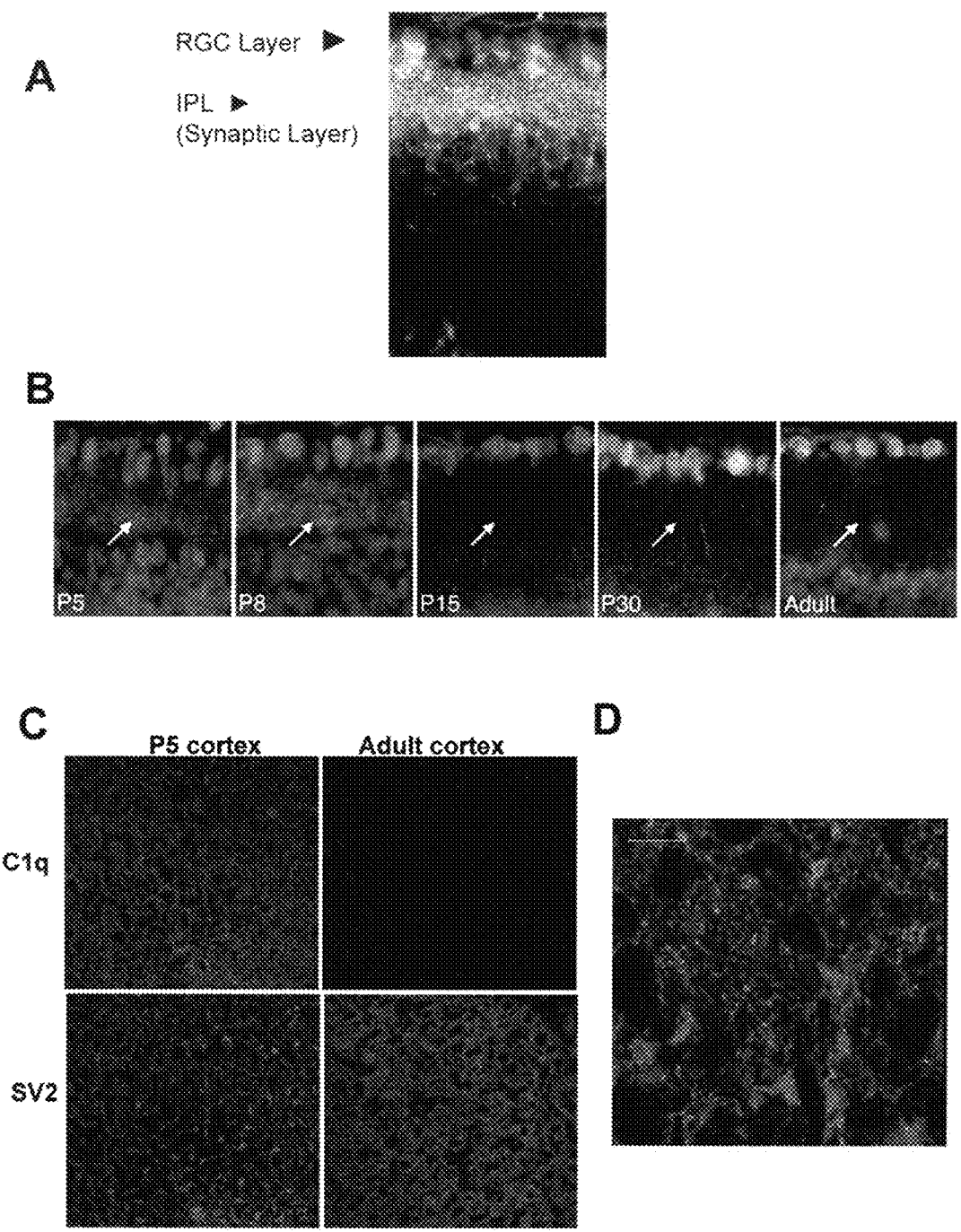
FIG. 2 demonstrates that C1q is localized to developing CNS synapses in vivo. A. Longitudinal cryosection of P5 mouse retina stained with anti-C1q. A punctate pattern of C1q immunoreactivity was observed in the ganglion cell layer (GCL) and synaptic inner plexiform layer (IPL). B. Developmental localization of C1q to synapses in the IPL of the mouse retina. C. Double labeling of C1q (green) with pre synaptic marker SV2 (red) demonstrate punctuate C1q-immunoreactivity in close proximity to synaptic puncta in postnatal (P5), but not adult (P45) mouse cortex. Protein studies using more sensitive reagents (see, e.g., FIG. 33) demonstrates that C1q is localized to synaptic puncta in adult mouse cortex as well. D. Higher magnification confocal image of C1q (green) and synaptic puncta in P5 mouse cortex.

Methods are provided for protecting or treating an individual suffering from adverse effects of synapse loss, e.g. preventing additional synapse loss in an individual suffering from the synapse loss and the affects thereof, prophylactically preventing synapse loss in an individual, e.g. an individual at risk for synapse loss, etc. It is shown herein that immature astrocytes in normal development produce a signal that induces neurons to express specific complement proteins, thus enabling a developmental window during which synapse elimination occurs. Expression of these proteins in development mirrors the period of developmental synaptogenesis, being off in embryonic brain and on at higher levels in postnatal brain. Expression of these specific complement proteins is also upregulated in the older adult brain and in neurodegenerative conditions, thus enabling unwanted synapse elimination in these aging-associated conditions.

These findings have broad implications for a variety of clinical conditions, for example cognitive decline associated with aging where synapse loss is involved, e.g. natural aging and aging-associated neurodegenerative conditions. Synapse loss is inhibited by contacting neurons with inhibitors or antagonists of the complement pathway. For example, inhibitors can block activation of the complement cascade, can block the expression of specific complement proteins in neurons, can interfere with signaling molecules that induce complement activation, can upregulate expression of complement inhibitors in neurons, and otherwise interfere with the role of complement in synapse loss. The ability to prevent synapse loss, e.g. in adult brains, has important implications for maintaining normal neuronal function in a variety of neurodegenerative conditions.

Definitions

Synapse Loss.

Synapses are asymmetric communication junctions formed between two neurons, or, at the neuromuscular junction (NMJ) between a neuron and a muscle cell. Chemical synapses enable cell-to-cell communication via secretion of neurotransmitters, whereas in electrical synapses signals are transmitted through gap junctions, specialized intercellular channels that permit ionic current flow. In addition to ions, other molecules that modulate synaptic function (such as ATP and second messenger molecules) can diffuse through gap junctional pores. At the mature NMJ, pre- and postsynaptic membranes are separated by a synaptic cleft containing extracellular proteins that form the basal lamina. Synaptic vesicles are clustered at the presynaptic release site, transmitter receptors are clustered in junctional folds at the postsynaptic membrane, and glial processes surround the nerve terminal.

Synaptogenesis is a dynamic process. During development, more synapses are established than ultimately will be retained. Therefore, the elimination of excess synaptic inputs is a critical step in synaptic circuit maturation. Synapse elimination is a competitive process that involves interactions between pre- and postsynaptic partners. In the CNS, as with the NMJ, a developmental, activity-dependent remodeling of synaptic circuits takes place by a process that may involve the selective stabilization of coactive inputs and the elimination of inputs with uncorrelated activity. The anatomical refinement of synaptic circuits occurs at the level of individual axons and dendrites by a dynamic process that involves rapid elimination of synapses. As axons branch and remodel, synapses form and dismantle with synapse elimination occurring rapidly.

In addition to the normal developmental loss, synapse loss is an early pathological event common to many neurodegenerative conditions, and is the best correlate to the neuronal and cognitive impairment associated with these conditions. Studies in the brains of patients with pre-clinical Alzheimer's disease (AD), as well as in transgenic animal models have shown that synaptic damage occurs early in disease progression. This early disruption of synaptic connections in the brain results in neuronal dysfunction that, in turn, leads to the characteristic symptoms of dementia and/or motor impairment observed in several neurodegenerative disorders.

Several molecules involved in AD and other neurodegenerative disorders play an important role in synaptic function. For example, AβPP has a preferential localization at central and peripheral synaptic sites. In transgenic mice, abnormal expression of mutant forms of AβPP results not only in amyloid deposition, but also in widespread synaptic damage. This synaptic pathology occurs early and is associated with levels of soluble Aβ1-42 rather than with plaque formation. Other neurodegenerative diseases where gene products have been shown to be closely associated with synaptic complexes include Huntington's disease (HD) and myotonic dystrophy (DM). Huntingtin is a membrane-bound protein with a distribution very similar to that of synaptic vesicle protein synaptophysin. Studies in human brain detected htt in perikarya of some neurons, neuropil, varicosities and as punctate staining likely to be nerve endings. The serine/threonine kinase (DMK), which is the gene product of the DM gene, has been found to localize post-synaptically at the neuromuscular junction of skeletal muscle and at intercalated discs of cardiac tissue. DMK was also found at synaptic sites in the cerebellum, hippocampus, midbrain and medulla. By "modulation" of synapse loss as used herein, it is meant that the number of synapses lost is either enhanced or suppressed as required in the specific situation. As used herein, the term "modulator of synapse loss" refers to an agent that is able to alter synapse loss. Modulators include, but are not limited to, both "activators" and "inhibitors". An "activator" or "agonist" is a substance that enhances synapse loss. Conversely, an "inhibitor" or "antagonist" decreases synapse loss. The reduction may be complete or partial. As used herein, modulators include, without limitation, C1q antagonists and agonists. Agonists and antagonists may include proteins, nucleic acids, carbohydrates, antibodies, or any other molecules that decrease the effect of a protein. The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

Complement.

Complement is a system of plasma proteins that interacts with the cell surfaces of pathogens or cells to mark them for destruction by phagocytes. The complement system is made up of a large number of distinct plasma proteins, primarily produced by the liver. A number of these proteins are a class of proteases, called zymogens, which are themselves activated by proteolytic cleavage. These zymogens can thus be widely distributed without being active until activated by a local pathogen. The complement system thus is activated through a triggered enzyme cascade.

The classical pathway is activated by the binding of the complement protein C1q directly to the cell surface or to an antibody that is bound to the cell surface. C1q is a large multimeric protein of 460 kDa consisting of 18 polypeptide chains (6 C1q A chains, 6 C1q B chains, and 6 C1q C chains). C1r and C1s complement proteins to bind to the C1q tail region to form the C1 complex. Binding of the C1q complex to the surface of a cell or to the complement binding domain of an antibody Fc region induces a conformational change in C1q that leads to activation of an autocatalytic enzymatic activity in C1r, which then cleaves C1s to generate an active serine protease. Once activated, C1s cleaves C4, etc, leading to the complement cascade sequence. Ultimately this pathway leads to the formation of a membrane attack complex which lyses and kills the affected cell. Normal cells, including neurons, express molecules such as CD59 that protect them from lysis or damage from the membrane attack complex and the C1 inhibitor (C1-INH) which dissociates C1r and C1s from the active C1 complex.

Various complement proteins are expressed by neurons and glial cells in vitro and in vivo. Their function in the brain is unknown. The expression of many of these complement proteins is upregulated by serum or inflammatory cytokines or after brain injury. Astrocytes in culture have been reported to express C1q, C1r, C1s, C4, C2, and C3, as well as the more terminal proteins. Neurons have been reported to express C4 and C3, but only to express C1q after brain injury.

Three pathways have been elucidated through which the complement cascade can be initiated; classical, alternate and lectin Pathways. All three pathways merge through at common intersection, complement C3. C3 is an acute phase reactant. The liver is the main site of synthesis, although small amounts are also produced by activated monocytes and macrophages. A single chain precursor (pro-C3) of approximately 200 kD is found intracellularly; the cDNA shows that it comprises 1,663 amino acids. This is processed by proteolytic cleavage into alpha and beta subunits which in the mature protein are linked by disulfide bonds. Pro-C3 contains a signal peptide of 22 amino acid residues, the beta chain (645 residues) and the alpha chain (992 residues). The 2 chains are joined by 4 arginine residues that are not present in the mature protein. In the alternate pathway complement C3 undergoes spontaneous cleavage resulting in complement B binding to C3b. Diffusion of the Ba subunit results in an active alternate pathway C3 convertase (C3bBb). C3bBb is stabilized by binding to properdin prior to merging.

Inhibition of Complement.

A number of molecules are known that inhibit the activity of complement. As described above, normal cells can produce proteins that block complement activity, i.e., that naturally block complement activity, e.g. CD59, C1 inhibitor, etc. In some embodiments of the invention, complement is inhibited by upregulating expression of genes encoding such polypeptides. Modified molecules that block complement activation, e.g. dominant negative polypeptides of complement cascade proteins, are also known, which can be exogenously provided to the cells as a soluble peptide or which can be ectopically expressed in cells by contacting the cells with a nucleic acid comprising the dominant negative polypeptide. Moreover, small molecule inhibitors of complement signaling have been identified which may be provided to the cells.

For example, the activity of the C1 complex (composed of 1 molecule of C1q, 3 molecules of C1r, and 2 molecules of C1s) may be inhibited. Any inhibitor of C1 complex function, e.g. inhibitors of binding of the C1 complex to an antigen or pathogen, inhibitors of binding between C1q, C1r and C1s; inhibitors of C1r activation by C1q; inhibitors of C1s cleavage by C1r; inhibitors C1s protease activity on C4, may be employed in the subject methods. For example, naturally occurring inhibitors of the C1 complex such as C1 Inhibitor and Chondroitin Sulfate Proteoglycan (CSPG) may be used. C1 Inhibitor is a member of the "serpin" family of serine protease inhibitors; it is a heavily glycosylated plasma protein that prevents fluid-phase C1 activity by blocking the active site of C1r and C1s and dissociating them from C1q. CSPG binds to the complement protein C1q and inhibits complex formation of C1 (Kirschfink et al., 1997, J Immunol 158 (3):1324-1331). Another example of inhibitors of C1 complex are dominant negative polypeptide inhibitors, e.g. soluble versions of C1q receptors such as soluble CR1, soluble CR1 (sCR1), soluble cC1qR/caltreticulin, soluble gC1qR, soluble C1qRp, etc. For example, the mature protein of the most common allotype of CR1 contains 1998 amino acid residues: an extracellular domain of 1930 residues, a transmembrane region of 25 residues, and a cytoplasmic domain of 43 residues. The entire extracellular domain is composed of 30 repeating units (FIG. 2) referred to as short consensus repeats (SCRs) or complement control protein repeats (CCPRs), each consisting of 60 to 70 amino acid residues. Recent data indicate that C1q binds specifically to human CR1. A soluble version of recombinant human CR1 (sCR1) lacking the transmembrane and cytoplasmic domains has been produced and shown to retain all the known functions of the native CR1. Other C1q receptors (C1qR) have been described (see the review by McGreal and Gasque, 2002, Biochem Soc Trans 39 (Pt.6):1010-4), any of which may be modified to produce dominant negative polypeptides that will bind C1q to inhibit C1 complex binding to cells. Other examples of inhibitors of C1 complex that find use in the subject methods include the synthetic peptide C1q B chain helical region (Fryer et al., 1997); the sulfated polysaccharide Fucan (Charreau et al., 1997); small molecule inhibitors of C1 complex activity such as the C1 s inhibitors BCX-1470 (K-76 analog, Kaufman et al., 1995), K-76 derivatives (Sindelar et al. 1996; Tanaka 1996) C1s-INH-248 (Buerke et al. 2001. J immunol 167(9):5375-80), and thiopheneamidine-based inhibitors (Subasinghe et al. 2004. Biororg Med Chem Lett. 14(12):3043-7); and glycosaminoglycans such as heparin (te Velthuis et al., 1996) and the highly sulfated low molecular weight heparin derivative LU 51198 (Gralinski et al., 1997).

As another example, the activity of the C5 convertase complex (C4b2a3b) may be inhibited. Any inhibitor of C5 convertase activity, e.g. inhibitors of binding of C4b, C2a, and C3b; cleavage of C5 into C5a and C5b by the C5 convertase, activity of C5a or C5b etc., may be used. One such example of an inhibitor would be a dominant negative polypeptide based on Decay accelerating factor (DAF). DAF (CD55) is composed of four SCRs plus a serine/threonine-enriched domain that is capable of extensive O-linked glycosylation. DAF is attached to cell membranes by a glycosyl phosphatidyl inositol (GPI) anchor and, through its ability to bind C4b and C3b, it acts by dissociating the C3 and C5 convertases. Soluble versions of DAF (sDAF) have been shown to inhibit complement activation. Other examples inhibitors of C5 convertase activity include the *Streptomyces* peptide Complestatin (Momota et al., 1991); synthetic peptides such as C5aRAM (van Oostrum et al., 1996), C5a C-terminal octapeptides (Kawai et al., 1992), C5a His67-modified C-terminal octapeptide analogues (Or et al., 1992), and C089 (C5a hexapeptide, Konteatis et al., 1994); and small molecule antagonists such as L-156,602 (Tsuji et al., 1992) and FUT-175 (nafamstat mesilate, Inose rt al. 1997).

As another example, the activity of the C3 convertase complex (C3bBb3b) may be inhibited. Any inhibitor of C3 convertase activity, e.g. inhibitors of binding of C3b to Bb; cleavage of C3 into C3a and C3b by the C3 convertase, activity of C3a or C3b etc., may be used. Examples of such inhibitors include polypeptides such as cobra venom factor bCVFb (Jungi and McGregor, 1979), dominant negative inhibitors of DAF as described above, synthetic peptide antagonists of C3a comprising C-terminal modifications (Kretzschmar et al., 1992), and small molecule antagonists such as FUT-175 (nafamstat mesilate, Inose et al. 1997).

Other examples of members of the complement cascade that may be inhibited include Factor B, which can be inhibited by, e.g., Factor B-related hexapeptides (Lesavre et al., 1982); Factor D, which can be inhibited by, e.g., DFP (Diisopropyl fluorophosphates, Cole et al., 1997); components C2, C3 and C4, which can be inhibited by, e.g., M5, a fibrin(ogen)olytic proteinase from *Crotalus molossus molossus* (Chen and Rael, 1997)

In addition to known compounds, suitable inhibitors can be screened by methods described herein. Any convenient agent that modulates the activity of any member or complex so as to inhibit the activity of the complement pathway may be employed.

Conditions of Interest

By "neurological" or "cognitive" function as used herein, it is meant that the decrease of synapses in the brain enhances the patient's ability to think, function, etc. As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender.

Among the conditions of interest for the present methods of inhibiting synapse loss are included a variety of aging-associated neurodegenerative conditions, e.g. naturally occurring aging, Alzheimer's disease, Down syndrome, Huntington's disease, amyotrophic lateral sclerosis, multiple sclerosis, myotonic dystrophy, glaucoma, Parkinson's disease; and the like. Such conditions benefit from administration of inhibitors of complement, including inhibitors of C1q, which allow maintenance, or reduced loss, of synapses. In some instances, where there has been neuronal loss, it may be desirable to enhance neurogenesis as well, e.g. through administration of agents or regimens that increase neurogenesis, transplantation of neuronal progenitors, etc. Agents that enhance synaptogenesis, e.g. such as thrombospondins, may also be administered.

Aging is the accumulation of changes in an organism over time. In the nervous system, it is accompanied by stereotypical structural and neurophysiological changes and variable degrees of cognitive decline. Included in these changes are synapse loss and the loss of neuronal function that results. Synapse loss begins at at least about age 20, and may or may not be accompanied by cognitive decline. Typically, if cognitive decline occurs, it is a modest disruption of memory often referred to as "age-associated cognitive impairment" or "mild cognitive impairment" (MCI) that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function.

Moreover, the exponential buildup of C1q on aging, senescent synapses makes these synapses highly vulnerable to the action of the complement cascade. As a result, almost any injury of the aging brain (sepsis, trauma, toxin, ischemia, etc.) may cause activation of the complement cascade at C1q-coated aging synapses, leading to neurodegeneration and, in some instances, triggering other neurodegenerative diseases such as those described below, thus exacerbating cognitive/memory loss associated with normal aging. As such, any individual at the age in which synapses begin to be lost, e.g. over the age 20, may benefit from the administration of complement inhibitors.

Alzheimer's disease is a progressive, inexorable loss of cognitive function associated with an excessive number of senile plaques in the cerebral cortex and subcortical gray matter, which also contains β-amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Amyotrophic lateral sclerosis (ALS) is a rapidly progressive, invariably fatal neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 yr; 50% die within 3 yr of onset, 20% live 5 yr, and 10% live 10 yr. Diagnostic features include onset during middle or late adult life and progressive, generalized motor involvement without sensory abnormalities. Nerve conduction velocities are normal until late in the disease.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Preventing synapse loss may maintain neuron function in these patients.

Down Syndrome is a chromosomal disorder usually resulting in mental retardation, a characteristic facies, and many other typical features, including microcephaly and short stature. In about 95% of cases, there is an extra whole chromosome 21. At autopsy, adult Down syndrome brains show the typical microscopic findings of Alzheimer's disease, and many persons also develop the associated clinical signs.

Parkinson's Disease is an idiopathic, slowly progressive, degenerative CNS disorder characterized by slow and decreased movement, muscular rigidity, resting tremor, and postural instability. In primary Parkinson's disease, the pigmented neurons of the substantia nigra, locus caeruleus, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration and Myotonic dystrophy is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (eg, diabetes mellitus). Mental retardation is common. Severely affected persons die by their early 50s.

Glaucoma is a common neurodegenerative disease that affects retinal ganglion cells (RGCs). Substantial effort is being expended to determine how RGCs die in glaucoma. Evidence supports the existence of compartmentalised degeneration programs in synapses and dendrites, including RGCs. Recent data, from in vitro studies and from an inherited mouse model of glaucoma, suggest that molecularly distinct degenerative pathways underlie the destruction of RGC somata and RGC axons. In various neurodegenerative diseases, axons, dendrites and synapses often degenerate well before the cells die, and there is increasing evidence that this is important for the production of clinical symptoms and signs.

Huntington's disease (HD) is a hereditary progressive neurodegenerative disorder characterized by the development of emotional, behavioral, and psychiatric abnormalities; loss of previously acquired intellectual or cognitive functioning; and movement abnormalities (motor disturbances). The classic signs of HD include the development of chorea—or involuntary, rapid, irregular, jerky movements that may affect the face, arms, legs, or trunk—as well as the gradual loss of thought processing and acquired intellectual abilities (dementia). There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Multiple Sclerosis is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

The methods of the invention can find use in combination with cell or tissue transplantation to the central nervous system, where such grafts include neural progenitors such as those found in fetal tissues, neural stem cells, embryonic stem cells or other cells and tissues contemplated for neural repair or augmentation. Neural stem/progenitor cells have been described in the art, and their use in a variety of therapeutic protocols has been widely discussed. For example, inter alia, U.S. Pat. No. 6,638,501, Bjornson et al.; U.S. Pat. No. 6,541,255, Snyder et al.; U.S. Pat. No. 6,498,018, Carpenter; U.S. Patent Application 20020012903, Goldman et al.; Palmer et al. (2001) Nature 411(6833):42-3; Palmer et al. (1997) Mol Cell Neurosci. 8(6):389-404; Svendsen et al. (1997) Exp. Neurol. 148(1):135-46 and Shihabuddin (1999) Mol Med Today. 5(11):474-80; each herein specifically incorporated by reference.

Neural stem and progenitor cells can participate in aspects of normal development, including migration along well-established migratory pathways to disseminated CNS regions, differentiation into multiple developmentally- and regionally-appropriate cell types in response to microenvironmental cues, and non-disruptive, non-tumorigenic interspersion with host progenitors and their progeny. Human NSCs are capable of expressing foreign transgenes in vivo in these disseminated locations. A such, these cells find use in the treatment of a variety of conditions, including traumatic injury to the spinal cord, brain, and peripheral nervous system; treatment of degenerative disorders including Alzheimer's disease, Huntington's disease, Parkinson's disease; affective disorders including major depression; stroke; and the like. By synapse loss enhancers, the functional connections of the neurons are enhances, providing for an improved clinical outcome.

Methods of Treatment

The methods of the invention provide for modulating synapse loss through administering agents that are agonists or antagonists of complement. Without being bound by theory, the data provided herein demonstrate that immature astrocytes induce expression of C1q proteins in neurons during development. During the developmental process of synapse elimination, this C1q expression can be coupled with a signal for complement activation, e.g. β-amyloid, APP, cytokines such as IFNγ, TNFα, and the like, thereby eliminating specific synapses. This development pathway may be inappropriately activated in neurodegenerative disease, resulting in the undesirable loss of synapses. By administering agents that alter complement activation, synapses can be maintained that would otherwise be lost. Such agents include C1q inhibitors, agents that upregulate expression of native complement inhibitors, agents that downregulate C1q synthesis in neurons, agents that block complement activation, agents that block the signal for complement activation, and the like.

The methods promote improved maintenance of neuronal function in conditions associated with synapse loss. The maintenance of neural connections provides for functional stabilization and functional improvement in neurodegenerative disease relative to untreated patients. The prevention of synapse loss may comprise at least a measurable improvement relative to a control lacking such treatment, for example at least a 10% improvement in the number of synapses, at least a 20% improvement, at least a 50% improvement, or more.

Methods of the invention reduce the loss of synapses, e.g. the rate of loss, or the total number of synapses lost, where a decrease would otherwise occur. In some instances, inhibiting synapse loss with agents of the invention maintains the number of synapses that were present at the time of first treatment. In other words, inhibiting synapse loss stabilizes the numbers of synapse such that no additional synapses are lost.

In some instances, synapse loss is associated with a decline in neuronal function. As such, inhibiting synapse loss with agents of the invention reduces the decline in neuronal function, i.e. the rate or extent, by, e.g., 30% or more, e.g. 40%, 50%, 60% or more, such as 70%, 80%, or 90% or more, for example, 95% or 100% or more, i.e. such that the loss of neuronal function is negligible, In other words, inhibiting synapse loss may be said to maintain neuronal function, e.g. at the level of function at the time of first treatment with an inhibitor of synapse loss or better, i.e. to improve neuronal function. Neuronal function in humans can be measured by any convenient method, e.g. nerve stimulation to electrically excite peripheral nerves; somatosensory evoked potential techniques to measure processing of sensory input by the brain; electromyography to measure electrical activity in muscles; and transcranial magnetic stimulation, a technique used to investigate the output of the motor cortex to the muscles.

In some instances, synapse loss and the subsequent decline in neuronal function is associated with cognitive decline. By "cognition" it is meant the ability of a person to think, e.g. pay attention, remember, produce and understand language, solve problems, and make decisions. By "cognitive decline", it is meant a decline in the ability of the individual to perform these mental tasks. Inhibiting synapse loss with agents of the invention reduces the rate of cognitive decline by, e.g., 30% or more, e.g. 40%, 50%, 60% or more, such as 70%, 80%, or 90% or more, for example, 95% or 100% or more, i.e. such that cognitive decline is negligible. In other words, inhibiting synapse loss may be said to prevent a cognitive decline and maintain cognition, e.g. at the level of cognition at the time of first treatment with an inhibitor of synapse loss. Cognitive decline can be measured by any convenient method, e.g. tests of memory or other mental functions such as planning, following instructions, or decision-making.

The agents of the present invention are administered at a dosage that decreases synapse loss while minimizing any side-effects. It is contemplated that compositions will be obtained and used under the guidance of a physician for in vivo use. The dosage of the therapeutic formulation will vary widely, depending upon the nature of the disease, the frequency of administration, the manner of administration, the clearance of the agent from the host, and the like.

The effective amount of a therapeutic composition to be given to a particular patient will depend on a variety of factors, several of which will be different from patient to patient. Utilizing ordinary skill, the competent clinician will be able to optimize the dosage of a particular therapeutic or imaging composition in the course of routine clinical trials.

Therapeutic agents, e.g. inhibitors of complement, activators of gene expression, etc. can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intrathecal, nasal, intracheal, etc., administration. The active agent may be systemic after administration or may be localized by the use of regional administration, intramural administration, or use of an implant that acts to retain the active dose at the site of implantation.

One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents is also an option. A BBB disrupting agent can be co-administered with the therapeutic compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g. intravascular (intravenous, intraarterial, intracapillary) administration, injection into the cerebrospinal fluid, intracavity or direct injection in the brain. Intrathecal administration maybe carried out through the use of an Ommaya reservoir, in accordance with known techniques. (F. Balis et al., Am J. Pediatr. Hematol. Oncol. 11, 74, 76 (1989).

Where the therapeutic agents are locally administered in the brain, one method for administration of the therapeutic compositions of the invention is by deposition into or near the site by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the site, into a natural or surgically created cyst, or into the normal brain mass. Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 µl/minute), rather than diffusive flow, to deliver the therapeutic composition to the brain and/or tumor mass. Such devices are described in U.S. Pat. No. 5,720,720, incorporated fully herein by reference.

The effective amount of a therapeutic composition to be given to a particular patient will depend on a variety of factors, several of which will be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing LD50 animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent, e.g. some agents may be taken for extended periods of time on a daily or semi-daily basis, while more selective agents may be administered for more defined time courses, e.g. one, two three or more days, one or more weeks, one or more months, etc., taken daily, semi-daily, semi-weekly, weekly, etc.

Formulations may be optimized for retention and stabilization in the brain. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

In some embodiments, methods of the invention further comprise the step of administering to the patient a therapy for a neurodegenerative condition, i.e. the neurodegenerative condition associated with the synapse loss. In such embodiments, any convenient therapy may be provided. For example, in methods in which the patient has suffered synapse loss as a result of Alzheimer's Disease, the methods may further comprise administering a therapy for Alzheimer's Disease. Any convenient Alzheimer's Disease therapy may be provided, for example, memantine, a cholinesterase inhibitor such as donepezil, rivastigmine, or galantamin, anti-depressants, anti-anxiety medications to reduce agitation or aggression, antipsychotic medications to reduce suspicion or paranoia, etc, The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Gene Delivery

One approach for modulating synapse loss involves gene therapy. In such methods, anti-sense or RNAi sequences encoding C1q or fragments thereof are introduced into the neurons, and expressed as a means of decreasing C1q expression in the targeted synapses. To genetically modify neurons that are protected by the BBB, two general categories of approaches have been used. In one type of approach, cells are genetically altered, outside the body, and then transplanted somewhere in the CNS, usually in an area inside the BBB. In the other type of approach, genetic "vectors" are injected directly into one or more regions in the CNS, to genetically alter cells that are normally protected by the BBB. It should be noted that the terms "transfect" and "transform" are used interchangeably herein. Both terms refer to a process which introduces a foreign gene (also called an "exogenous" gene) into one or more preexisting cells, in a manner which causes the foreign gene(s) to be expressed to form corresponding polypeptides.

A preferred approach introduces into the CNS a source of a desirable sequence, by genetically engineering cells within the CNS. This has been achieved by directly injecting a genetic vector into the CNS, to introduce foreign genes into CNS neurons "in situ" (i.e., neurons which remain in their normal position, inside a patient's brain or spinal cord, throughout the entire genetic transfection or transformation procedure).

Useful vectors include viral vectors, which make use of the lipid envelope or surface shell (also known as the capsid) of a virus. These vectors emulate and use a virus's natural ability to (i) bind to one or more particular surface proteins on certain types of cells, and then (ii) inject the virus's DNA or RNA into the cell. In this manner, viral vectors can deliver and transport a genetically engineered strand of DNA or RNA through the outer membranes of target cells, and into the cells cytoplasm. Gene transfers into CNS neurons have been reported using such vectors derived from herpes simplex viruses (e.g., European Patent 453242, Breakfield et al 1996), adenoviruses (La Salle et al 1993), and adeno-associated viruses (Kaplitt et al 1997).

Non-viral vectors typically contain the transcriptional regulatory elements necessary for expression of the desired gene, and may include an origin of replication, selectable markers and the like, as known in the art. The non-viral genetic vector is then created by adding, to a gene expression construct, selected agents that can aid entry of the gene construct into target cells. Several commonly-used agents include cationic lipids, positively charged molecules such as polylysine or polyethylenimine, and/or ligands that bind to receptors expressed on the surface of the target cell. For the purpose of this discussion, the DNA-adenovirus conjugates described by Curiel (1997) are regarded as non-viral vectors, because the adenovirus capsid protein is added to the gene expression construct to aid the efficient entry of the gene expression construct into the target cell.

In cationic gene vectors, DNA strands are negatively charged, and cell surfaces are also negatively charged. Therefore, a positively-charged agent can help draw them together, and facilitate the entry of the DNA into a target cell. Examples of positively-charged transfection agents include polylysine, polyethylenimine (PEI), and various cationic lipids. The basic procedures for preparing genetic vectors using cationic agents are similar. A solution of the cationic agent (polylysine, PEI, or a cationic lipid preparation) is added to an aqueous solution containing DNA (negatively charged) in an appropriate ratio. The positive and negatively charged components will attract each other, associate, condense, and form molecular complexes. If prepared in the appropriate ratio, the resulting complexes will have some positive charge, which will aid attachment and entry into the negatively charged surface of the target cell. The use of liposomes to deliver foreign genes into sensory neurons is described in various articles such as Sahenk et al 1993. The use of PEI, polylysine, and other cationic agents is described in articles such as Li et al 2000 and Nabel et al 1997.

An alternative strategy for introducing DNA into target cells is to associate the DNA with a molecule that normally enters the cell. This approach was demonstrated in liver cells in U.S. Pat. No. 5,166,320 (Wu et al 1992). An advantage of this approach is that DNA delivery can be targeted to a particular type of cell, by associating the DNA with a molecule that is selectively taken up by that type of target cell. A limited number of molecules are known to undergo receptor mediated endocytosis in neurons. Known agents that bind to neuronal receptors and trigger endocytosis, causing them to enter the neurons, include (i) the non-toxic fragment C of tetanus toxin (e.g., Knight et al 1999); (ii) various lectins derived from plants, such as barley lectin (Horowitz et al 1999) and wheat germ agglutinin lectin (Yoshihara et al 1999); and, (iii) certain neurotrophic factors (e.g., Barde et al 1991). At least some of these endocytotic agents undergo "retrograde" axonal transport within neuron. The term "retrograde", in this context, means that these molecules are actively transported, by cellular processes, from the extremities (or "terminals") of a neuron, along an axon or dendrite, toward and into the main body of the cell, where the nucleus is located. This direction of movement is called "retrograde", because it runs in the opposite direction of the normal outward ("anterograde") movement of most metabolites inside the cell (including proteins synthesized in the cell body, neurotransmitters synthesized by those proteins, etc.).

Compound Screening

In some aspects of the invention, candidate agents are screened for the ability to modulate synapse loss ability and to inhibit cognitive decline, which agents may include candidate complement inhibitors, variants, fragments, mimetics, agonists and antagonists. Such compound screening may be performed using an in vitro model, a genetically altered cell or animal, or purified protein. A wide variety of assays may be used for this purpose. In one embodiment, compounds that are predicted to be antagonists or agonists of complement, including specific complement proteins, e.g. C1q, and complement activating signals, e.g. β-amyloid, APP, etc. are tested in an in vitro culture system, as described below.

For example, candidate agents may be identified by known pharmacology, by structure analysis, by rational drug design using computer based modeling, by binding assays, by cell-free assays and the like for their ability to inhibit complement activity, where the ability of an agent to inhibit complement signaling is indicative of the ability of that agent to inhibit synapse loss and cognitive decline. Various in vitro models may be used to determine whether a compound binds to, or otherwise affects complement activity. Such candidate compounds may used to contact neurons in an environment permissive for synapse loss. Such compounds may be further tested in any convenient in vitro or in vivo model for an effect on synapse loss, and/or for an effect on cognitive decline, e.g. as described in the examples section below.

Screening may also be performed for molecules produced by astrocytes, e.g. immature astrocytes, which induce C1q expression in neurons. In such assays, co-cultures of neurons and astrocytes are assessed for the production or expression of molecules that induce C1q expression. For example, blocking antibodies may be added to the culture to determine the effect on induction of C1q expression in neurons.

Synapse loss is quantitated by administering the candidate agent to neurons in culture, and determining the presence of synapses in the absence or presence of the agent. In one embodiment of the invention, the neurons are a primary culture, e.g. of RGCs. Purified populations of RGCs are obtained by conventional methods, such as sequential immunopanning. The cells are cultured in suitable medium, which will usually comprise appropriate growth factors, e.g. CNTF; BDNF; etc. The neural cells, e.g. RCGs, are cultured for a period of time sufficient allow robust process outgrowth and then cultured with a candidate agent for a period of about 1 day to 1 week. In many embodiments, the neurons are cultured on a live astrocyte cell feeder in order to induce signaling for synapse loss. Methods of culturing astrocyte feeder layers are known in the art. For example, cortical glia can be plated in a medium that does not allow neurons to survive, with removal of non-adherent cells.

For synapse quantification, cultures are fixed, blocked and washed, then stained with antibodies specific synaptic proteins, e.g. synaptotagmin, etc. and visualized with an appropriate reagent, as known in the art. Analysis of the staining may be performed microscopically. In one embodiment, digital images of the fluorescence emission are with a camera and image capture software, adjusted to remove unused portions of the pixel value range and the used pixel values adjusted to utilize the entire pixel value range. Corresponding channel images may be merged to create a color (RGB) image containing the two single-channel images as individual color channels. Co-localized puncta can be identified using a rolling ball background subtraction algorithm to remove low-frequency background from each image channel. Number, mean area, mean minimum and maximum pixel intensities, and mean pixel intensities for all synaptotagmin, PSD-95, and colocalized puncta in the image are recorded and saved to disk for analysis.

The term "agent" as used herein describes any molecule, e.g. protein or pharmaceutical, with the capability of modulating synapse loss, particularly through the complement pathway. Candidate agents also include genetic elements, e.g. anti-sense and RNAi molecules to inhibit C1q expression, and constructs encoding complement inhibitors, e.g. CD 59, and the like. Candidate agents encompass numerous chemical classes, though typically they are organic molecules, including small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Generally a plurality of assay mixtures are run in parallel with different agent concentrations to obtain a differential response to the various concentrations. Typically one of these concentrations serves as a negative control, i.e. at zero concentration or below the level of detection.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example.

Libraries of candidate compounds can also be prepared by rational design. (See generally, Cho et al., Pac. Symp. Biocompat. 305-16, 1998); Sun et al., J. Comput. Aided Mol. Des. 12:597-604, 1998); each incorporated herein by reference in their entirety). For example, libraries of phosphatase inhibitors can be prepared by syntheses of combinatorial chemical libraries (see generally DeWitt et al., Proc. Nat. Acad. Sci. USA 90:6909-13, 1993; International Patent Publication WO 94/08051; Baum, Chem. & Eng. News, 72:20-25, 1994; Burbaum et al., Proc. Nat. Acad. Sci. USA 92:6027-31, 1995; Baldwin et al., J. Am. Chem. Soc. 117: 5588-89, 1995; Nestler et al., J. Org. Chem. 59:4723-24, 1994; Borehardt et al., J. Am. Chem. Soc. 116:373-74, 1994; Ohlmeyer et al., Proc. Nat. Acad. Sci. USA 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing nonhydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Compounds that are initially identified by any screening methods can be further tested to validate the apparent activity. The basic format of such methods involves administering a lead compound identified during an initial screen to an animal that serves as a model for humans and then determining the effects on synapse loss. The animal models utilized in validation studies generally are mammals. Specific examples of suitable animals include, but are not limited to, primates, mice, and rats.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Methods
RGC Gene Expression Analysis Using Affymetrix GeneChip Arrays:
Purified RGCs were plated at a density of ~100,000 cells per well in 6-well dishes and cultured in the presence or absence of a live astrocyte feeding layer for four days. Total RNA was harvested using RNeasy Mini Kit (Qiagen). cDNA was synthesized from 2 µg total RNA using the Gibco BRL Superscript Choice system and a T7-(dT)24 primer [5'-GGCCAG-TGAATTGTAATACGACTCAC-TATAGGGAGGCGG-(dT)24-3' (SEQ ID NO:1)]. Biotinylated cRNA target was prepared by T7 linear amplification using the Bioarray RNA Transcripts Labeling Kit (Enzo) followed by fragmentation. Target was hybridized to Affymetrix Test-2 GeneChip arrays to assess target performance and the Rat U34 genome GeneChip array set following standard Affymetrix protocols. Microarray data was generated in paired triplicates from three independent cultured RGC preparations. Assessment of the quality of sample data and changes in gene expression were analyzed with MicroArray Suite 5.0 software. Genes identified as changing in expression in response to astrocytes increased or decreased at least 2-fold in all three replicates.

Semiquantitative RT-PCR:
Total RNA was prepared as above from RGCs cultured alone or with an astrocyte feeding layer, astrocyte conditioned medium or 5 µg/ml TSP1 for six days. 1 µg total RNA was reverse-transcribed using RETROScript (Ambion) and ½0th of resulting cDNA product was used for PCR. The following PCR primers were used: F-rC1qB (5'-cggaattc-ccttctctgccctgaggacgg-3' (SEQ ID NO:2)), R-rC1qB (5'-cgggat-cctttctgcatgcggtctcggtc-3' (SEQ ID NO:3)), F-mC1qA (5'-cggaattcgacaaggtcc-tcaccaaccag-3' (SEQ ID NO:4)), R-mC1qA (5'-cgggatccggggtccttctcgatcc-3' (SEQ ID NO:5), F-mC1qC (5'-ccgggggagccaggtgtggag-3' (SEQ ID NO:6)), R-mC1qC (5'-gcacaggttggc-cgtatgcg-3' (SEQ ID NO:7)). GAPDH primers were added to all reactions as an internal control (gapdh-s: 5'-GGTCTTACTCCTTGGAG-GCCATGT-3' (SEQ ID NO:8); gapdh-as: 5'-GACCCCT-TCA-T-TGACCTCAACTACA-3' (SEQ ID NO:9)). 2×PCR Mater Mix kit (Promega) was used as supplied by manufacturer with the exception of the addition of 4 mM MgCl2 (5.5 mM final) to the C1qC reaction mix. PCR program was as follows: initial denaturation for 4 min at 94° C.; cycle denaturation for 1 min at 94° C., annealing for 30s at 55° C., and extension for 30 sec at 72° C. (30 cycles total); final extension for 10 min at 72° C. The PCR products were fractionated on 1.5% agarose gel and visualized by ethidium bromide staining. Results shown are representative of three biological replicates.

Preparation of Astrocytes.
Cortical glia were prepared as described (Ullian et al., 2001). Briefly, P1-P2 cortices were papain-digested and plated in tissue culture flasks (Falcon) in a medium that does not allow neurons to survive (Dulbecco's Modified Eagle Medium, fetal bovine serum (10%), penicillin (100 U/ml), streptomycin (100 µg/ml), glutamine (2 mM) and Na-pyruvate (1 mM). After 4 days non-adherent cells were shaken off of the monolayer and cells were incubated another 2-4 days to allow monolayer to refill.

Medium was replaced with fresh medium containing AraC (10 µM) and incubated for 48 hours. Astrocytes were trypsinized and plated onto 24-well inserts (Falcon, 1.0 µm) or 10 cm tissue culture dishes.

Purification and Culture of RGCs.
RGCs were purified by sequential immunopanning to greater than 99.5% purity from P5 mice or Sprague-Dawley rats (Simonsen Labs, Gilroy, Calif.), as previously described (Barres et al., 1988). Approximately 30,000 RGCs were cultured per well in 24-well plates (Falcon) on glass (Assistant) or Aclar 22C (Allied Signal) coverslips coated with poly-D-lysine (10 µg/ml) followed by laminin (2 µg/ml). RGCs were cultured in 600 µl of serum-free medium, modified from Bottenstein and Sato (1979), containing Neurobasal (Gibco), bovine serum albumin, selenium, putrescine, triiodothyronine, transferrin, progesterone, pyruvate (1 mM), glutamine (2 mM), CNTF (10 ng/ml), BDNF (50 ng/ml), insulin (5 μg/ml), and forskolin (10 μM). Recombinant human BDNF and CNTF were generously provided by Regeneron Pharmaceuticals. TTX and Picrotoxin from RBI. All other reagents were obtained from Sigma.

Labeling of Retinogeniculate Afferents.

Mouse pups were anesthetized with inhalant isofluorane. Mice received intravitreal injections of Cholera Toxin-subunit (CTβ) conjugated to Alexa 488 (green label) in the left eye, and CTβ conjugated to Alexa 594 (red label) into the right eye (2-3 μl; 0.5% in sterile saline; Molecular Probes, Eugene Oreg.; CT). 24 hours later mice were transcardially perfused with 4% paraformaldyhyde (ages in text correspond to age at sacrifice), brain tissue was postfixed overnight, cryoprotected in 30% sucrose and then sectioned coronally at 40 μm, mounted onto gelatin-coated slides and coverslipped with Vectashield (Vector Laboratories; Burlingame, Calif.).

Image Quantification and Preparation of Photomicrographs.

Images were digitally acquired with a 3900×3600 pixel color CCD camera (Axiocam; Zeiss; Thornwood, N.Y.). Universal gains and exposures were established for each label. Raw images of the dLGN were imported to Photoshop (Adobe) and cropped to exclude the vLGN and IGL, then the degree of left and right eye axon overlap was quantified using the multi-threshold protocol described in Torborg et al. (2005). This technique is designed to compare overlap across a range of signal:noise values in WT versus transgenic mice. This approach best allows for direct statistical comparison of overlap between various strains of mice at different ages and has been used by others as well (Pak et al., 2004). After quantification, images were imported to Photoshop (Adobe) for adjustments to intensity, cropping, and alignment. In some cases, artifact was removed from outside the boundaries of the dLGN.

The Classical Complement Cascade Mediates Developmental CNS Synapse Elimination.

During development, activity-dependent competition between axons for synaptic territory causes permanent removal of synaptic connections, but what determines which synapses will be eliminated? Excess numbers of synapses are first generated to establish the initial wiring pattern of the brain, but the formation of mature, precise neural circuits requires the selective elimination and pruning of inappropriate synaptic connections.

Much of our understanding of developmental synapse elimination in the brain come from studies carried out in the developing visual system. The retinogeniculate system has proven an excellent model system for studying CNS developmental synapse elimination in vivo. In all binocular animals, axons from retinal ganglion cells (RGCs) terminate in distinct non-overlapping eye-specific domains in the dorsal lateral geniculate nucleus (dLGN). This segregation of retinogeniculate projections into eye-specific territories occurs over a specific and well characterized period in postnatal development, and reflects the elimination of thousands of synapses within incorrect LGN territory and the expansion of axon terminals and formation of synapses within the correct eye specific regions. Synapse elimination also occurs within monocular regions of the LGN during a two week period spanning eye opening (P8-P30 in mouse). Initially, neurons in the rodent dLGN are innervated by multiple (>10) RGC axons, but by the third week of postnatal development, each dLGN neurons receive stable inputs from 1-2 RGC axons. Much like the neuromuscular junction in the peripheral nervous system, this developmental shift in synaptic convergence represents the permanent elimination of inappropriate retinogeniculate synapses, and the maintenance and strengthening of appropriate synaptic connections.

The appearance of astrocytes at synapses in the postnatal brain coincides with this dynamic period of synapse formation and elimination. It has been estimated that fine processes of astrocytes can ensheath as many as 40,000 synapses, and recent research indicate a pivotal role for astrocyte-derived signals in the development of structural and functional of synapses in the brain. Thrombospondin was recently identified as a critical astrocyte-secreted synaptogenic signal, and astrocytes likely secrete other signals that control the development and stabilization of functional synapses.

Here we identify an unexpected and novel role for astrocytes and the classical complement cascade in CNS synapse elimination. The complement system is part of the innate immune system, and is our first line of defense against pathogens and infection. Gene chip studies revealed that only one gene was profoundly up-regulated in neurons by astrocytes; complement protein C1q. C1q's best known role in the immune system is to promote elimination of dead cells, pathogens, and debris. The classical cascade is a triggered enzyme cascade activated by the binding (opsonization) of C1q directly to the membrane surface. C1q opsonization can eliminate unwanted cells by "tagging" them for removal by resident phagocytes, or by further activating the downstream proteases, which ultimately leads to the cleavage of the major complement protein, C3. Like C1q, activated C3 fragments (C3b, C3ib) can directly opsonize cells for phagocytosis, or eliminate unwanted cells via terminal activation of the cascade and the formation of the lytic membrane attack complex.

We hypothesized that complement opsonizes or "tags" synapses for selective elimination during development. The findings reported herein identify C1q and the classical complement cascade as a novel and important mediator of synapse elimination in the developing visual system. In the adult CNS, synapse loss often occurs long before clinical symptoms in many neurodegenerative diseases. We also provide evidence that this complement-dependent mechanism of synapse elimination may be recapitulated in early stages of neurodegenerative diseases, such as glaucoma.

Results

Astrocytes Up-Regulate C1q in CNS Neurons.

We used a genomic approach to screen candidate neuronal genes that are regulated by astrocytes. We took advantage of our ability to grow purified retinal ganglion cells (RGCs) in the complete absence of glia or other retinal cell types. RGCs cultured for several days below a feeding layer of astrocytes have 7-fold more functional synapses than RGCs cultured alone. We used this established experimental paradigm to investigate astrocyte-dependent neuronal gene expression. RNA was collected from postnatal RGCs that had been grown for one week in the presence or absence of astrocytes, and target RNA was hybridized to an Affymetrix gene chip as previously described.

Surprisingly, only one neuronal gene was significantly up-regulated by astrocytes. This gene was identified as complement C1q, an immune system protein thought not to be normally expressed in the brain. C1q is a large multimeric secreted protein composed of six identical subunits with globular heads and long collagen-like tails (Kishore and Reid, 2000). C1q consists of 18 polypeptide chains (6 C1q A chains, 6 C1q B chains, and 6 C1q C chains). We found that all 3 subunits of C1q were up-regulated in purified RGCs by 10-30-fold upon exposure to astrocyte feeding layer (FIG. 1A). The astrocyte-induced increase in C1q A, B, and C mRNA levels in RGC neurons was verified using semi-quantitative RT-PCR (FIG. 1B). Consistent with our in vitro experiments, C1q is highly expressed in retinal ganglion cells in vivo. RT-PCR analysis of mRNA isolated from RGCs that were acutely isolated (P5) indicate expression of C1q (FIG. 1C). In addition, C1q mRNA was detected in samples of perfused postnatal mouse retina. C1q levels were highest in the early postnatal retina (P5-P10), and declined precipitously after P15 (FIG. 1C). This developmental expression pattern for astrocyte-induced C1q gene expression in neurons corresponds to the appearance of astrocytes in the postnatal CNS, and the period of synaptic refinement of retinal axons in the visual system, and suggests the possibility that C1q has a functional role in synaptic pruning.

C1q is Expressed at Synapses in the Developing CNS.

We performed immunostaining experiments in cryosections of rodent tissue at different developmental timepoints. Using several different C1q antisera, we found a bright, punctate pattern C1q immunoreactivity throughout the developing brain and retina. Punctate C1q immunoreactivity was highly localized to the synaptic inner plexiform layer (IPL) of postnatnal mouse retinas, and was also observed in a subset of developing RGCs (FIG. 2A). Consistent with the expression pattern of C1q mRNA in the postnatal retina (FIG. 1C), we found that C1q protein expression and synaptic localization follow a similar developmental pattern (FIG. 2B). In addition, many C1q-positive puncta in the IPL were in close apposition with synaptic puncta identified by co-immunostaining with pre and post-synaptic markers (FIG. 9A).

C1q protein is also highly expressed in synaptic regions of early postnatal rodent brain (P4-P10) (FIG. 2C). Double labeling with synaptic antibodies such as SV2, demonstrate punctate C1q-immunoreactivity in close proximity to synaptic puncta (FIG. 2D). As in the retina, the synaptic pattern of C1q immunoreactivity in the brain was not observed in adult rodent brain sections, suggesting that C1q is localized to synapses in developing, but not adult brain. This synaptic pattern of C1q immunoreactivity was not detected when the same antibodies were used to stain brain sections prepared from C1q A-deficient mice, or after preadsorbing C1q antibodies with purified C1q protein (FIG. 9B).

C1q is Required for Normal Retinogeniculate Refinement.

To determine whether C1q play a functional role in developmental synapse elimination in vivo, we focused on the development of the retino-geniculate synapse. Using a combination of neuroanatomical and electrophysiological techniques, we investigated synaptic refinement and synapse elimination in the dLGN of mice that lack the A chain of C1q (C1q KO). These mice have no gross neuroanatomical or behavioral defects, despite their inability to express functional C1q protein, or to activate the classical complement cascade.

To visualize the pattern of retinogeniculate projections, we performed anterograde tracing of RGC afferents by injecting the β subunit of cholera toxin conjugated to Alexa 594 (CTβ-594) dye (red) and CTR-Alexa 488 (green) into respective left and right eyes of wild type and C1q KO mice at several postnatal ages (P5, P10 and P30). In the mouse LGN, eye-specific territories are established between P4-P8, such that by P10, axons from the ipsilateral eye have segregated into a small eye-specific patch in the medial dLGN. LGN inputs are further refined over the next two postnatal weeks, such that by P30, left and right eyes are completely segregated in to tight eye-specific territories, with minimal intermingling between RGC axons originating from left and right eyes.

We found that C1qA KO mice have significant defects in LGN refinement and segregation. At P10, the amount of dLGN territory occupied by contralateral retinal projections was notably larger, and in many cases, the ipsilateral projections appeared more diffuse in C1q KOs compared to wild type mice and litter mate controls (FIG. 3A, column a vs b). Consistent with these observations, the dLGN in C1q KO mice have significant defects in eye-specific segregation. We observed significant overlap between left and right eye RGC projections in the dLGN of C1q KOs (FIG. 3A, column a vs b, bottom row). These data were quantified using a well-established threshold-independent method of analysis, and indicate that C1q KOs had a significantly higher percentage of overlapping projections at all thresholds examined (Insert updated stats n=) (FIG. 3B).

Figure 10:
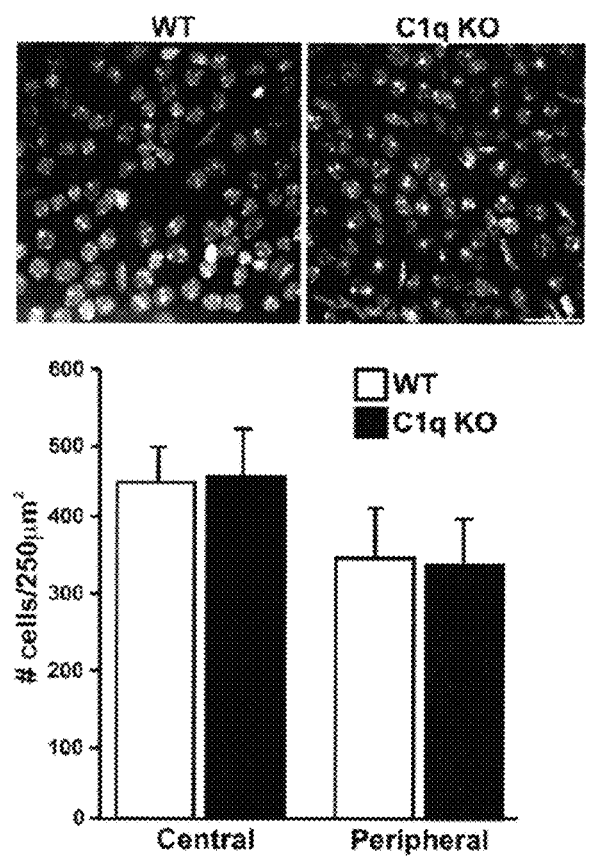
FIG. 10 illustrates whole mount retinas stained with nuclear dye, DAPI, to demonstrate that there are no significant differences in the number of cells in the peripheral or central regions of whole mount retinas in C1q KO and controls.

Surprisingly, significant segregation defects were still evident in juvenile C1q KO mice (FIG. 3B, column c vs d, bottom row). Normally, by P30, there is very little overlap between the two eyes (<3% of dLGN have overlapping projections), but as shown in FIG. 10, C1q KO mice had significant overlapping retinal projections, and these effects were threshold-independent. The phenotype at P30 was similar to that observed at P10, suggesting that many LGN neurons remain binocularly innervated long after the bulk of eye-specific segregation has occurred in the mouse (by P10). The pattern of RGC inputs to the dLGN appeared normal in C1q KO mice at P4-P5, a time point before significant segregation occurs, which suggests that refinement defects in C1q KO mice are not likely due to axonal pathfinding defects. In addition, these segregation defects can not be explained by differences in the number of RGCs in C1q KO mice. There were no significant differences in the number of cells in the peripheral or central regions of whole mount retinas in C1q KO and controls (FIG. 10).

Figure 11:
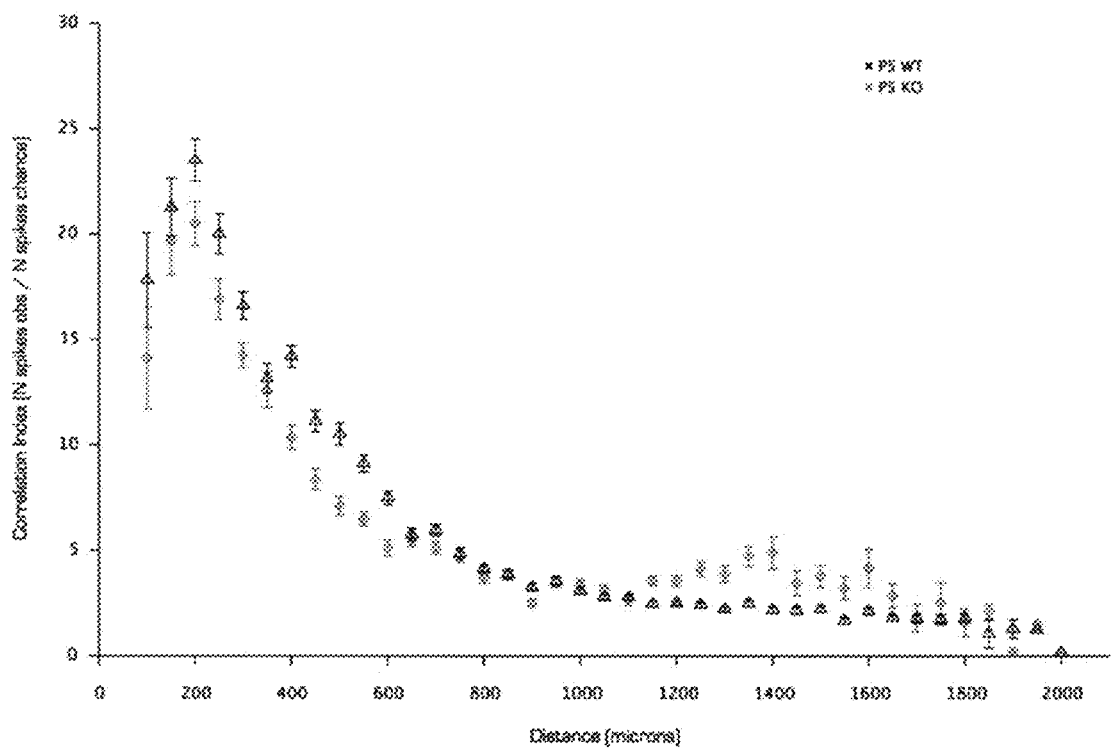
FIG. 11 illustrates by multielectrode recordings of RGC firing patterns that C1q-deficient mice have normal retinal waves. In both WT and C1qKO retinas (P5), neighboring ganglion cells are more correlated in their firing than those located at further distances from one another.
Figure 13:
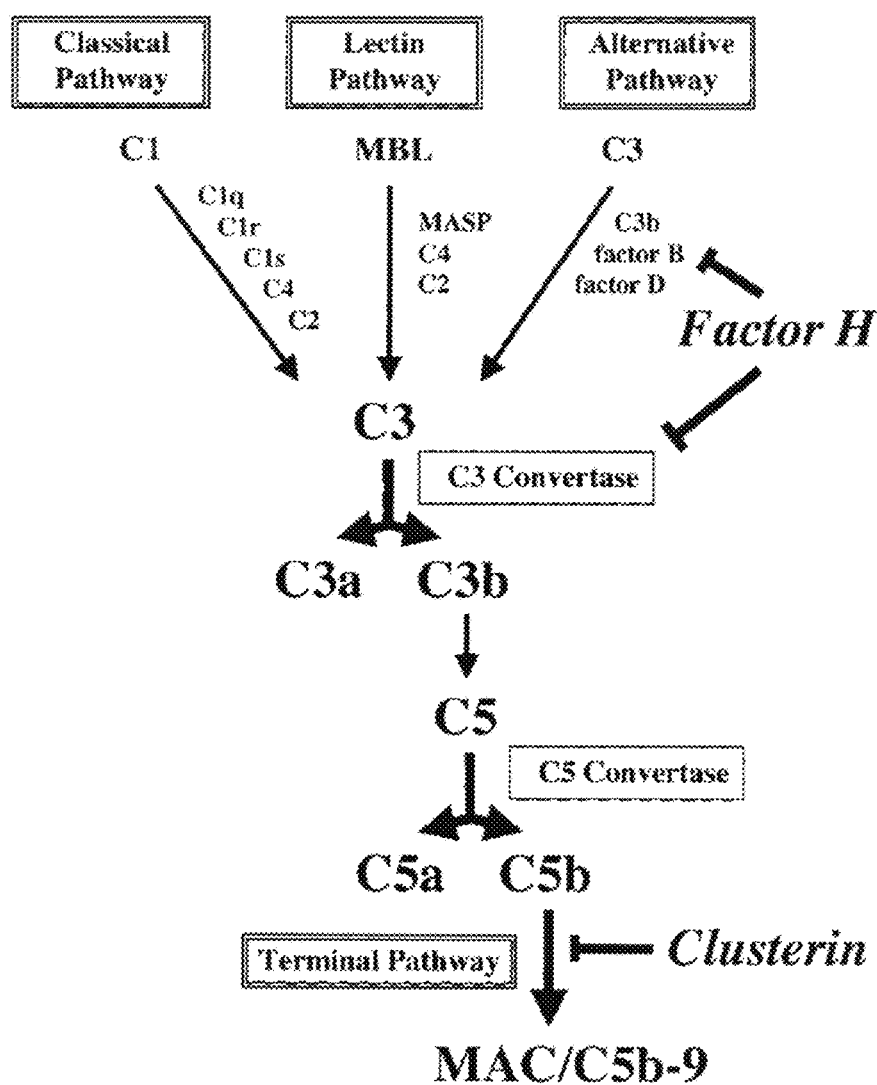
FIG. 13 illustrates the Complement pathway.
Figure 14:
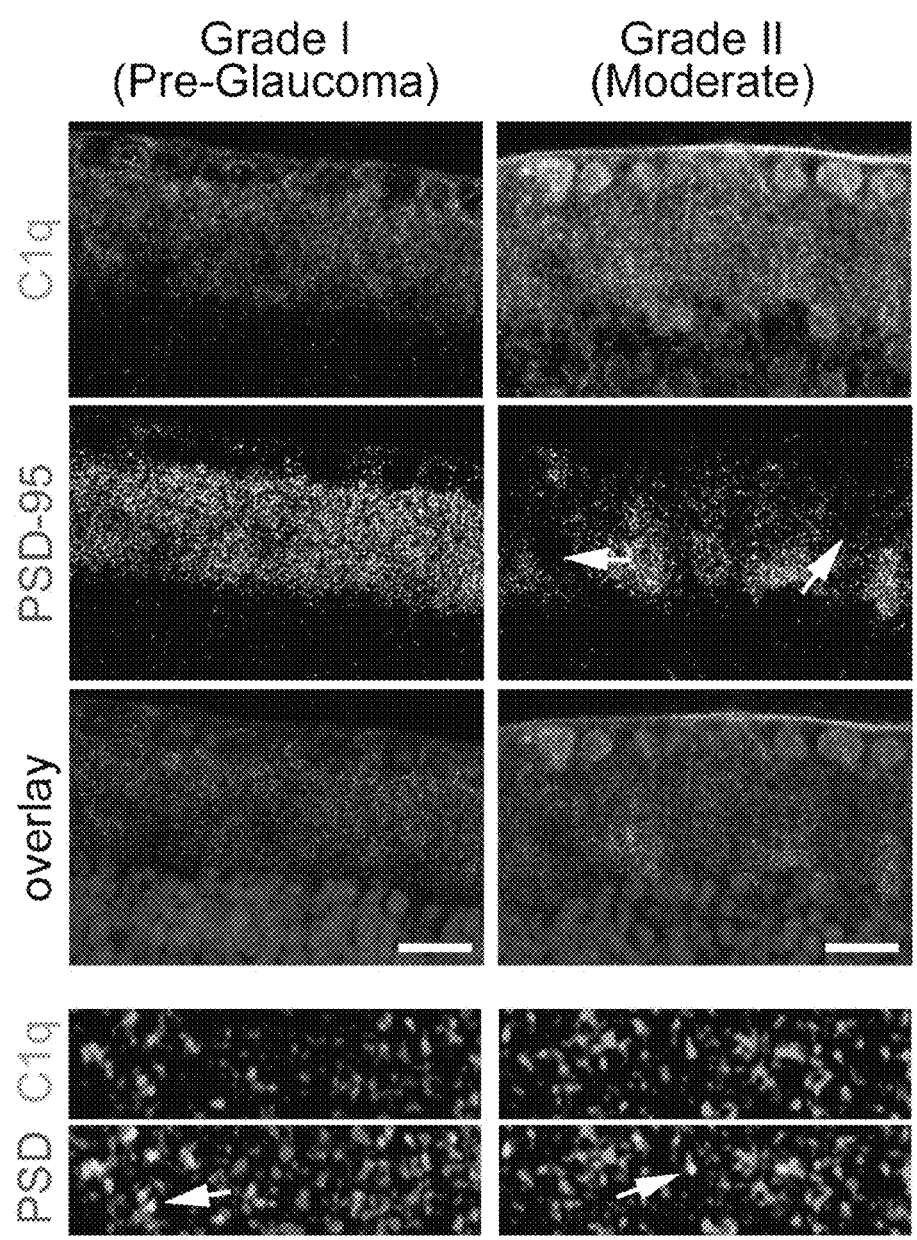
FIG. 14 demonstrates that synaptic C1q deposition followed by massive synapse loss are the two earliest pathological features in the DBA2J mouse glaucoma model FIG. 15 demonstrates that C1q deficiency is strongly neuroprotective in glaucoma. 63% of wild-type mice but only 9% of C1q null mice have moderate to severe (MOD-SEV) glaucoma.

Spontaneous retinal activity has been shown to drive eye specific segregation in several species, including mouse. Retinal waves are composed of bursts of action potentials that correlate the firing of neighboring RGCs, while the firing of more distant RGC is less correlated. In order to be sure that the segregation defects we measured in C1q KOs were not secondary to effects of abnormal retinal activity in C1qKO mice, we measured retinal waves in retinas dissected from P5 C1qKOs and age matched wild type controls. Multielectrode recordings of RGC firing patterns clearly indicate that C1q-deficient mice have normal retinal waves. In both WT and C1qKO retinas, neighboring ganglion cells are more correlated in their firing than those located at further distances from one another (FIG. 11).

LGN Neurons Remain Multiply Innervated in C1q KO Mice.

The segregation of retinal axons into eye-specific territories is a well-established assay for studying developmental synapse refinement, but synapse elimination also occurs in the monocular regions of the dLGN. Electrophysiological recordings of neurons in the contralateral LGN indicate that even after the bulk of RGC axons have segregated in to eye specific territories, synapse elimination continues to occur during the 2 weeks after eye opening. Initially (P4-P10), dLGN neurons are innervated by multiple (ie>10) RGC axons, but by the fourth week of postnatal development, each dLGN neurons receive stable inputs from 1-2 RGC axons.

Figure 4:
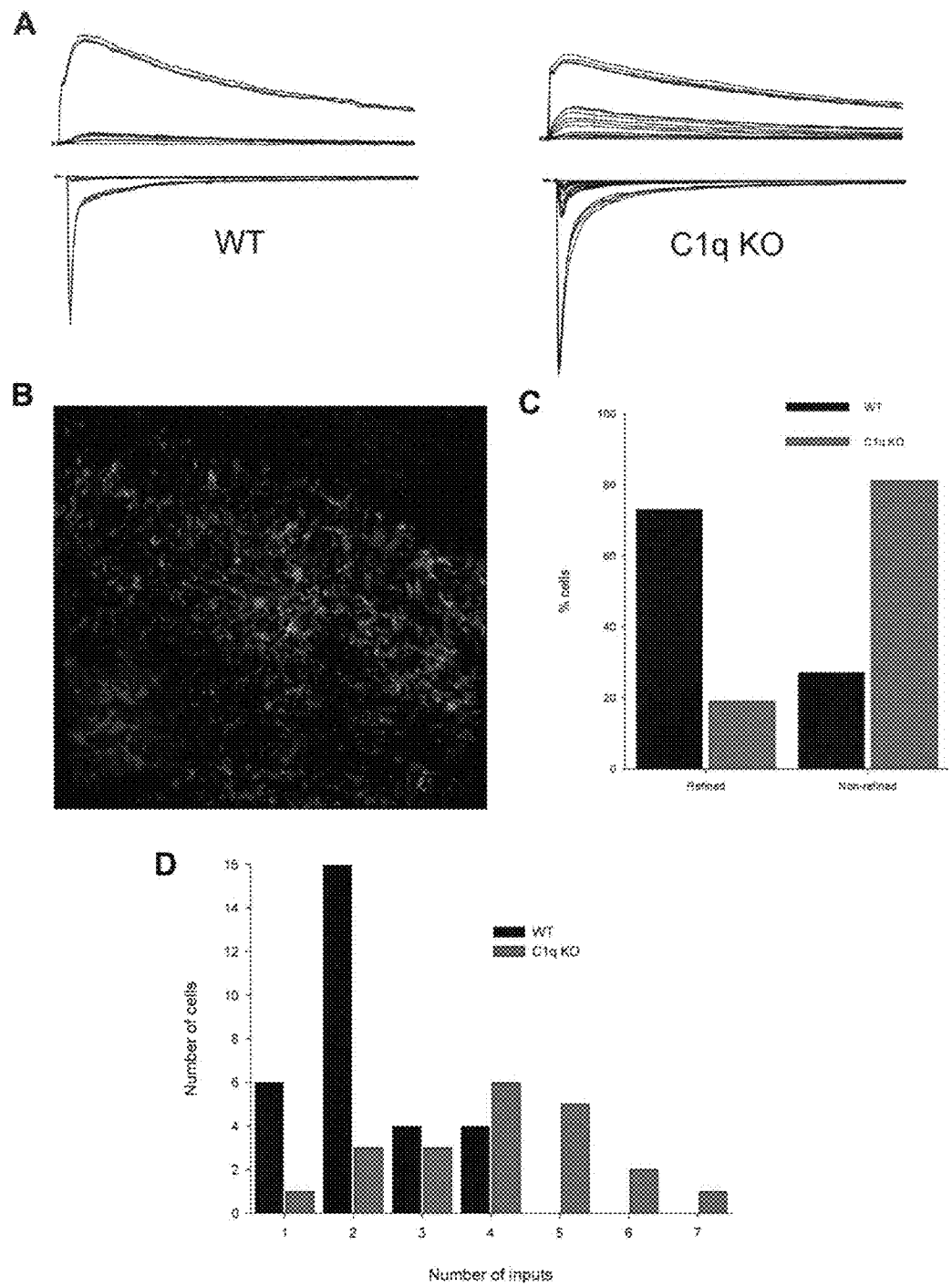
FIG. 4 demonstrates that LGN neurons remain multiply-innervated in C1q-deficient mice. A. Representative traces are of single LGN neurons recorded from a WT and C1q KO mouse. Superposition of the peaks of the rapid inward current (AMPAR, −70 mV), and slower decaying outward current (NMDAR, +40 mV) represent the recruitment of individual axons. B. Recordings from LGN neurons of P30 mice in acute parasagittal brain slices. The optic tract was stimulated in small incremental intensity steps, and measured the amplitude of evoked responses in LGN neurons (red) in the contralateral region adjacent to the optic tract in C1q KOs and age matched controls. CTβ labeled contralateral retinal projections are shown in green, and ipsilateral projections are in blue. C. 81% of the cells recorded were classified as unrefined (greater than 2 inputs) compared to 27% in age matched wild type controls (C1q KO n=21, WT n=30 cells, p<0.001). D. Summary of response properties of control and C1q KO LGN neurons. C1q KOs remain multiply-innervated (average of 4±0.3 inputs, n=21) compared to age-matched WT controls (average of 2.2±0.2 inputs, n=30, p<0.001).

In order to test directly whether C1q KO fail to undergo this form of developmental synapse elimination, we studied the retinogeniculate synapses of P26-P33 C1q KO mice in acute parasagittal brain slices. We stimulated the optic tract in small incremental intensity steps, and measured the amplitude of evoked responses in LGN neurons in the contralateral region adjacent to the optic tract in C1q KOs and age matched controls (red neurons shown in FIG. 4, B). Representative traces shown in FIG. 4A are of single LGN neurons recorded from a WT and C1q KO mouse. The peaks of the rapid inward current (AMPAR, −70 mV), and slower decaying outward current (NMDAR, +40 mV) represent the recruitment of individual axons. We found that C1q KOs remain multiply-innervated (average of 4±0.3 inputs, n=21) compared to age-matched WT controls (average of 2.2±0.2 inputs, n=30, $p<0.001$). Although there was no significant difference in the maximum amplitude of AMPA or NMDA responses between C1q KO and WTs, the average amplitude of evoked responses were significantly reduced in C1q KOs (data not shown). We observed many small amplitude responses in C1q KOs (as shown in FIG. 4A) in approximately 80% of the slices obtained from C1q KO mice. As summarized in FIG. 11C, 81% of the cells recorded were classified as unrefined (greater than 2 inputs) compared to 27% in age matched wild type controls (C1q KO n=21, WT n=30 cells, $p<0.001$).

Taken together, these experiments indicate that C1q is necessary for the structural and functional elimination inappropriate synaptic connections in the developing retinogeniculate pathway.

Role of the Complement Cascade in Developmental Synapse Elimination.

C1q is the initiating protein of the classical complement cascade. Activated C1q undergoes a conformational change to activate a sequential cascade of downstream proteases, including the major complement protein, C3. Activated C3 fragments (C3b, iC3b) can directly opsonize dead cells and pathogens for phagocytosis, much like C1q. Alternatively, C3-activation can activate downstream complement proteins C5-C9 to eliminate unwanted cells via the formation of a membrane attack complex, which permeabilizes cell and lyses the cell.

Figure 5:
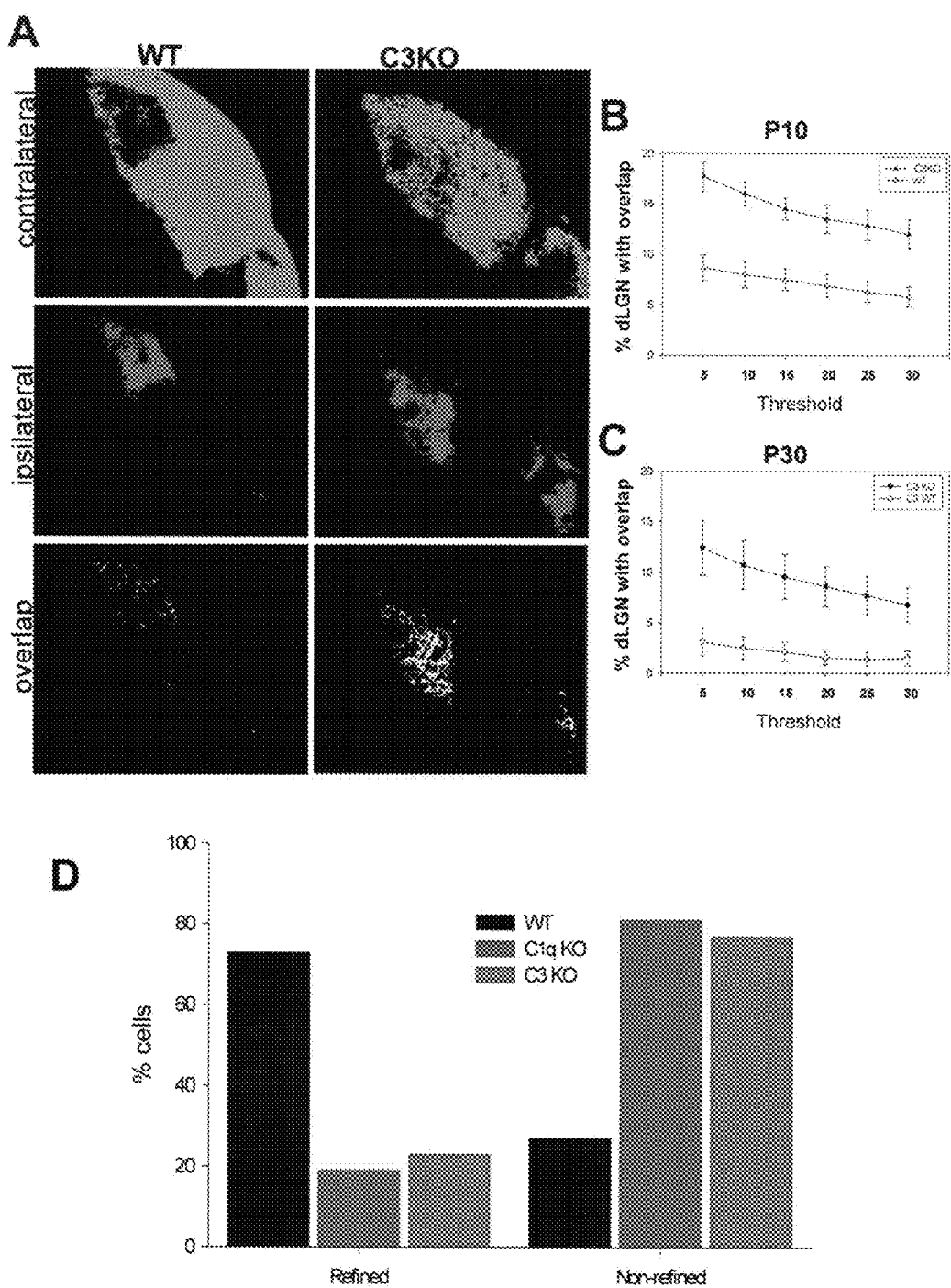
FIG. 5 illustrates that mice deficient in C3 also have defects in synapse elimination. A. Anterograde tracing experiments showing C3 KO mice at P30 exhibit significant overlap between RGC axons from left and right eyes (yellow) compared to littermate WT controls. B Quantification of the percentage of dLGN receiving overlapping inputs from the ipsilateral eye in C1q KO versus WT controls at P10 (B) and P30 (C). C1q KO mice exhibit significantly more overlap than WT mice, regardless of threshold. D. Electrophysiological recordings of P30-34 dLGN neurons indicate that LGN neurons recorded from C3 KO mice remain multi-innervated (non refined) and had similar response properties to C1q KO mice.

To determine whether C3 is necessary for synapse elimination, we obtained mice deficient in complement protein C3 to investigate whether absence of C3 mimics the phenotype we observed in the LGNs of C1q-deficient mice. We performed similar anterograde tracing experiments and electrophysiological recording of retino-geniculate synapses in C3KO mice and age matched controls as described above. Consistent with our hypothesis, C3 KO mice have defects in LGN segregation and synapse elimination that closely mimic the C1qKO phenotype. C3 KO mice had significant defects in eye-specific segregation, both at P10 and P30 (FIG. 5 A-C). Quantification of the percentage of dLGN occupied by overlapping retinal axons from both eyes indicate that C3KO mice had significantly more overlap than age matched and littermate controls. Electrophysiological recordings of P30-34 dLGN neurons indicate that LGN neurons recorded from C3 KO mice remain multi-innervated and had similar response properties to C1q KO mice (FIG. 5D). Together, these findings provide supporting evidence that the classical complement cascade mediates normal developmental synapse elimination.

Complement C3 is Expressed at Developing CNS Synapses.

Is C3 activated and localized to synapses in the postnatal brain? Complement activation has been shown to occur in the brain after injury, stroke, and inflammation, but the expression and localization during normal postnatal development has not been previously examined. We performed immunostaining experiments in cryosections of perfused postnatal mouse and rat brain using polyclonal antibodies against rat C3. We found that C3 protein is expressed in postnatal rodent brain and cortex, but C3 protein was not detected in the adult brain (FIG. 6A). Importantly, double immunohistochemistry with the synaptic antibody SV2, revealed that many C3-positive puncta co-localized with synaptic puncta (FIG. 6A). Immunoreactivity was specific for C3, as C3-specific antibodies failed to stain brain sections prepared from C3-deficient mice.

Western blot analysis of protein lysates prepared from perfused, developing cortex provide direct evidence that C3 is activated in the developing brain (FIG. 7B). When native C3 is cleaved, activated C3 fragments (43 kD) can be detected by SDS-PAGE and western blot analyses using polyclonal antibodies against C3. As shown in FIG. 7B, we observed a clear band for iC3b in postnatal cortex, and C3b levels were significantly down-regulated by P30. Together these data provide evidence that the complement cascade is activated during the period of synaptic pruning in the brain.

Complement-Deficient Mice have More Synapses.

Figure 8:
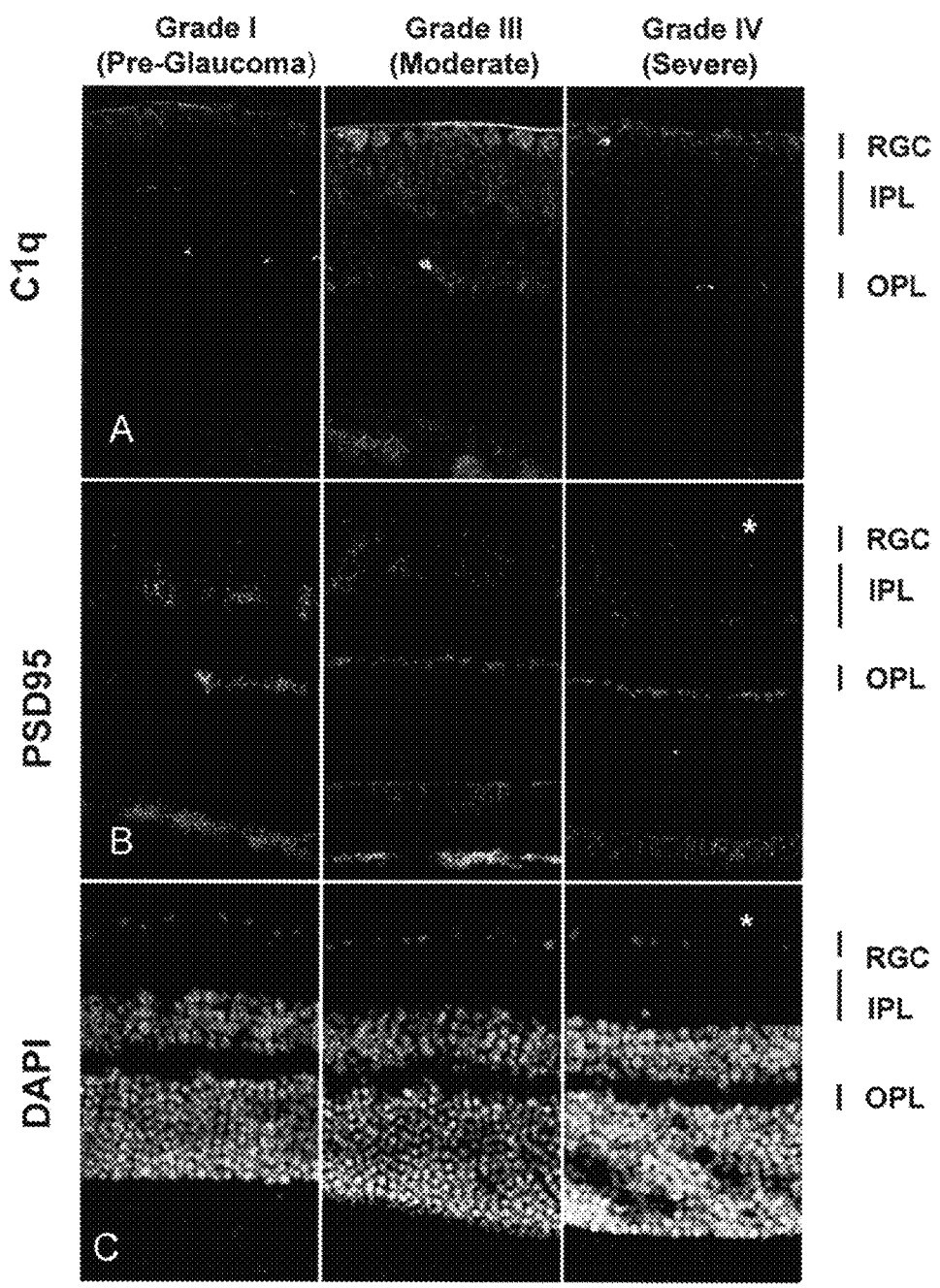
FIG. 8 demonstrates that C1q is localized to synapse in early stages of glaucoma. Immohistochemistry of A. C1q and the postsynaptic protein, B. PSD95 in the RGC and C. synaptic layers of retinas from DBA/2J mice various stages of disease (pre-glaucoma, early, moderate and late stage). Punctate C1q immunoreactivity (top row) in the IPL of retinas from DBA/2J mice with moderate (Grade III, 6-12 months) glaucoma and before significant RGC or synapse cell loss C1q staining is present in the IPL, but less pronounced in retinas collected from retinas with severe glaucoma and RGC death (as seen in DAPI staining of RGC cell bodies, bottom row).

An increase in synapse number would provide further evidence that complement proteins are required for synapse elimination. To address this question, we compared the relative intensity of synaptic staining the LGNs and superior colliculi of C1q KO mice and littermate controls using several synaptic antibodies including vGLUT2, a vesicular glutamate transporter that is selectively expressed by retinal ganglion cells. As shown in FIG. 8, we found a general increase in the intensity of vGLUT2 staining in both the superior colliculi (SC) and dLGN of C1q KO mice (FIG. 8A, B). Sections from P16 C1qKO and controls were processed and immunostained in parallel, and all images were collected at identical cameral exposures. In addition, high resolution confocal microscopy imaging revealed a higher density of PSD95 puncta in dLGNs of P16 C1q KO mice compared to littermate controls. (FIG. 8C).

C1q is Localized to Synapses in Early Stages of Neurodegenerative Disease.

Could synapse loss at early stages of neurodegenerative disease involve a re-activation of developmental synapse elimination mediated by the complement cascade? Complement expression and activation are known to be significantly enhanced following brain injury and in various neurodegenerative diseases, such as Alzheimer's Disease (AD). In many cases, astrocytes, and microglia become reactive and could therefore re-express the signal that induces C1q expression in developing neurons. For example, AD is caused by a massive degeneration of synapses, and it has become increasingly clear that synapse loss occurs long before neuropathology and clinical symptoms in AD brains. C1q protein is 10- to 80-fold up-regulated in AD brain, and amyloid β-peptide (Aβ) is a powerful activator of C1q.

We investigated this question using a well characterized mouse model of glaucoma. The glaucomas are neurodegenerative diseases involving death of retinal ganglion cells and optic nerve head excavation that is often associated with elevated intraocular pressure (IOP). DBA/2J mice have been shown to exhibit an age-related progressive glaucoma. The period when mice have elevated IOP extends from 6 months to 16 months, with 8-9 months representing an important transition to high IOP for many mice. Optic nerve degeneration follows IOP elevation, with the majority of optic nerves being severely damaged by 12 months of age.

Could C1q-dependent synapse elimination trigger synaptic loss before RGC death and neurodegeneration? To address this question, we looked at the timing and localization of C1q immunoreactivity in the RGC and synaptic layers of retinas of DBA/2J and control mice at various stages of disease (pre-glaucoma, early, moderate and late stage). As shown in FIG. 15, we found punctate C1q immunoreactivity in the IPL of retinas from DBA/2J mice with moderate (Grade III, 6-12 months) glaucoma. At this stage, there is no significant RGC or synapse cell loss, as indicated by PSD-95 staining in the IPL. C1q staining is present in the IPL, but less pronounced in retinas collected from retinas with severe glaucoma (Severe, 9-12 months). At this stage there is significant RGC and death and degeneration of retinal axons. Importantly, C1q immunoreactivity was not observed in the IPL of young DBA mice (1-2 months), or in retinas obtained from a control strain (2-12 months of age) that lacked the glaucoma gene. Together our findings indicate that C1q is localized to synapses in the IPL before significant synapse loss and RGC death, which supports the notion that complement is mediating synapse loss in early stages of disease.

Example 2

The decline of cognitive function is one of the greatest health threats for the aging population. It has been widely accepted that it is primarily loss of synaptic connections, rather than loss of neurons per se, that is responsible for age-associated cognitive impairment in otherwise healthy individuals. In rats, these aging changes are particularly prominent in the dentate gyrus where decreased synapses, decreased EPSPs, decreased LTP, and spatial memory deficits occur (Morrell, PNAS, 1986; Barnes, J. Comp. Physiol. Psych. 1979; Lynch, J. Gerontology, 1977).

As demonstrated in example 1 above, a vast loss of synapses occurs normally within the developing brain as neural circuits are sculpted. This developmental CNS synapse elimination is mediated by complement component C1. The known role of C1q, when activated, is to trigger the onset of the classical complement cascade, causing destruction and elimination of pathogens, apoptotic cells and debris.

Figure 16:
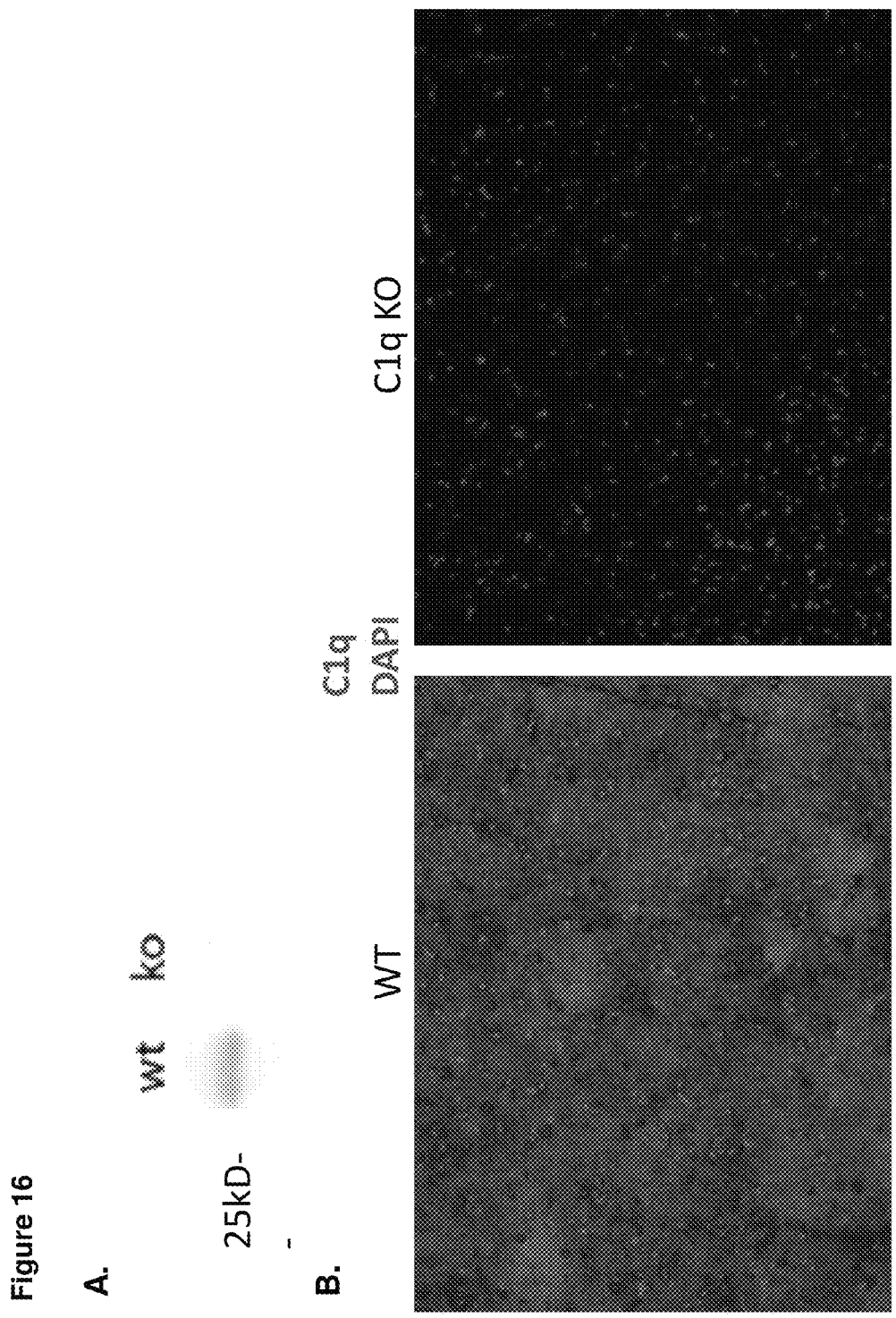
FIG. 16 demonstrates that rabbit anti-Mouse C1q antibodies are specific. (A) Western blot of CNS tissue from wild type and C1q null animals with C1q polyclonal antibodies. (B) Immunostaining of CNS tissue with C1q monoclonal antibodies.

To investigate whether C1q plays a role in synapse loss in aging, a rabbit monoclonal antibody was generated to C1q and used to examine the detailed expression pattern for C1q protein in the adult and aging rodent CNS. Rabbits were immunized with a C1q protein purified from mouse serum. 5 hybridomas were generated, which produced 5 mAbs, all of which showed identical and specific immunostaining signals (see, e.g. FIG. 16).

Figure 17:
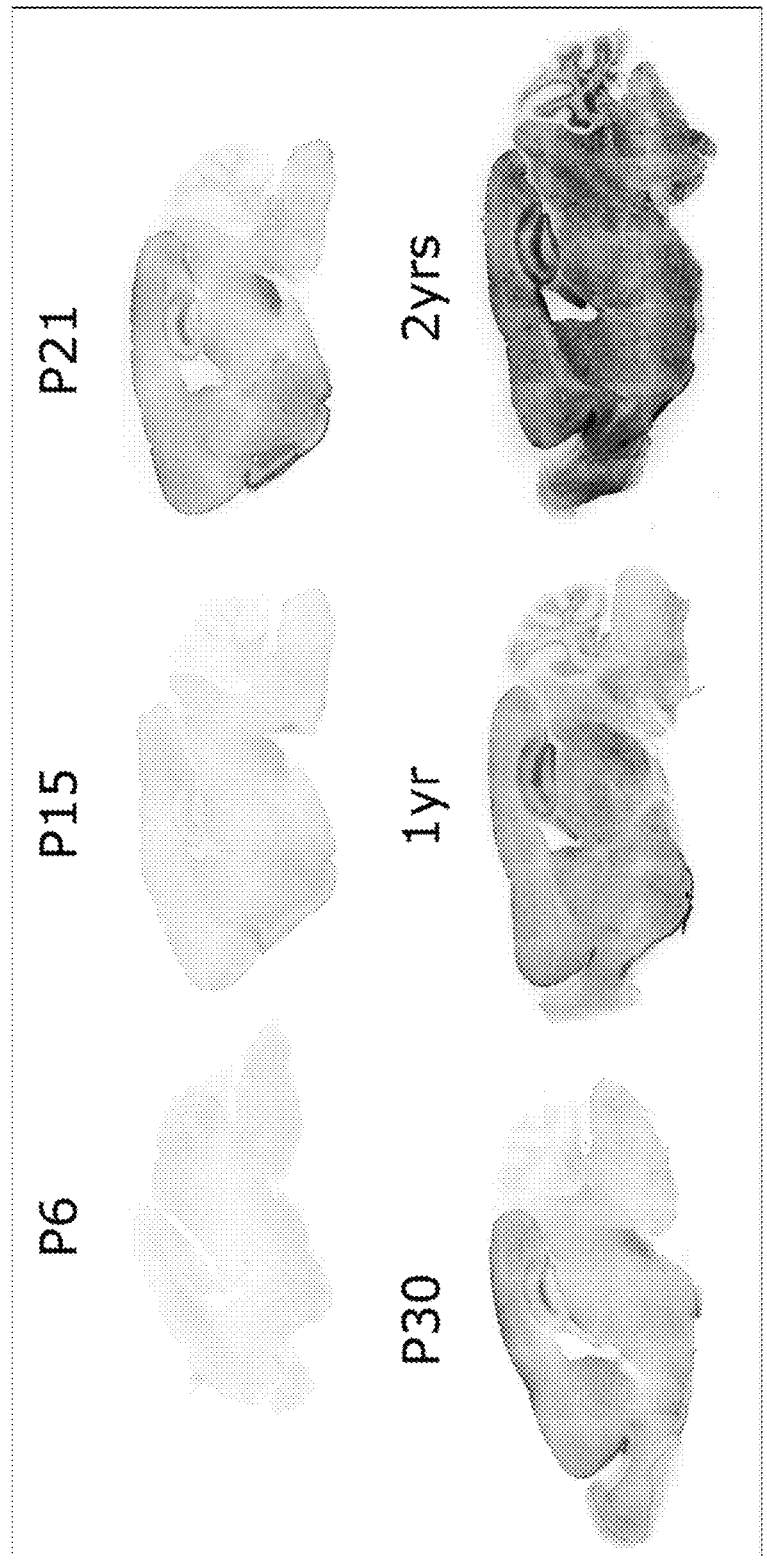
FIG. 17 illustrates that C1q immunoreactivity increases in the aging mouse brain. 5× mosaic scan of C57BL/6 wild type mice.
Figure 18:
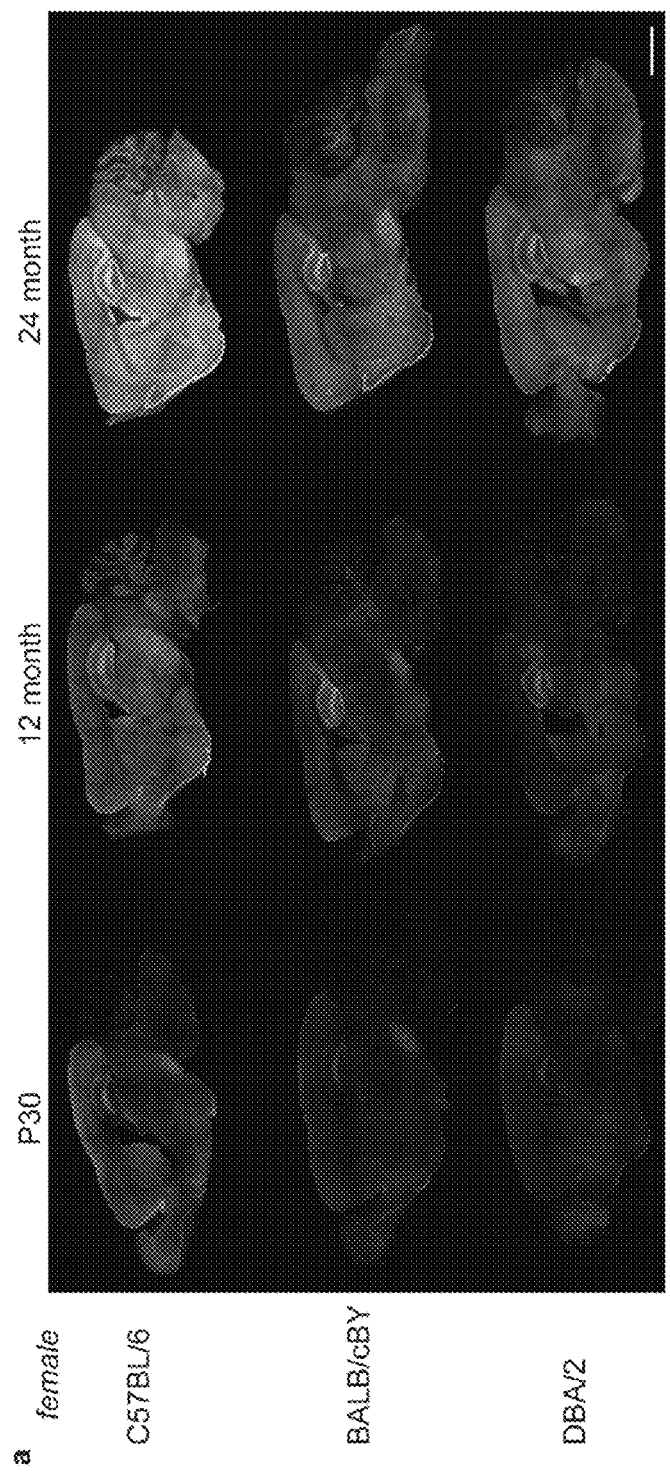
FIG. 18 illustrates C1q protein expression in the aging mouse CNS. a, b, Time-course immunohistochemistry with slices from perfused brains from three different mouse strains confirmed that C1q protein levels dramatically increase in an identical pattern with age throughout the brain, independent of mouse strain and sex (a, female; b, male). c, Western blot analyses of mouse whole-brain homogenates (perfused mice) with two independent antibodies, either recognizing the C1q-A and -B chains or the C1q-C chain, confirmed the dramatic age-dependent increase of C1q protein in the mouse brain, when compared to the βTubulin loading controls. Note that all available anti-C1q antibodies detect unspecific bands in Western blot experiments of mouse brain homogenates. The one unspecific band directly above the C1q-specific band (arrow) varies in visibility between experiments. d, Western blot analysis of mouse whole-brain homogenates (perfused mice) confirmed that C1q protein similarly increases with aging in the brains of male and female mice, when compared to the βTubulin loading controls. e, This sex-independent increase of C1q protein (arrow head) with age was also confirmed by Western blotting to be mouse-strain independent, when compared to the βTubulin loading controls (arrow: additional, unspecific band detected by the antibody used). f, The increase with age in the brain is C1q-protein specific as other CNS proteins, like PSD-95, do not show a similar regulation, when compared to the βTubulin loading controls. g, Like in the brain, C1q protein increases with age in spinal cord extracts from perfused mice, when compared to the βTubulin loading controls. h, C1q-protein levels in the retina are moderate at young postnatal ages but, n strong contrast to brain and spinal cord, decrease to below detection levels in adulthood and aging, when compared to the βTubulin loading controls. P—postnatal day; m—month; Scale bars: 2 mm.
Figure 18:
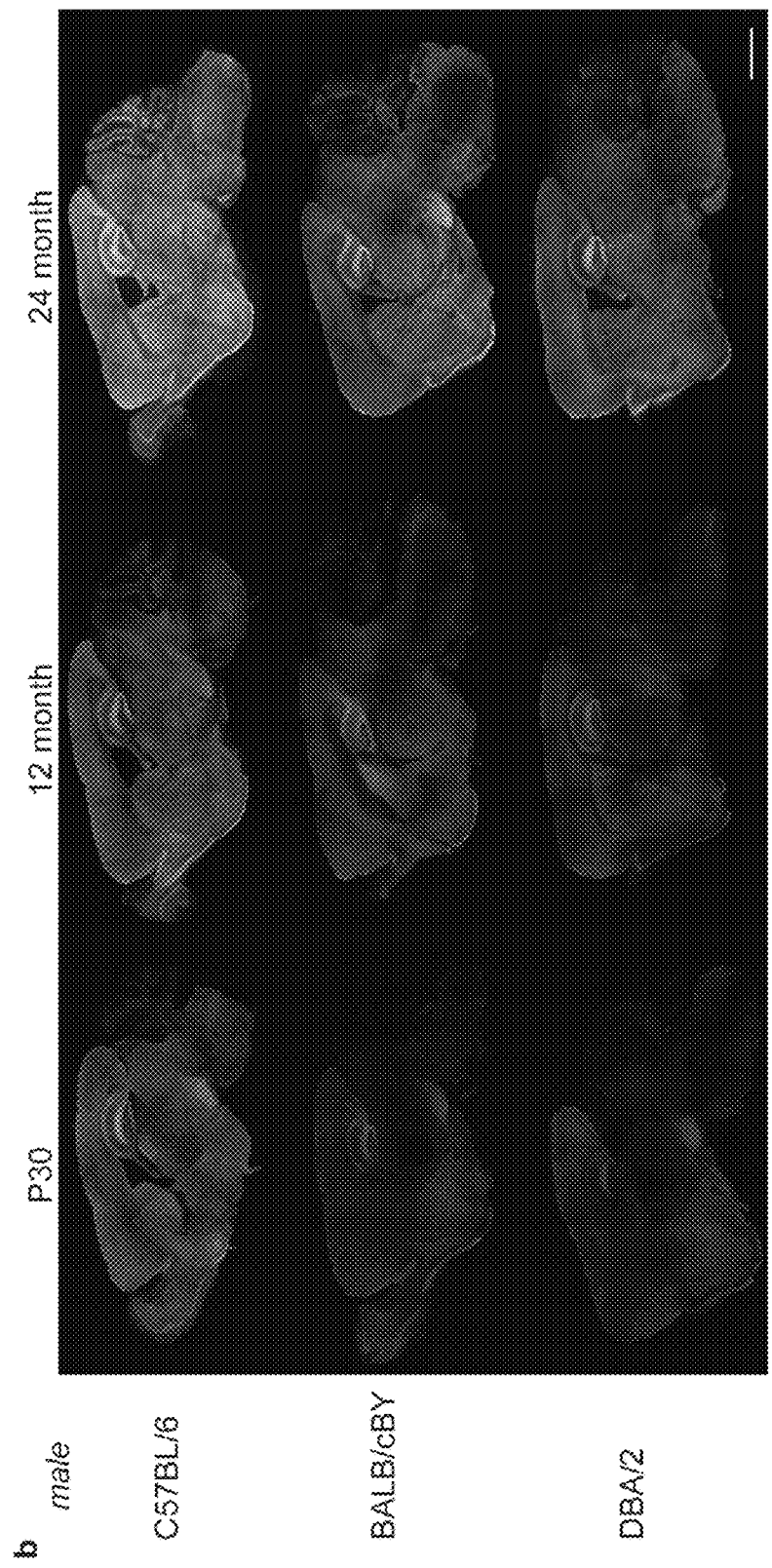
Figure 18:
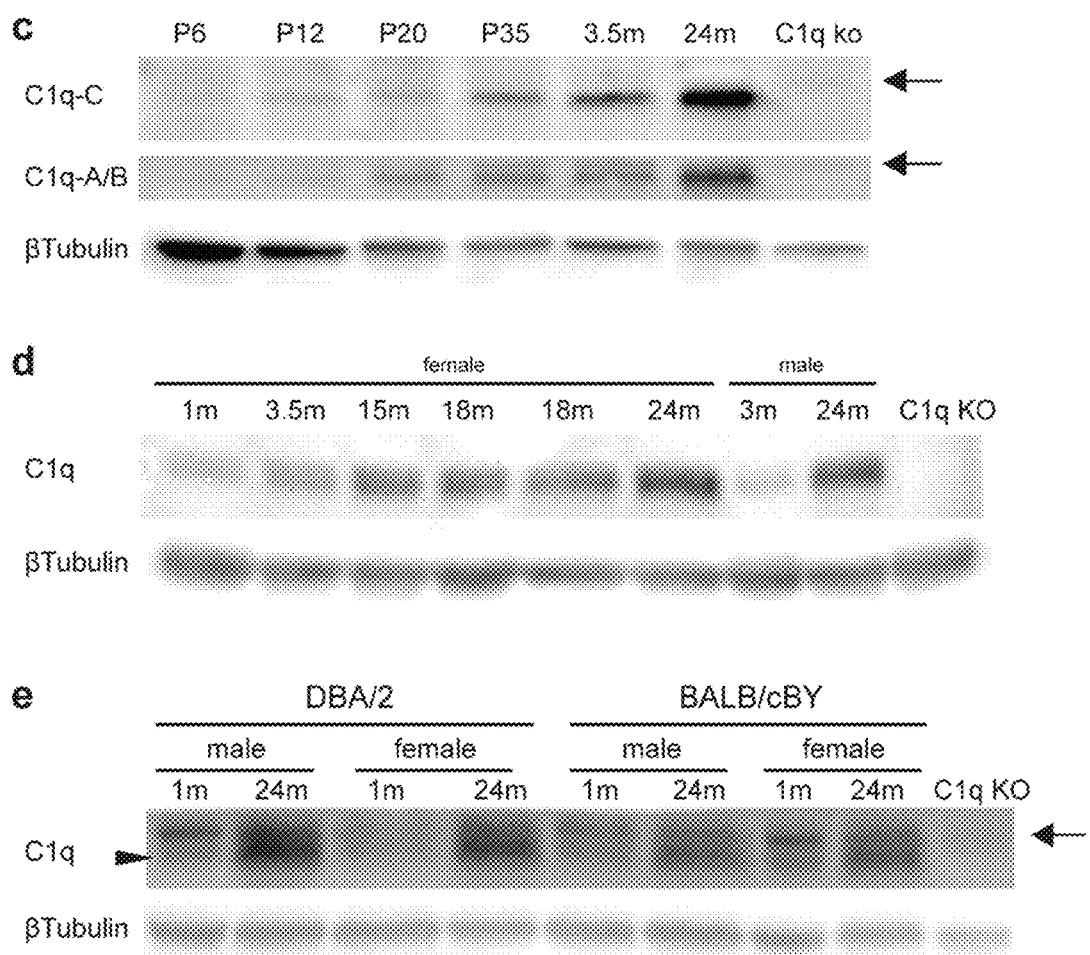
Figure 21:
FIG. 21 illustrates C1q immunoreactivity in the P6 mouse brain.

We discovered that C1q protein has an intriguing expression pattern in the adult, suggesting synaptic functions for C1q and complement in the healthy mature CNS. C1q protein levels dramatically increase in the aging brain (FIG. 17). This expression pattern is detected in C57BL/6, Swiss Webster, DBA/2, BALB/c mouse (FIG. 18A, 18B) and in both male (FIG. 18A) and female (FIG. 18B) tissue, indicating that it is strain and sex independent. The most dramatic increase can be observed by comparing a postnatal day 6 (P6) mouse brain (FIG. 21) with that of a 24 month old mouse (FIG. 22).

Figure 23:
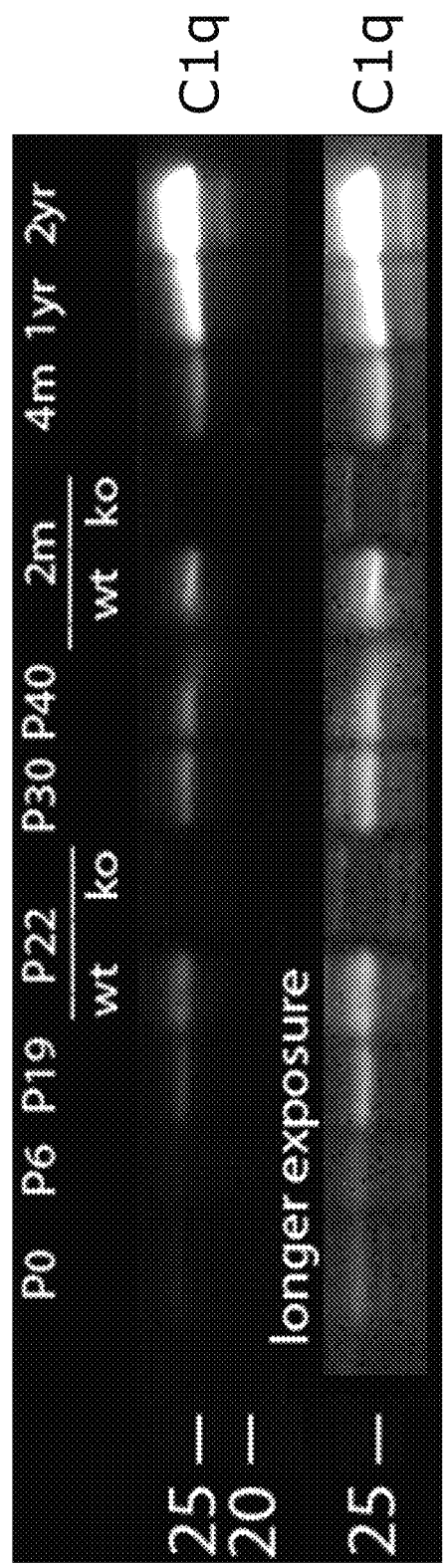
FIG. 23 demonstrates that C1q protein levels dramatically increase in the aging mouse brain. A Western blot of brain homogenates is shown.
Figure 25:
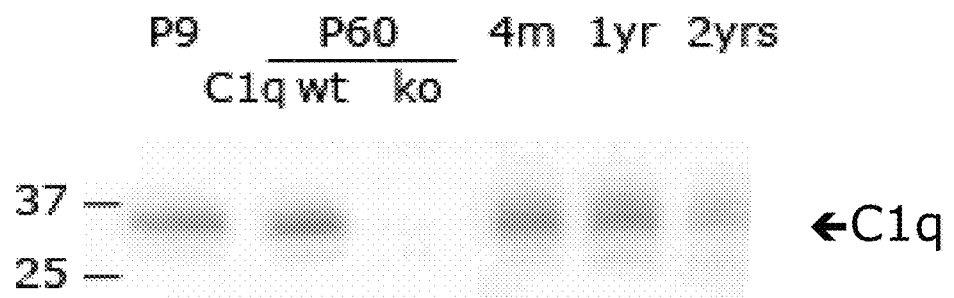
FIG. 25 demonstrates that C1q protein levels do not increase in aging mouse serum.
Figure 26:
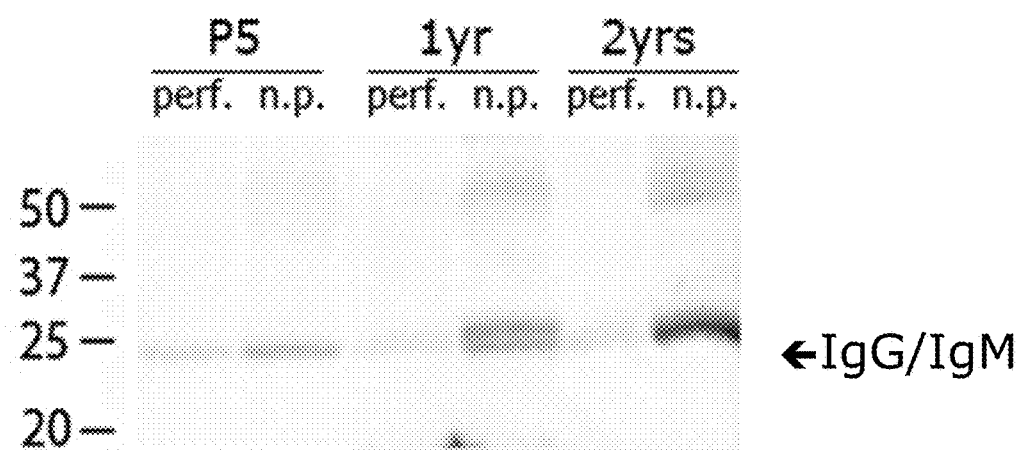
FIG. 26 demonstrates that the increase in CNS C1q protein levels cannot be explained by age-dependent leakage of the blood-brain barrier. perf, perfused. n.p., not perfused.

Western blots of C1q levels in brain homogenates likewise demonstrate a dramatic increase of C1q protein as the brain ages (FIGS. 23 and 24). C1q protein levels do not increase in aging mouse serum (FIG. 25). Consistent with this, an analysis of perfused and non-perfused tissue from differently aged mice indicates that the increase in CNS C1q protein levels cannot be explained by an age-dependent leakage of the Blood-Brain Barrier (FIG. 26).

Figure 22:
FIG. 22 provides a characterization of C1q-positive patches in the mouse brain. a, Representative immunohistochemistry image of a two year old mouse brain slice (perfused animal), stained with the rabbit anti-mouse C1q monoclonal antibody. C1q-specific signals were detected in virtually all synaptic layers of the mouse brain, except the molecular layer of the Cerebellum (white arrow head). C1q-positive signals were particularly strong in the Hippocampus (blue arrow head), the Piriform Cortex (yellow arrow head) and the Substantia Nigra (red arrow head). C1q-positive patches appeared throughout the brain (arrows). b, c, Higher magnification images depicting the variability in appearance of these C1q-positive patches (arrows). d, e, Confocal microscopy revealed that the C1q-positive patches were neither particularly co-localizing with microglia (d, Cx3CR1-GFP labeled microglia) nor astrocytes (e, ALdH1L1-GFP labeled astrocytes) but that the C1q-positive signals appear diffuse in the neuropil around all cell types (large DAPI labeled neuronal cell bodies). f-k, Confocal microscopy co-localization analyses for C1q and the excitatory synaptic protein VGluT1 (f-h) or the inhibitory synaptic protein VGAT (i-k) revealed that the overall synaptic pattern was not altered in C1q-positive patches. Whereas C1q-immunoreactivity was increased in patch areas ($f_1$, $g_1$, $i_1$, $j_1$) over areas outside the patches (hi, $k_1$), both VGlut1 and VGAT immunoreactivities were unchanged inside or outside the C1q-positive patches (inside patch area: g2, VGluT1 and j2, VGAT; outside patch area: $h_2$, VGluT1 and $k_2$, VGAT). Scale bars: a, 1 mm; b, 250 μm; c, 100 μm; d, e, f, l, 50 μm; g, h, j, k, 5 μm.
Figure 22:
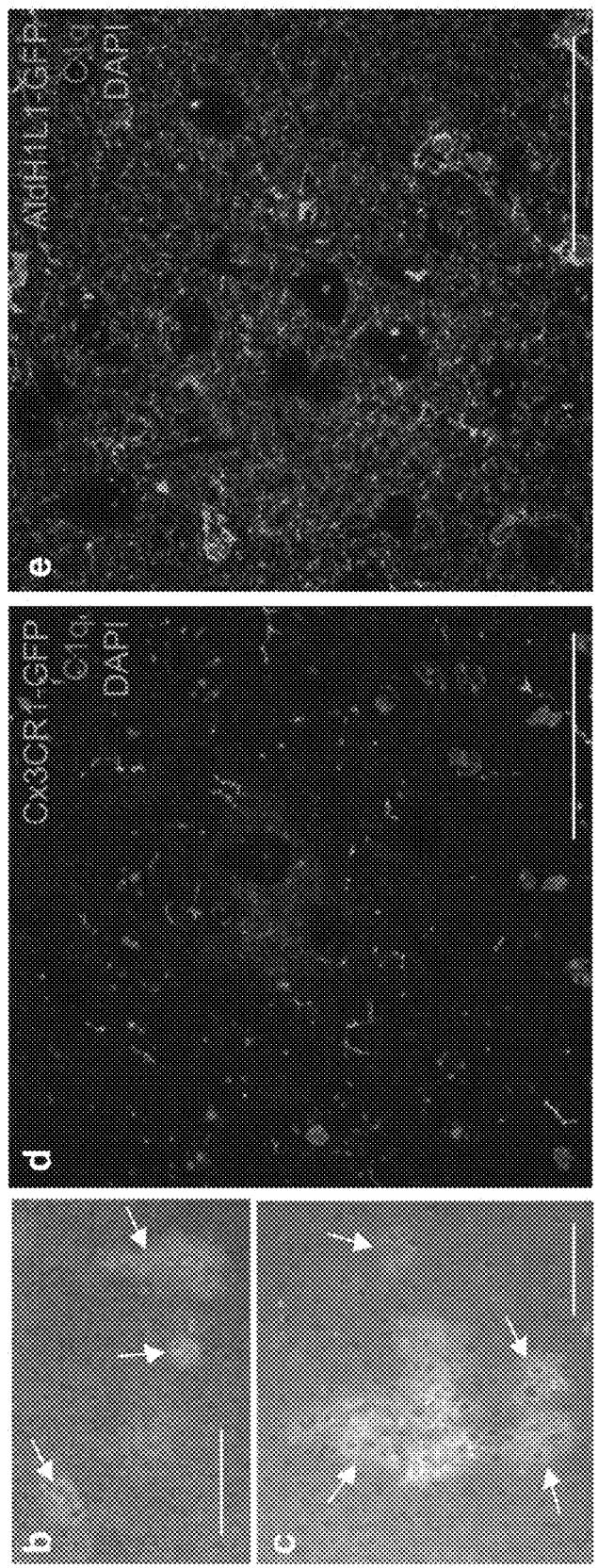
Figure 22:
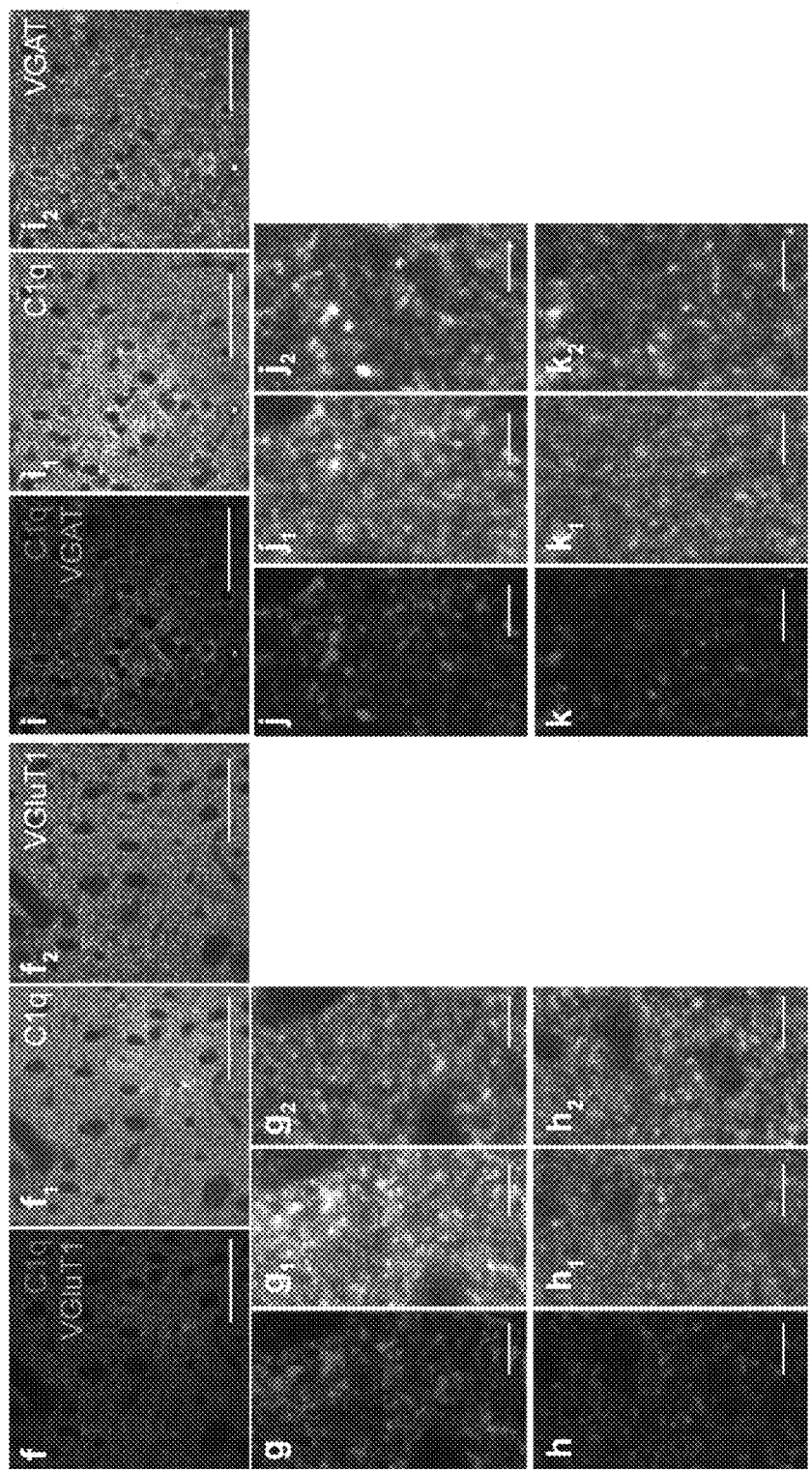

It was observed that C1q immunoreactivity forms patches in the adult brain (FIG. 22). These patches represent punctate signals of 50 to 200 uM with stronger C1q intensity compared to signals in the surrounding neuropil. They are most pronounced in cortex, thalamus, and midbrain, but, unlike amyloid plaques, are rare in hippocampus. They are thioflavin negative, indicating that they are not associated with higher microglial density or synapse loss. They can be detected in young adulthood, however, are more pronounced in middle-aged (6 months onward) and even more in aged mouse brain.

Figure 27:
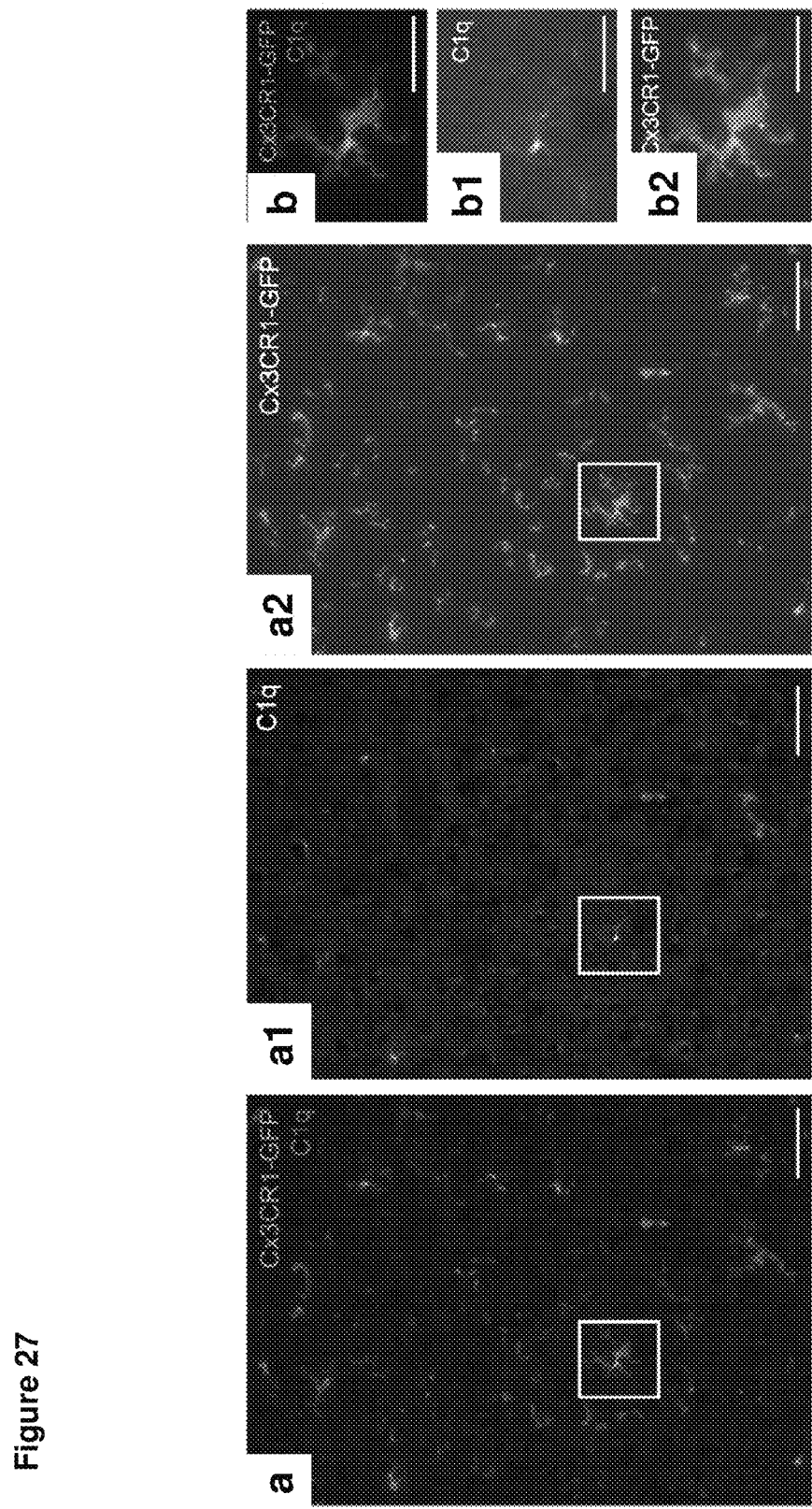
FIG. 27 demonstrates that C1q protein in the CNS is expressed by microglia at all developmental stages. a, b, Co-localization immunohistochemistry analysis confirmed that anti-C1q immunoreactivity in the perfused postnatal day six mouse brain was virtually exclusively detected in microglia, visualized by anti-GFP immunoreactivity in slices from Cx3CR1-GFP+/− mice (a and b: costaining of C1q and Cx3CR1-GFP; a1 and b1: C1q staining alone: a2 and b2: Cx3CR1-GFP staining alone; image representative for all brain regions; image location: midbrain; boxed area in a, is shown as magnified image in b). c, d, Co-localization immunohistochemistry analysis revealed that anti-C1q immunoreactivity in the perfused adult mouse brain was strongly detected in the neuropil and in all microglia (a and b: costaining of C1q and Cx3CR1-GFP; a1 and b1: C1q staining alone: a2 and b2: Cx3CR1-GFP staining alone; image representative for all brain regions; image location: midbrain; boxed area in c, is shown as magnified image in d). Scale bars: a, 50 μm; b, d, 20 μm; c, 100 μm.
Figure 27:
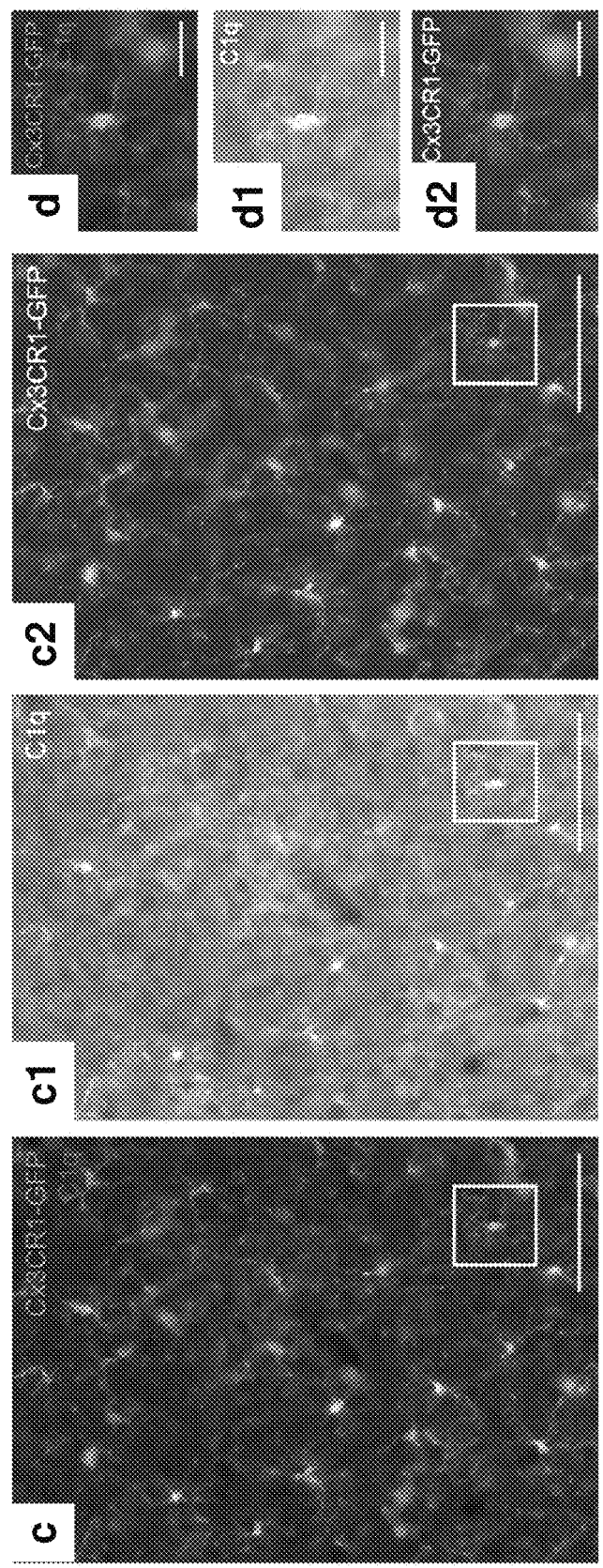
Figure 28:
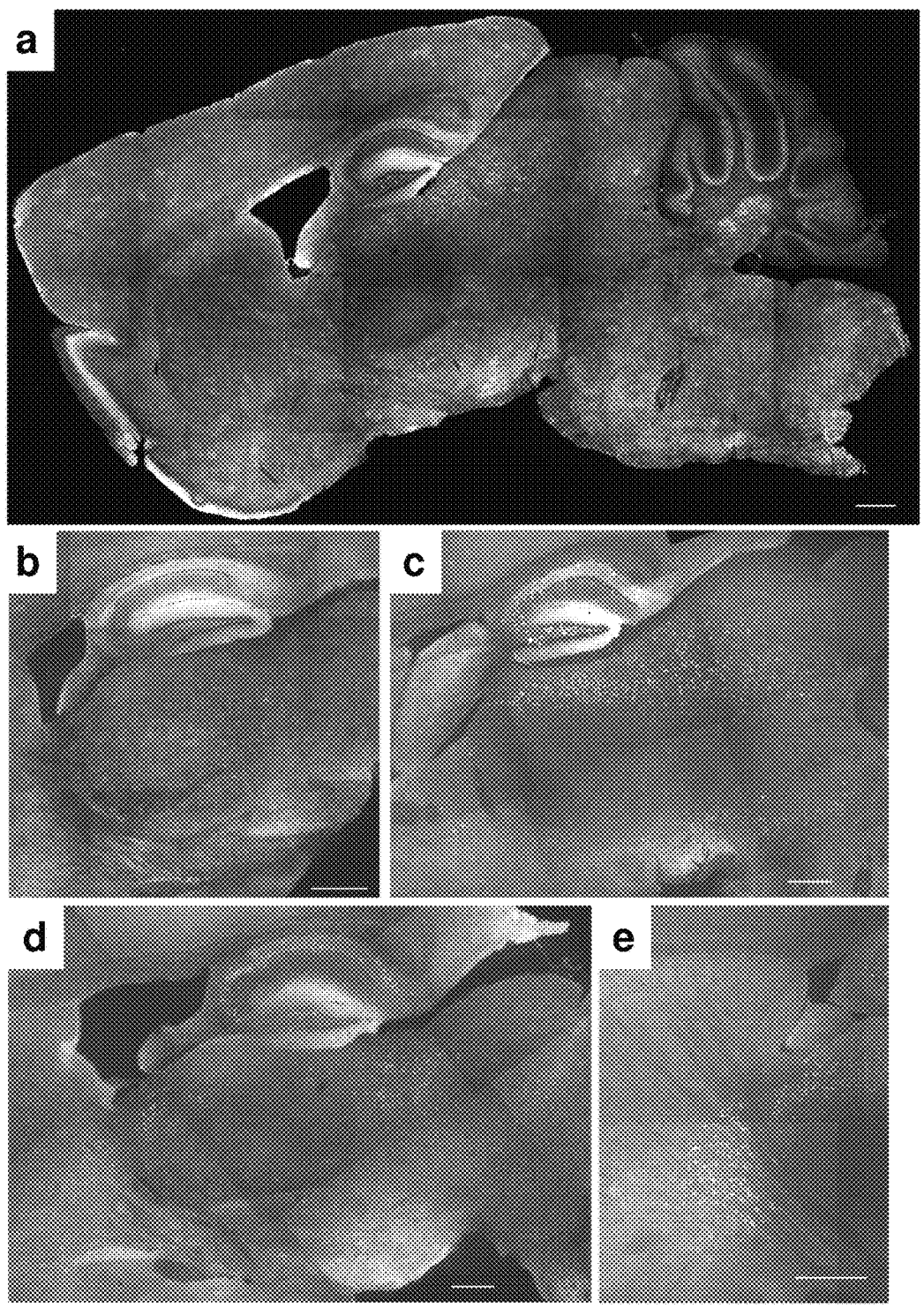
FIG. 28 demonstrates that C1q protein is detected in a subset of neurons throughout the murine brain. a, Immunohistochemistry analysis of a slice from an adult mouse brain (perfused, slightly modified processing: shortened fixation with 4% PFA and processed with a freezing, sliding microtome) enabled additional C1q-protein detection in a distinct subset of neurons in certain areas of the brain. These C1q-positive neurons were detected from about one month of age on and aging-independent thereafter. C1q-positive neurons were detected in the Hippocampus, Thalamus, Striatum and Midbrain, dependent of the location of the slices within the brain. b, Detection of C1q-positive neurons in the Hippocampus and Thalamus. c, Detection of C1q-positive neurons in the Hippocampus, Thalamus and Midbrain. d, Detection of C1q-positive neurons in the Hippocampus, Thalamus, Midbrain and Striatum. e, Detection of C1q-positive neurons in the Thalamus and Striatum (mainly Globus Pallidus). Scale bars: a-e, 500 μm.
Figure 29:
FIG. 29 demonstrates by C1q/parvalbumin co-staining that C1q immunoreactive neurons are mainly inhibitory. a, hippocampus. b, globus pallidus.
Figure 29:
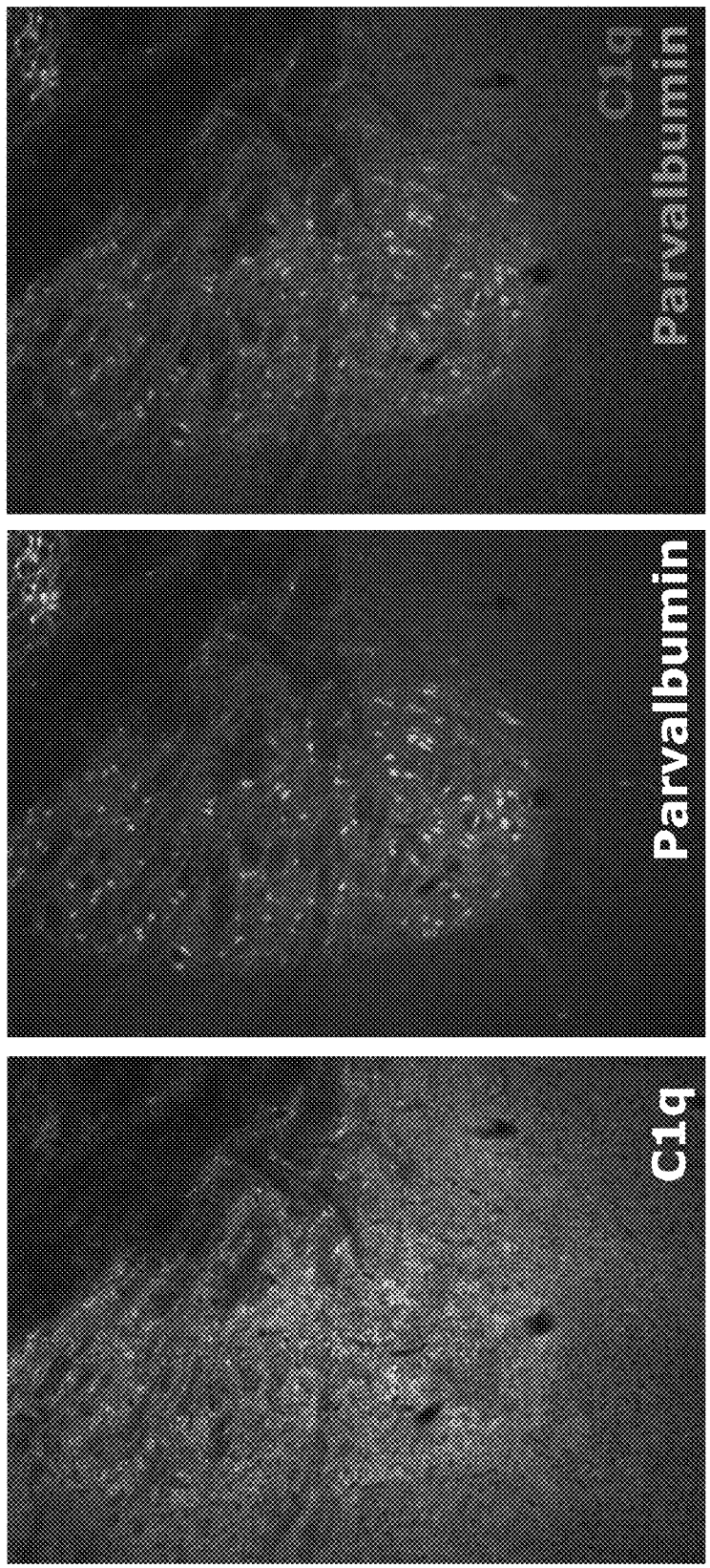
Figure 30:
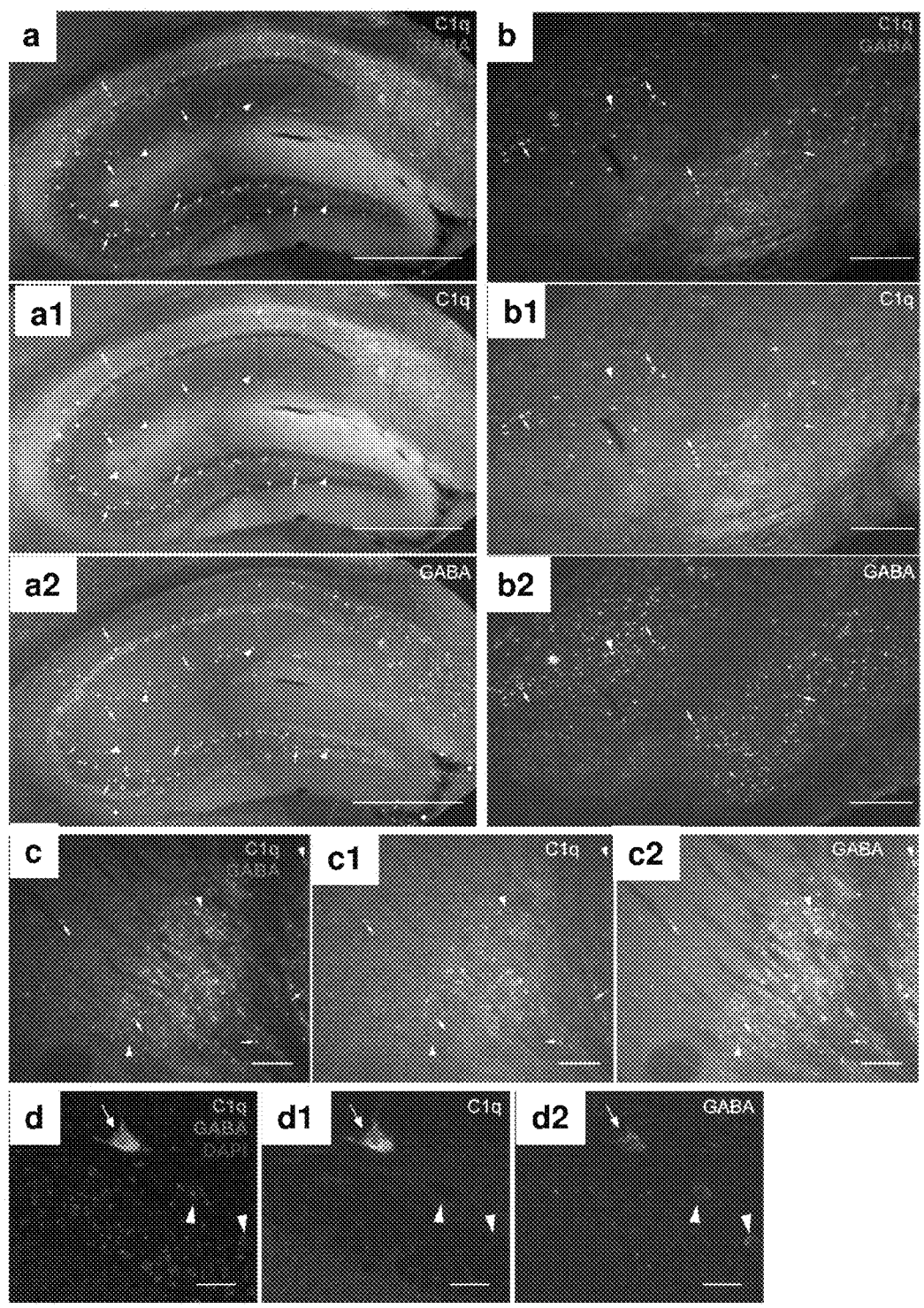
FIG. 30 demonstrates that C1q protein is detected in a subset of inhibitory neurons in distinct areas of the murine brain. a, b, c, Co-localization immunohistochemistry with anti-C1q- and the inhibitory neuron marker anti-GABA antibodies confirmed that all C1q-positive neurons are GABA-positive, identifying these as inhibitory neurons. All C1q-positive neurons in the hippocampus (a), the Substantia Nigra/Midbrain (b) and the Globus Pallidus/Striatum (c) are GABAergic (arrows). However, some GABAergic cells are not stained by the C1q-specific antibody (arrow heads). d, High-power, single-plane confocal microscopy of the adult mouse Dentate Gyrus confirmed C1q-positive neurons as GABAergic. Anti-C1q immunoreactivity co-localized with anti-GABA immunoreactivity (arrow). Note the two additional GABAergic cells not stained by the anti-C1q antibody (arrow heads). a, b, c, and d: costaining of C1q (green) and GABA (red); a1, b1, c1, d1: C1q staining alone; a2, b2, c2, d2: GABA staining alone. Scale bars: a, 500 µm; b, c, 200 µm; d, 20 µm.
Figure 31:
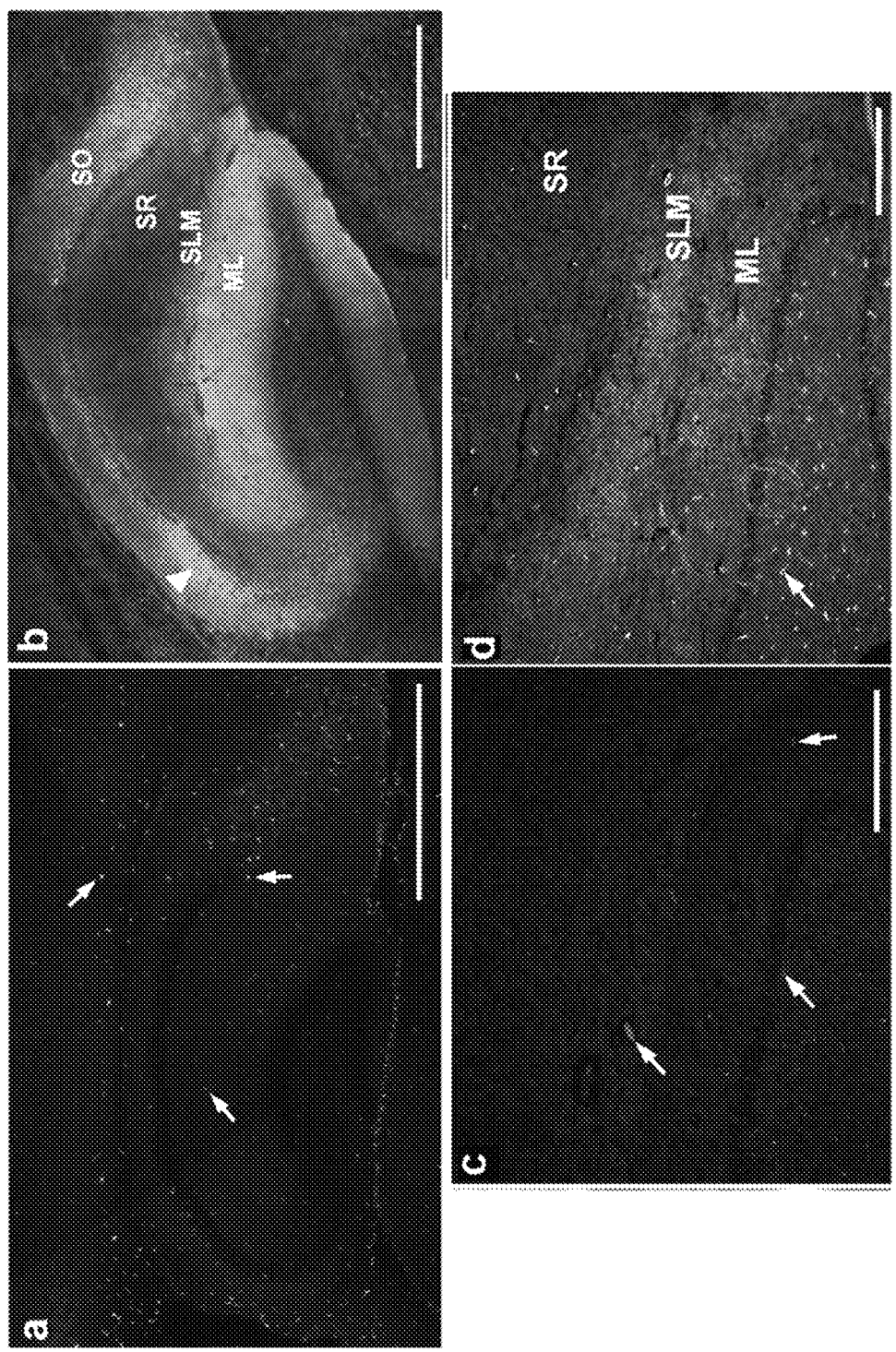
FIG. 31 illustrates that C1q protein dramatically increased with age in hippocampal synaptic layers in both mouse and human. a, Immunohistochemistry analysis confirmed comparably low levels of anti-C1q-immunoreactivity (arrows), representing cellular signals, in the hippocampus from post-natal day six mice. b, C1q-immunoreactivity was dramatically increased in all synaptic layers of the 24 month old murine hippocampus, including the stratum radiatum (SR). However, signals were particularly strong in the Dentate Gyrus molecular layer (ML), the stratum lacunosum moleculare (SLM) and, to some degree, in the stratum oriens (SO). In addition, very strong anti-C1q immunoreactivity was detected in the neuropil surrounding the CA2 cell bodies (arrow head). c, d, representative anti-C1q immunoreactivity in human hippocampal slices from both infant (c) and aged (d) donors confirmed that C1q protein also dramatically increased with age in synaptic layers of the human Hippocampus. As in mice, C1q protein was particularly enriched in the stratum lacunosum moleculare (SLM) and the Dentate Gyrus molecular layer (ML) but to a lesser extend in the stratum radiatum (SR). In addition to anti-C1q immunoreactivity in the neuropil, signals were also detected in blood vessels (arrows), indicating serum-derived C1q in this non-perfused tissue. Scale bars: a, b, c, d, 500 µm.

To determine which cells expressed C1q, in situ hybridization with probes for C1q-A and CXCR1 was performed. At P30, most or all microglia express C1q (FIG. 27). C1q immunoreactivity is also found in a subset of neurons in the developing and adult mouse brain, e.g. the hippocampus, thalamus, striatum, and midbrain (FIG. 28). Co-staining with parvalbumin, a marker of inhibitory neurons, indicates that C1q immunoreactive neurons are mainly inhibitory (FIG. 29).

Figure 32:
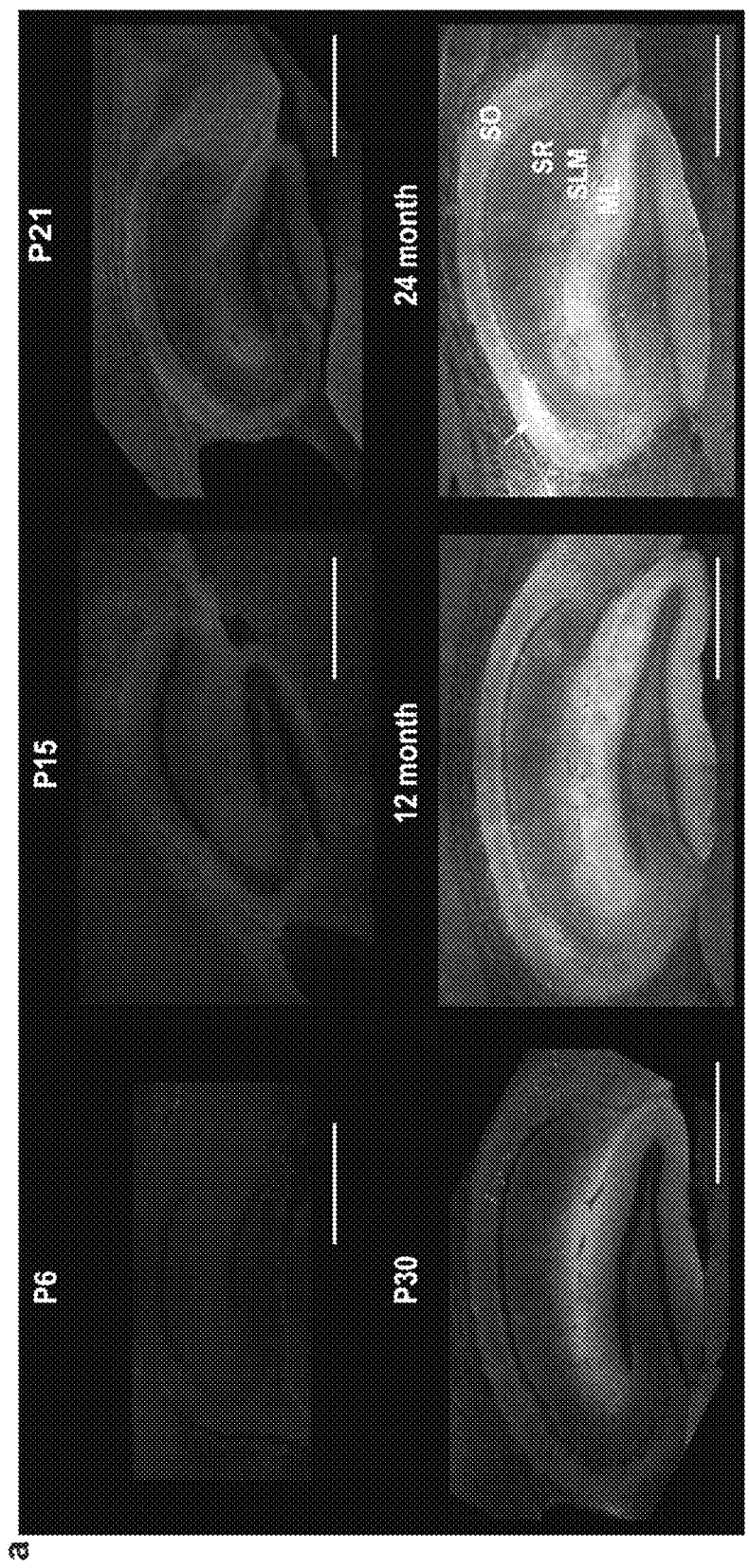
FIG. 32 demonstrates that C1q protein dramatically increased in the aging murine hippocampus. a, Time-course immunohistochemistry analysis of slices from perfused, early postnatal to old aged mouse brains confirmed that C1q protein levels dramatically increase with age in synaptic layers of the Hippocampus, including the stratum radiatum (SR). However, signals particularly increased in the Dentate Gyrus molecular layer (ML), the stratum lacunosum moleculare (SLM) and in the stratum oriens (SO). In addition, very strong anti-C1q immunoreactivity was detected in the neuropil surrounding the CA2 cell bodies (arrow). b, Western blot analyses of mouse Hippocampus homogenates (perfused mice) confirmed the dramatic age-dependent increase of C1q protein (arrow head) in the hippocampus, when compared to the βTubulin loading controls (arrow: additional, unspecific band detected by the antibody used). c, Like in whole brain homogenates, C3 protein levels (arrow head) in the Hippocampus are comparably high at early postnatal stages but decrease to constantly low levels from about 1 month of age onwards, when compared to the βTubulin loading controls (arrow: additional, unspecific band detected by the antibody used). d, e, The increase with age in the Hippocampus is C1q-protein specific as other CNS proteins, like synaptotagmin (d) and GluR1 (e), do not show a similar regulation. P—postnatal day; m—month; Scale bars: 500 µm.
Figure 32:
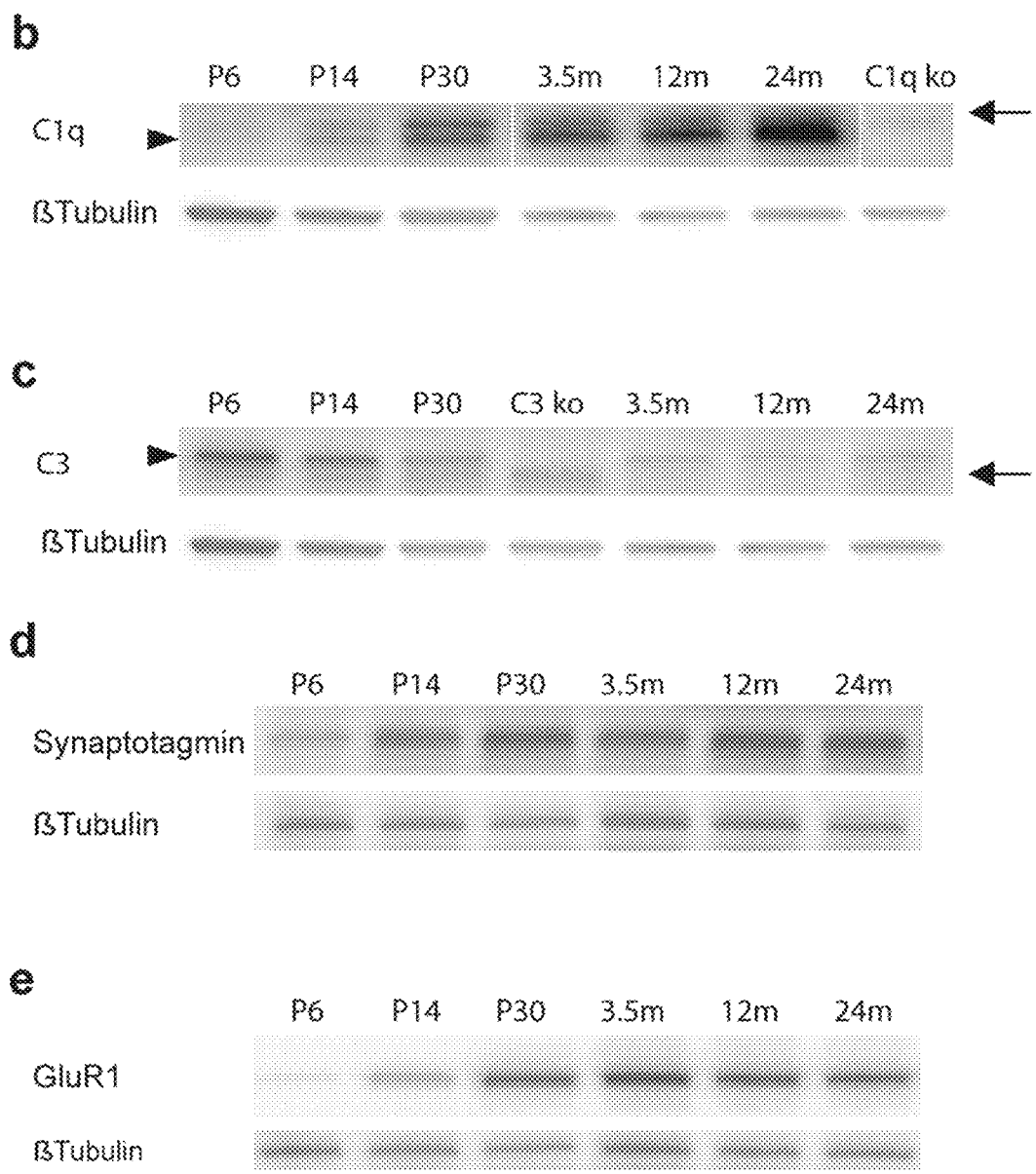
Figure 33:
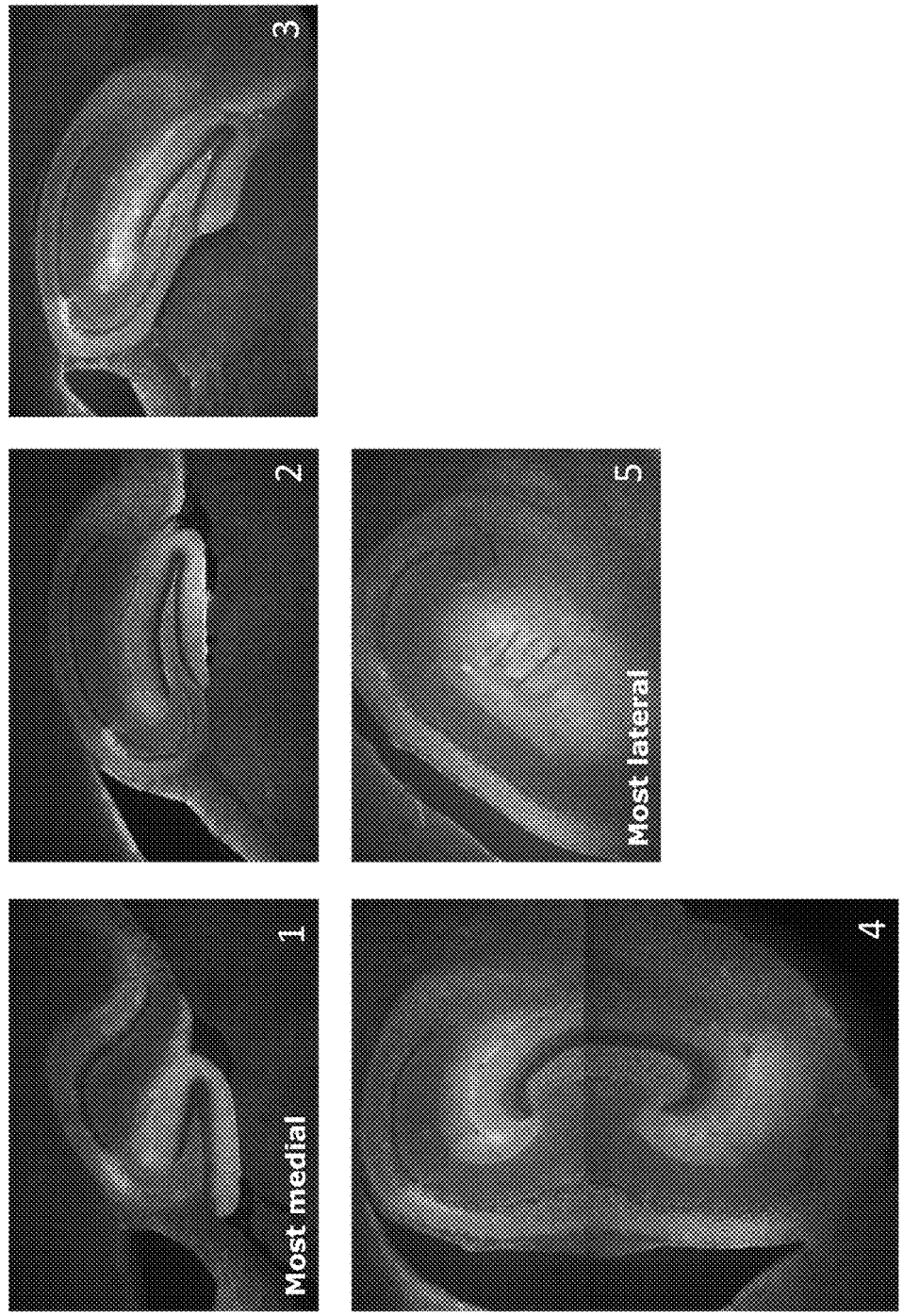
FIG. 33 demonstrates that C1q staining pattern is consistent throughout entire adult hippocampus. sagittal sections. 1 is most medial, 5 is most lateral.
Figure 34:
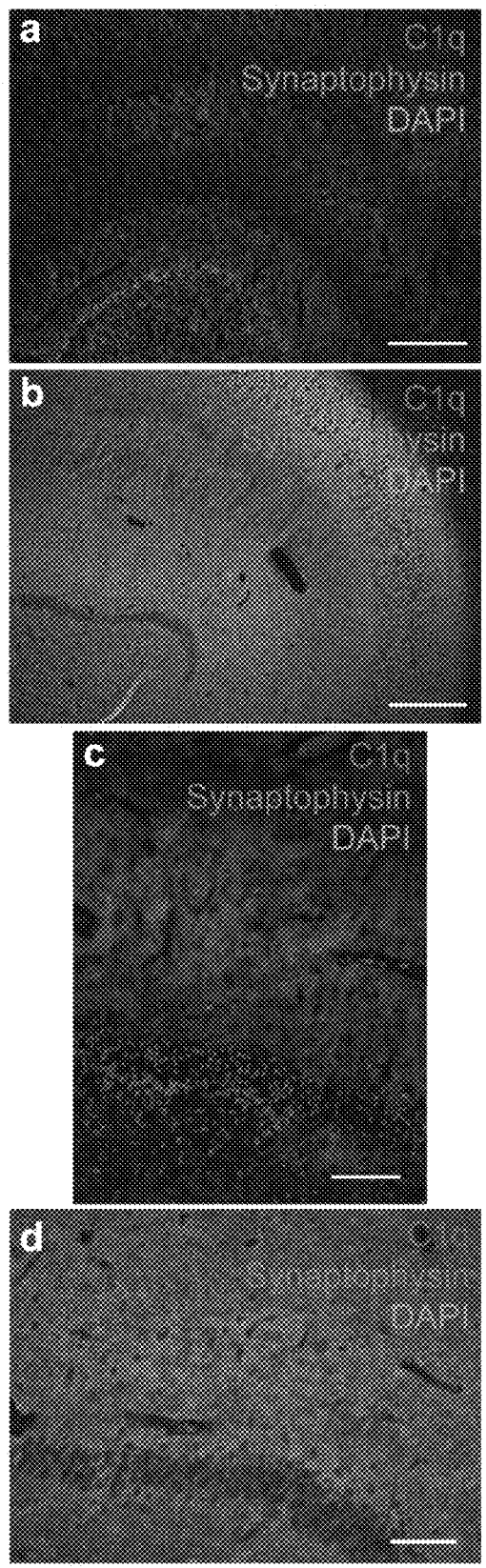
FIG. 34 illustrates that C1q protein dramatically accumulates in synaptic layers of the aging human hippocampus. a-d, Anti-C1q immunohistochemistry of human Hippocampus slices from infants (a, 7 month old; c, 2 month old) and a 75 year old donor (b, d) confirmed that C1q protein (a1, b1, c1, d1) dramatically increased with age in the neuropil of synaptic layers, in particular in the Dentate Gyrus molecular layer (ML) and the stratum lacunosum moleculare (SLM), and to a lesser extend in the stratum radiatum (SR). Anti-Synaptophysin signals (a2, b2, c2, d2) were detected in all synaptic layers, independent of age. DAPI (a3, b3, c3, d3) labeled the cell bodies. Arrows indicate serum-derived C1q-signals in blood vessels of this unperfused tissue. e, Western blot of human tissue samples confirmed the absolute specificity of the rabbit anti-human C1q antibody used for the human tissue immunohistochemistry analysis. The antibody exclusively detected all subunits of human C1q in both human serum (adult) and human hippocampal homogenate from the 75 year old donor also analyzed by immunohistochemistry in b, and d. No signals were detected in the C1q-depleted human serum sample, arguing for the absolute specificity of the antibody. a, b, c, and d: costaining of C1q (red), synaptophysin (green), and DAPI (blue); a1, b1, c1, d1: C1q staining alone; a2, b2, c2, d2: synaptophysin staining alone; a3, b3, c3, d3: DAPI staining alone. kD-kilo Dalton; Scale bars: a, b, 500 µm; c, d, 100 µm.
Figure 34:
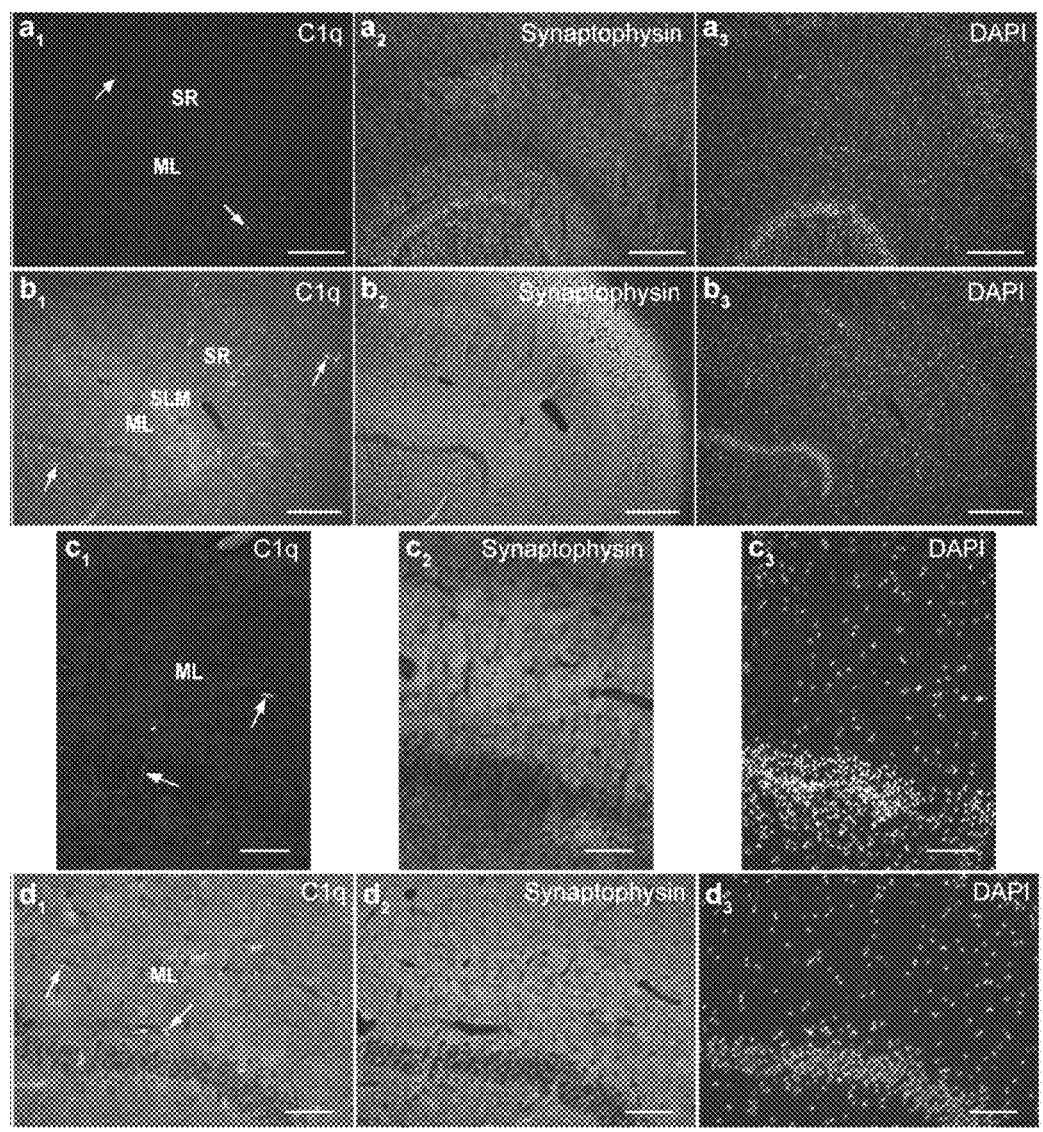
Figure 34:
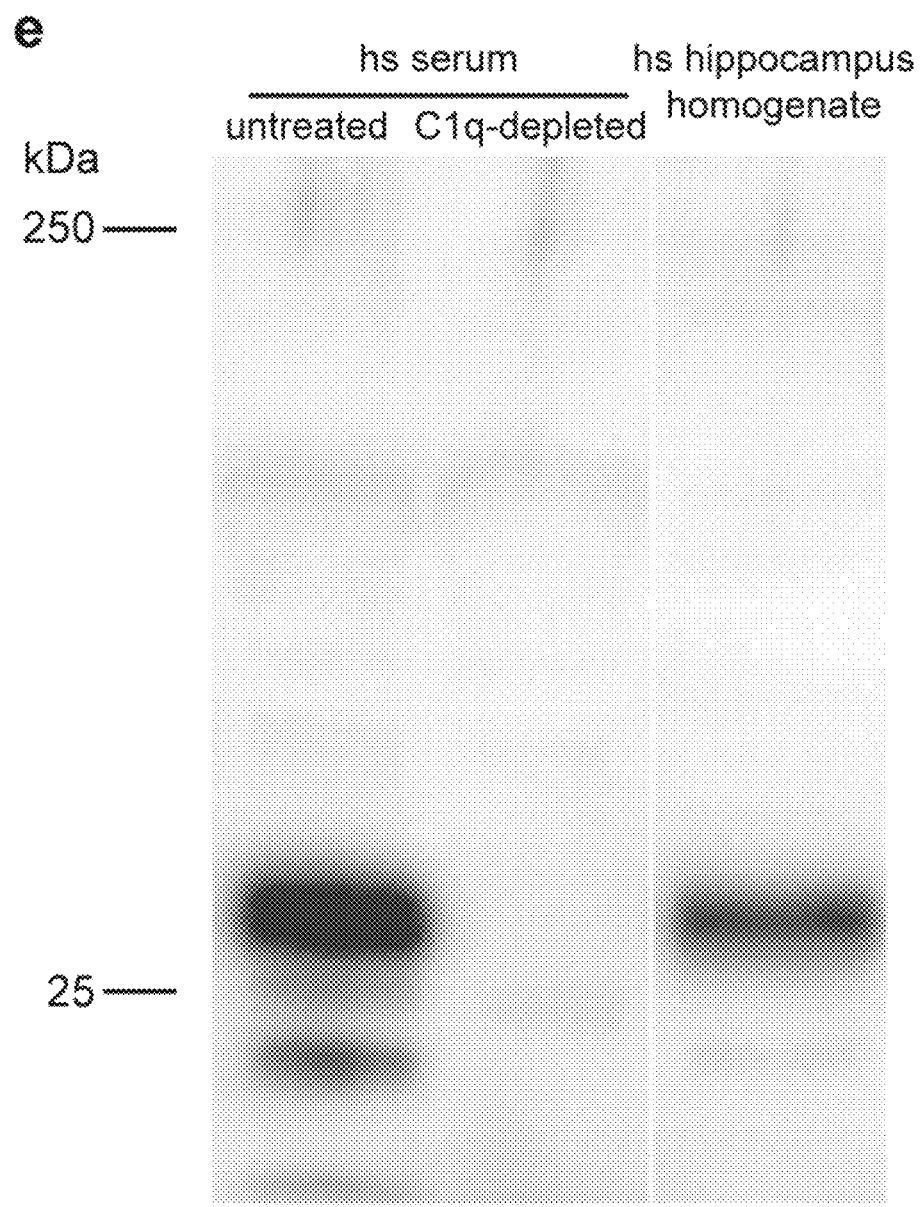
Figure 35:
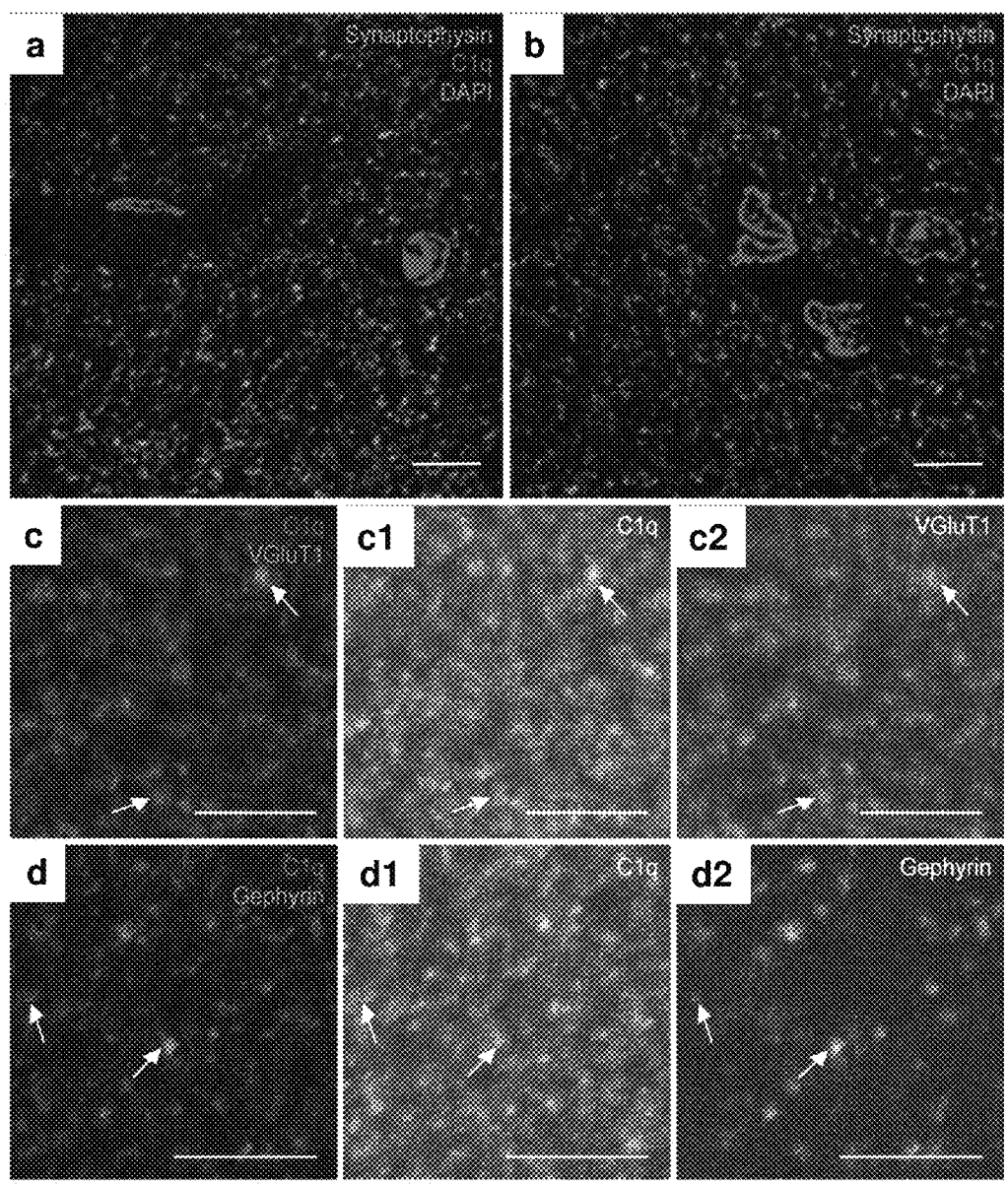
FIG. 35 illustrates that C1q protein localizes to synapses in the adult and aged Hippocampus. a, b, Anti-C1q immunohistochemistry signals visualized by confocal microscopy are specific. Anti-C1q immunoreactivity was only detected in the adult C1q wild-type Dentate Gyrus molecular layer (a) but not in the corresponding tissue from C1q KO littermate mice (b). c, d, Most anti-C1q signals were detected in close proximity to synaptic protein signals in this high-power confocal microscopy co-localization study with the excitatory synaptic protein VGluT1 (c) and the inhibitory synaptic protein Gephryn (d) (c: costaining of C1q (red) and VGluT1 (red); c1: Cq1 staining alone; c2: VGluT1 staining alone; d: costaining of C1q (red) and Gephryn (green); d1: C1q staining alone; d2: Gephryn staining alone). In addition, absolute co-localization of C1q with these synaptic proteins (arrows) was occasionally observed. These results suggested that C1q protein also localizes to both excitatory and inhibitory synapses. e-h, Cryo-immuno electron microscopy confirmed that C1q protein indeed localized to the outside of both pre- and postsynaptic elements (arrows) in the Dentate Gyrus molecular layer of adult and aged mice. e, Anti-C1q immunoreactivity, visualized with 12 nm gold particles, was detected in close proximity to both pre-synaptic (green) and postsynaptic (brown) elements in tissue from adult mice. In addition, a few signals were associated with unidentified structures (arrow head). This single-plane image analysis did not allow clear identification of all elements visible in each section. It is therefore impossible to classify anti-C1q immunoreactivity associated with unidentified elements as synaptic or extra-synaptic (see panel f for explanation—anti-Synaptophysin signals). f, Dual-immuno-gold analysis in the Dentate Gyrus molecular layer of aged mice. Anti-C1q immunoreactivity (12 nm gold particles, arrows) was detected in close proximity to both pre-synaptic (green) and postsynaptic (brown) elements. In contrast, anti-Synaptophysin immunoreactivity (6 nm gold particles, arrow heads) was detected inside clearly identifiable presynaptic terminals as well as associated with unidentifiable structures, likely reflecting presynaptic terminals. g, h, Anti-C1q cryo-immuno electron microscopy signals are specific. Anti-C1q immunoreactivity (12 nm gold particles) was only detected in the adult C1q wild-type Dentate Gyrus molecular layer (g) but not in the corresponding tissue from C1q KO littermate mice (h). In wild-type animals, C1q-immunoreactivity was detected in close proximity to synaptic elements (arrows) as well as associated with unidentified structures (arrow heads). Scale bars: a-d, 5 µm; e-h, 200 nm.
Figure 35:
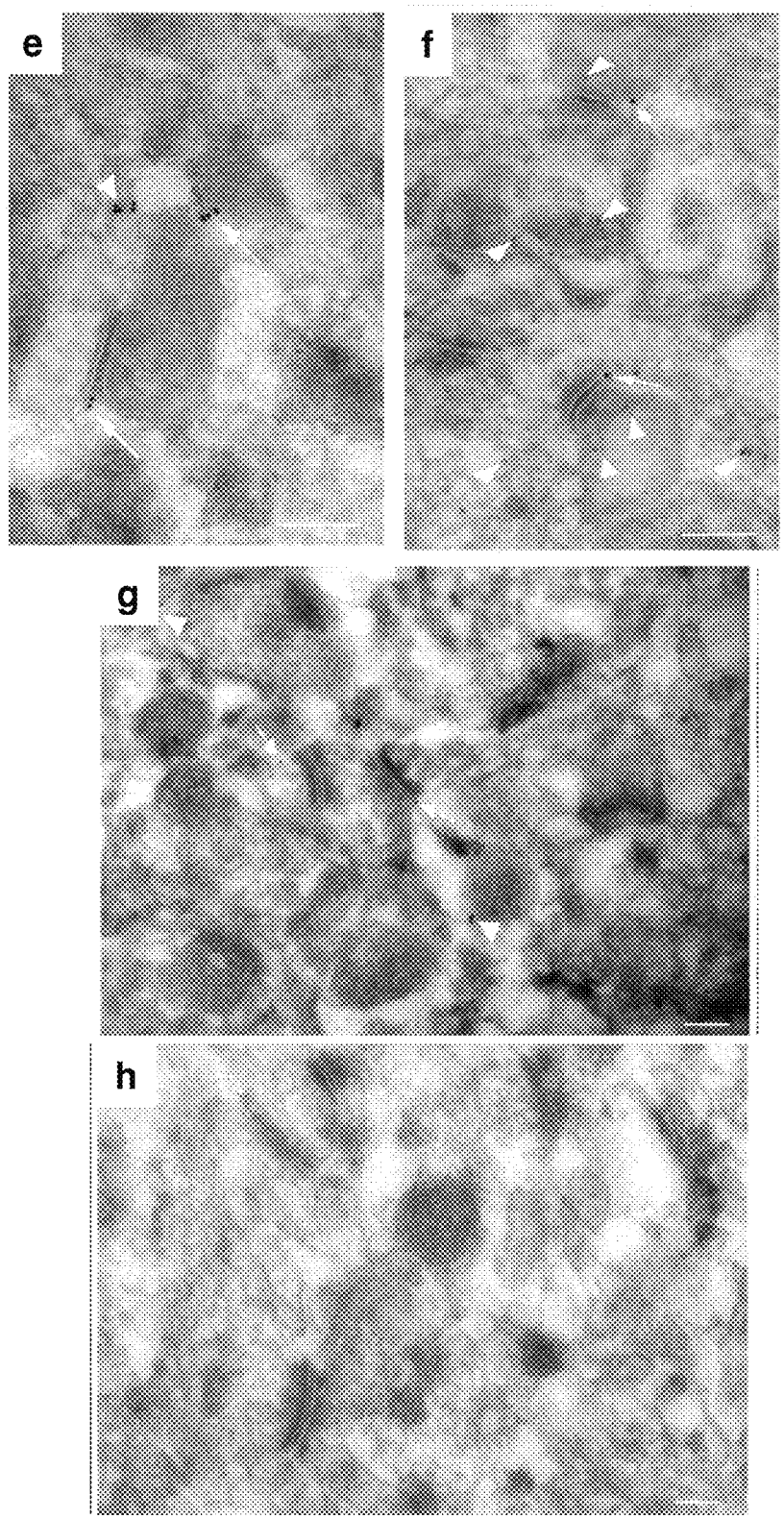

C1q immunostaining also indicates that the increase in C1q immunoreactivity with aging is highly synaptically localized, appears at P15 coincident with synapse formation, and is especially high in the dentate gyrus (FIG. 32). Synaptic localization was confirmed by co-staining with synaptophysin (FIG. 34). Co-staining with VGluT1 indicated that C1q immunreactivity localizes to many excitatory synapses in the dentate gyrus of older mice (FIG. 35*c*), while co-staining with Gephryn indicated that C1q immunreactivity localizes to many inhibitory synapses in the stratum lacunosum (FIG. 35*d*). Electron microscopy revealed that C1q could be found in close proximity to synapses (FIG. 35*e-f*).

Figure 19:
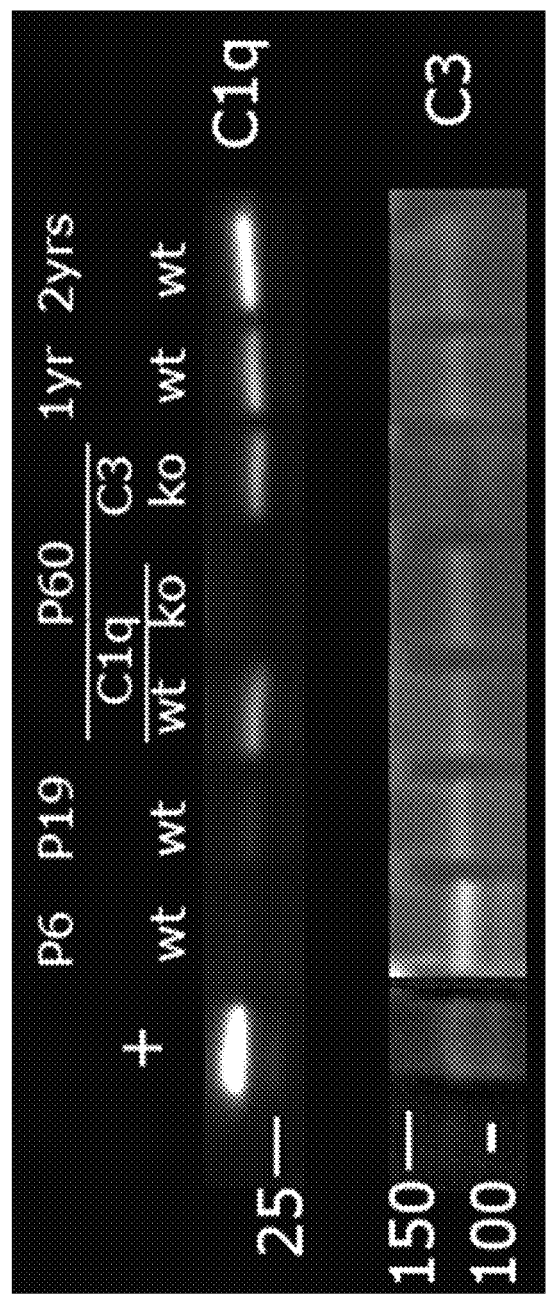
FIG. 19 demonstrates that C3 protein is expressed in CNS tissue throughout adulthood.
Figure 20:
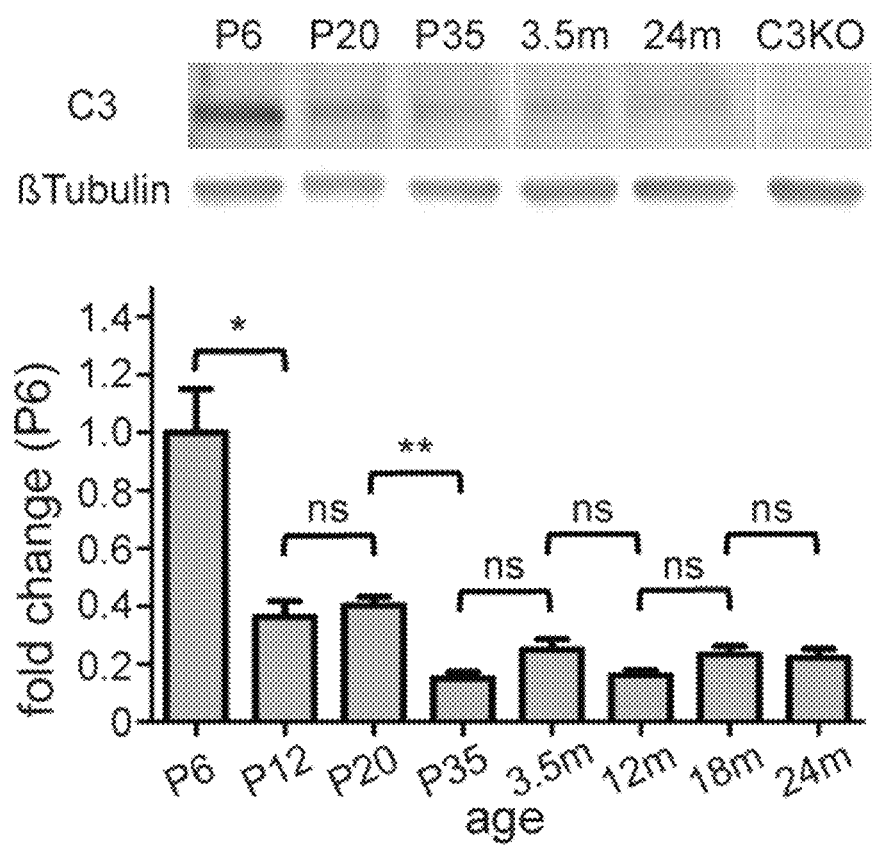
FIG. 20 demonstrates that C3 protein does not increase with aging in the murine brain. Western blot analysis of perfused, whole-brain homogenates revealed that, in contrast to C1q, C3 levels did not increase with age in the murine brain. Instead, C3 protein levels were high at early postnatal ages and decreased to constantly low levels at about one month of age and after when compared to the βTubulin loading controls. These anti-C3 signals were specific as the corresponding band was not present in brain homogenate from C3 KO mice (C3KO). j, Quantification of Western blot-derived C3 signals, normalized to βTubulin loading controls, confirmed that C3 protein decreased from early postnatal ages to about 1 month of age (C3 levels, normalized to P6 levels: P6: 1-fold, +/−0.14; P12: 0.43-fold+/−0.07; P20: 0.41-fold+/−0.05; P35: 0.12 fold+/−0.01; n=3 animals/age. Significance: P12 versus P6: P=0.029; P20 versus P12: P=0.434; P35 versus P20: P=0.003, unpaired t-test). From about 1 month of age and after, C3 protein levels were detectable at comparably low levels (P35 normalized to P6 levels: 0.12 fold+/−0.01; 3.5 month: 0.26+/−0.07; 12 month: 0.17+/−0.01; 18 month: 0.23+/−0.02; 24 month: 0.22+/−0.03; n=3 animals/age; 3.5 month versus P35: P=0.07; 12 month versus 3.5 month: P=0.18; 18 month versus 12 month: P=0.50; 24 month versus 18 month: P=0.88). P—postnatal day; m—month; per.—perfused; n.p.—not perfused; scale bars: a, b, 1 mm; c, d, 100 μm; ns—not significant, *P<0.05, **P<0.01. Values represent mean+/−S.E.M. Error bars represent S.E.M.

To determine if the classical complement cascade is activate during normal aging, the expression levels of C3 were assessed in different aged mice. C3 protein levels were high shortly after birth (P6), as expected in view of the extensive remodeling and synapse elimination that occurs during this developmental window (FIGS. 19, 20, P6). Interestingly, measurable C3 protein levels were also observed through adulthood, indicating that the classical complement cascade is active in the CNS throughout adult life.

In summary, C1q expression in the CNS is developmentally regulated, C1q levels being low at birth and increasing during maturation and aging. C1q is expressed by microglia throughout the brain and by a large percentage (but not all) inhibitory neurons. In some embodiments, the C1q inhibitor targets inhibitory neurons. The increase in C1q protein with aging primarily occurs by accumulation at synapses throughout the CNS starting in hippocampus (dentate gyrus), cortex, midbrain, followed by thalamus, brainstem, and finally cerebellum. These findings support the conclusions above that increased activation of the complement cascade in aging and other age-related neurodegenerative conditions causes excessive synapse loss which results in cognitive decline.

Example 3

Wild type mice and C1q-deficient mice were assessed using several electrophysiological tests to determine the state of decline in function of hippocampal neurons at 3 months of age, 9 months of age, and 15 months of age. This included assessing the Perforant Path/Dentate Gyrus synaptic pathway for input output curves of dentate gyrus molecular layer field potentials, which measure the relationship between stimulus size and the size of the evoked synaptic response to address synaptic properties or architecture; the Perforant Path/Dentate Gyrus pathway for paired-pulse facilitation, which measures the rapid succession of two presynaptic stimuli; and the Perforant Path/Dentate Gyrus pathway and Schaffer collateral/CA1 pathway for long-term potentiation, which measures the extent of long-lasting enhancement in signal transmission between two neurons that results from synchronus, high-frequency stimulation.

In addition, wild type mice and C1q-deficient mice were assessed using the following behavior tests to determine the state of cognitive decline at 3 months of age, 9 months of age, and 15 months of age:

SHIRPA: systematically assess the general health and behavioral traits of a transgenic mouse.
Activity Chamber: determine general activity levels, gross locomotion activity, and exploration habits.
Open Field: measure behavioral responses such as locomotor activity, hyperactivity, exploratory behaviors, anxiety.
Y-Maze: Hippocampus-dependent navigation behaviors and spatial working memory.
Novel Object Recognition: Hippocampus and pre-frontal cortex-dependent spatial displacement and recognition memory.
Morris Water Maze: Hippocampus-dependent spatial learning and memory Contextual and tone-cued Fear Conditioning: Hippocampus/Amygdala-dependent Pavlovian (associative) learning.

Figure 36:
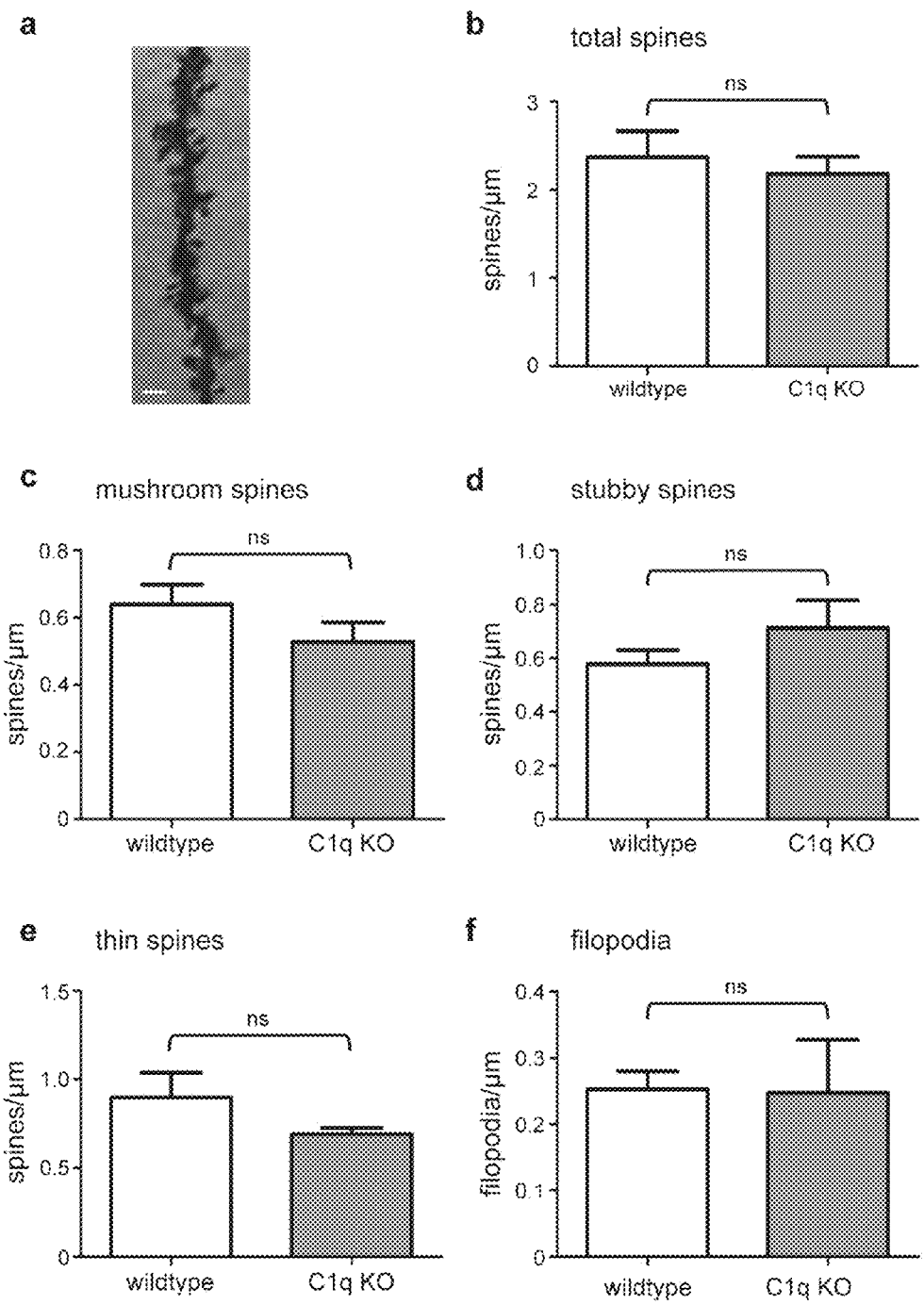
FIG. 36 illustrates that C1q-deficiency did not affect dendritic spine number or spine morphology in old aged mice. a, Representative image of a Golgi-stained dendrite used for the dendritic spine quantification analysis. b-f, Tertiary Dentate Gyrus granule cell dendrites were identified and traced in Neurolucida (MBF Bioscience) and dendritic spines were manually identified, counted (n=4 animals/genotype, 9 dendrites/animal) and quantified as number of spines per µm dendrite length. Spine type categorization was done according Peebles, C. et al. 2010 PNAS 107(42): 18173-78. No significant differences were detected for either total spine number per µm dendrite length (b) or any of the individual spine types counted (c-f). Error bars represent S.E.M.
Figure 37:
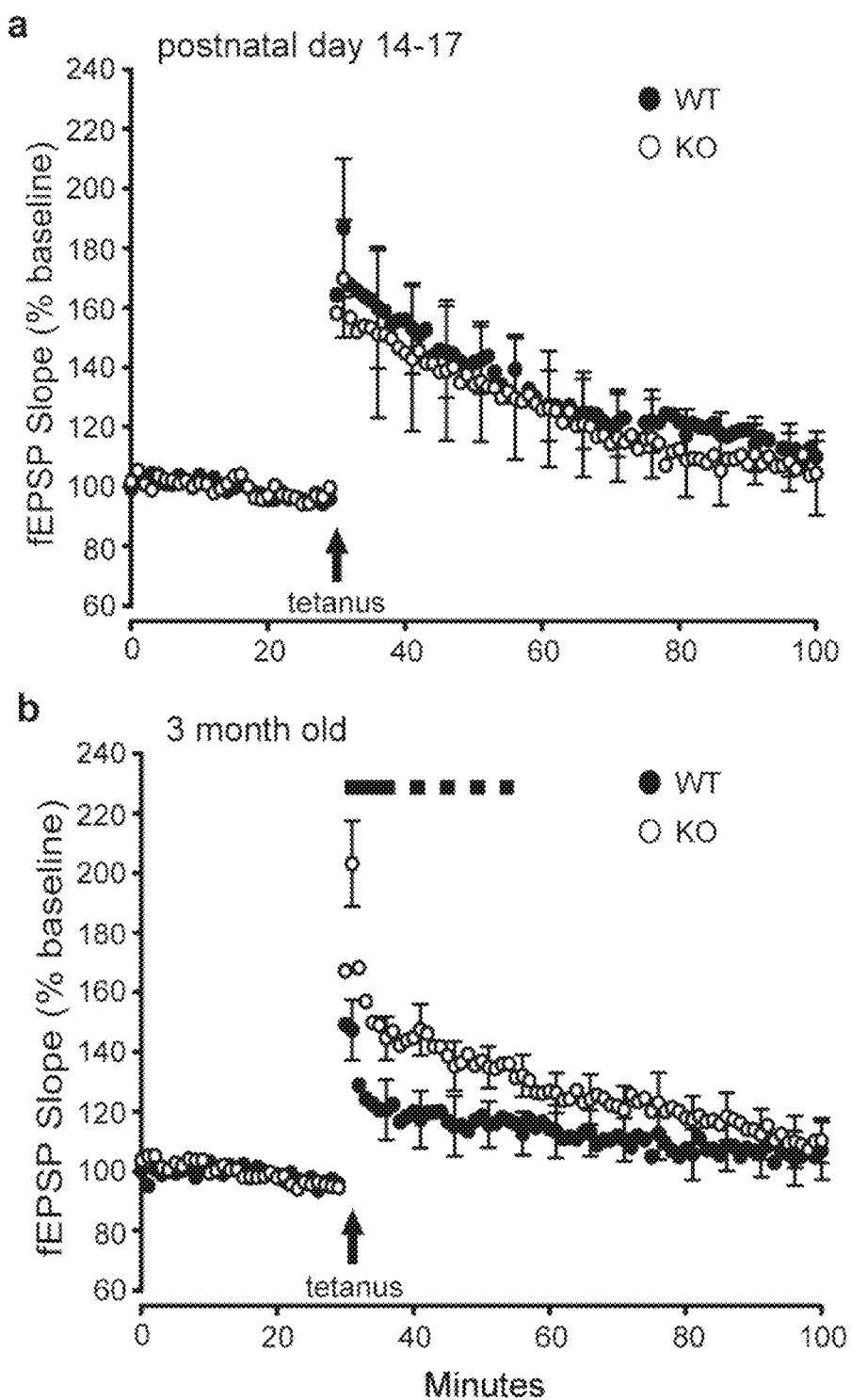
FIG. 37 demonstrates that C1q-deficiency caused enhanced long-term potentiation (LTP) in the Dentate Gyrus of adult mice. a, b, LTP analysis in the Dentate Gyrus molecular layer of young postnatal (a, postnatal day 14 to 17) and adult (b, 3 month old) C1q KO (KO) versus C1q wild-type (WT) littermate mice. Adult C1q KO mice (b, circles) showed enhanced potentiation after tetanic stimulation when compared to their wild-type (squares) littermates. Solid and hatched line indicates interval of significant difference; WT: 117.4+/−0.524 and KO: 139.3+/−1.085 fEPSP (% baseline), P=0.044, 2-way repeated measures ANOVA with Bonferoni posttest. In addition, adult C1q KO mice showed enhanced post-tetanic potentiation when compared to their wild-type littermates (solid line, 1 minute after tetanus: WT: 149.1+/−7.2, KO: 167.1+/−6.7% of baseline). Potentiation in adult C1q KO mice also decayed faster than in their wild-type littermates (P<0.001). This was in strong contrast to early postnatal mice in which LTP levels, post-tetanic stimulation and LTP-decay were nearly identical between C1q KO and C1q wild-type littermates (P=0.93). Each data point presented represents 1 minute averages of 4 individual fEPSPs taken at 15 second intervals. Postnatal day 14-17: n=6 (C1q WT), 6 (C1q KO); 3 month old: n=10 (C1q WT), 12 (C1q KO). Values represent mean+/−S.E.M.; Error bars represent S.E.M.
Figure 38:
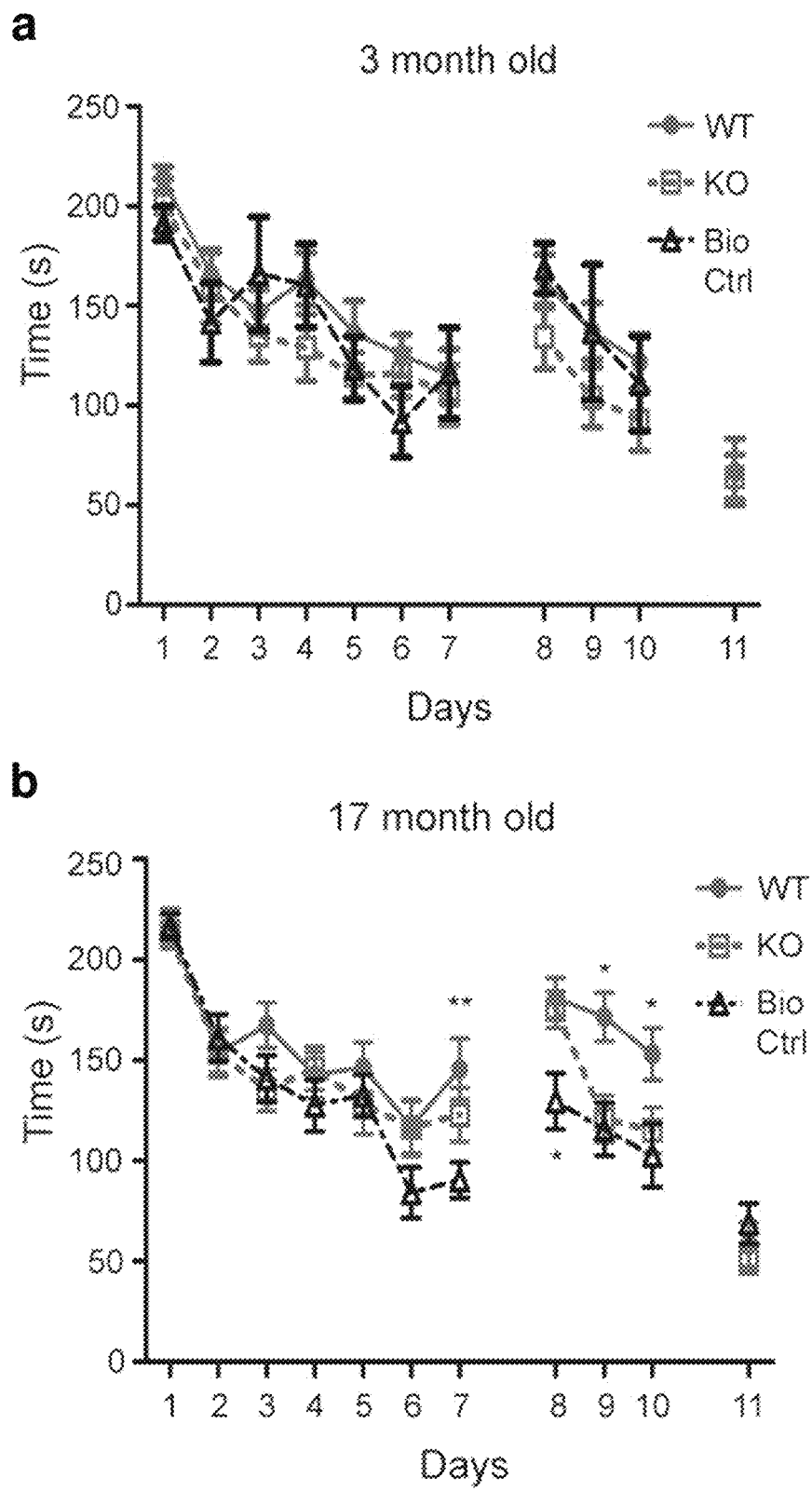
FIG. 38 demonstrates that C1q-deficient mice showed reduced cognitive aging. a, b Morris Water Maze analysis, including reversal learning (days 8, 9, 10; escape latency shown). a, 3 month old adult C1q KO mice (KO), their wild-type littermates (WT), and strain matched control mice (bio controls, Bio Ctrl) performed all parts of the experiment without significant differences. b, Learning of the hidden platform location (days 1-7) was also mostly identical between 17 months old aged C1q KO, their wild-type littermates and young bio controls. Solely on day 7, the bio controls performed significantly better than the aged C1q wild-type mice (in seconds: Bio Ctrl: 90.29+/−8.996; WT; 145.8+/−15.19, P<0.01, repeated measure ANOVA and Bonferoni posthoc test). However, no significant difference in learning was detected between bio controls and aged C1q KO mice (in seconds: 126.2+/−13.48, P>0.05). On the first day of the reversal learning task (day 8), the young bio controls learned the new location of the hidden platform faster than both aged C1q KO and wild-type littermate mice (in seconds: WT: 181.0+/−9.982; KO: 175.2+/−9.095; Bio Ctrl: 129.6+/−13.94; WT versus Bio Ctrl: P<0.05; KO versus Bio Ctrl: P<0.05). However, aged C1q KO mice performed at the two subsequent reversal learning days as fast as the young bio controls (day 9, in seconds: KO: 120.8+/−11.69; Bio Ctrl: 115.8+/−13.11; P>0.05; and day 10, in seconds: KO: 115.2+/−11.49; Bio Ctrl: 102.7+/−15.7; P>0.05). This was in strong contrast to the aged C1q wild-type littermates which showed reduced reversal learning at both days, consistent with an age-related decline in cognitive flexibility (day 9, in seconds: WT: 171.5+/−12.13; WT versus KO: P<0.05; WT versus Bio Ctrl: P<0.05; and day 10, in seconds: WT: 153.0+/−12.91; WT versus KO: P>0.05; WT versus Bio Ctrl: P<0.05). There were no significant differences between all cohorts during visible platform learning (day 11), indicating that all animals can properly see. c, The C1q KO mice performed spontaneous alternations in the Y-Maze task at all ages significantly above chance (50%), equally good as the 3 month old bio controls. In contrast, 17 month old wild-type littermate mice did not perform above chance levels, indicating age-related decrease in spatial working memory in the aged wild-type but not aged C1q KO littermates (at 17 month of age: WT: 56.4%+/−3.91, P=0.116; KO: 64.60+/−2.83 S.E.M; P=0.0009; Bio Ctrl: 61.72+/−3.39; P=0.0072, one-sample t-test). d, C1q KO mice showed delayed age-related memory decline in the Novel Object Recognition task. Whereas all young adult (3 month old) mice performed this task without significant differences equally well, middle-aged (12 month old) C1q wild-type mice were no longer able to significantly differentiate between a novel and a familiar object, indicating an age-dependent decline in recognition memory (in seconds: WT, familiar object: 29.96+/−4.968 and WT, novel object: 45.14+/−5.818, P=0.062, paired t-test). In strong contrast, middle aged C1q KO mice (12 month old) were still able to learn the task, with similar performance as the young bio controls (all in seconds: KO, familiar object: 36.33+/−7.497 and KO, novel object: 61.84+/−6.990, P=0.033; Bio Ctrl, familiar object: 32.26+/−6.452 and Bio Ctrl, novel object: 52.47+/−8.070, P=0.049). However, at 17 month of age, both C1q wild-type and C1q KO mice failed to learn the task (all in seconds: WT, familiar object: 13.84+/−2.594 and WT, novel object: 17.99+/−4.026, P=0.379; KO, familiar object: 18.12+/−3.648 and KO, novel object: 19.75+/−2.947, P=0.646; Bio Ctrl, familiar object: 16.44+/−2.334 and Bio Ctrl, novel object: 27.88+/−3.147, P=0.032). 3 month old: n=13 wild-type, 13 C1q KO littermates; 10-12 month old: n=16 wild-type, 14 C1q KO littermates; 17 month old: n=11 wild-type, 9 C1q KO littermates; bio controls: n=10; ns—not significant, *P<0.05, **P<0.01, *<0.001. Values represent mean+/−S.E.M.; Error bars represent S.E.M.
Figure 38:
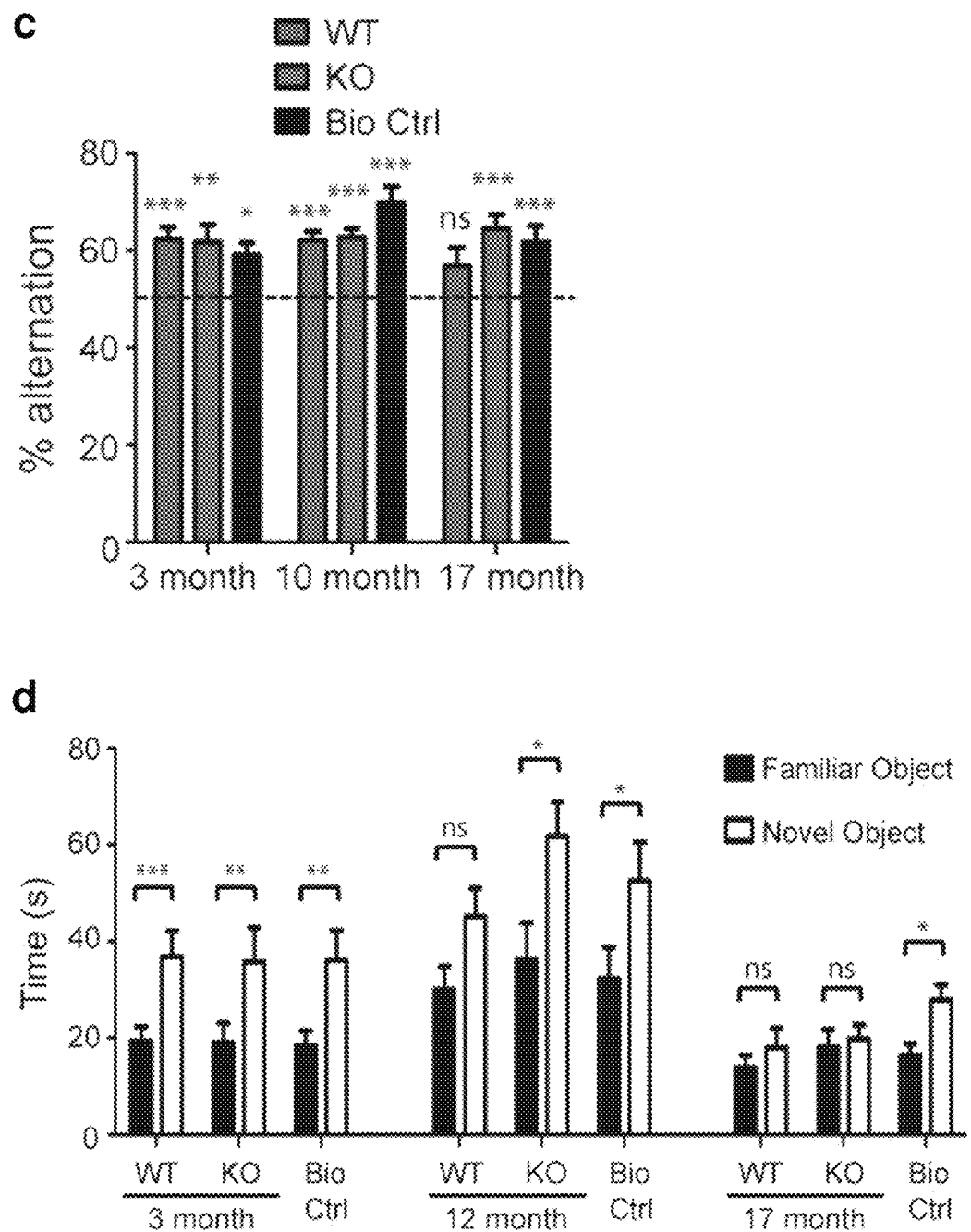
Figure 40:
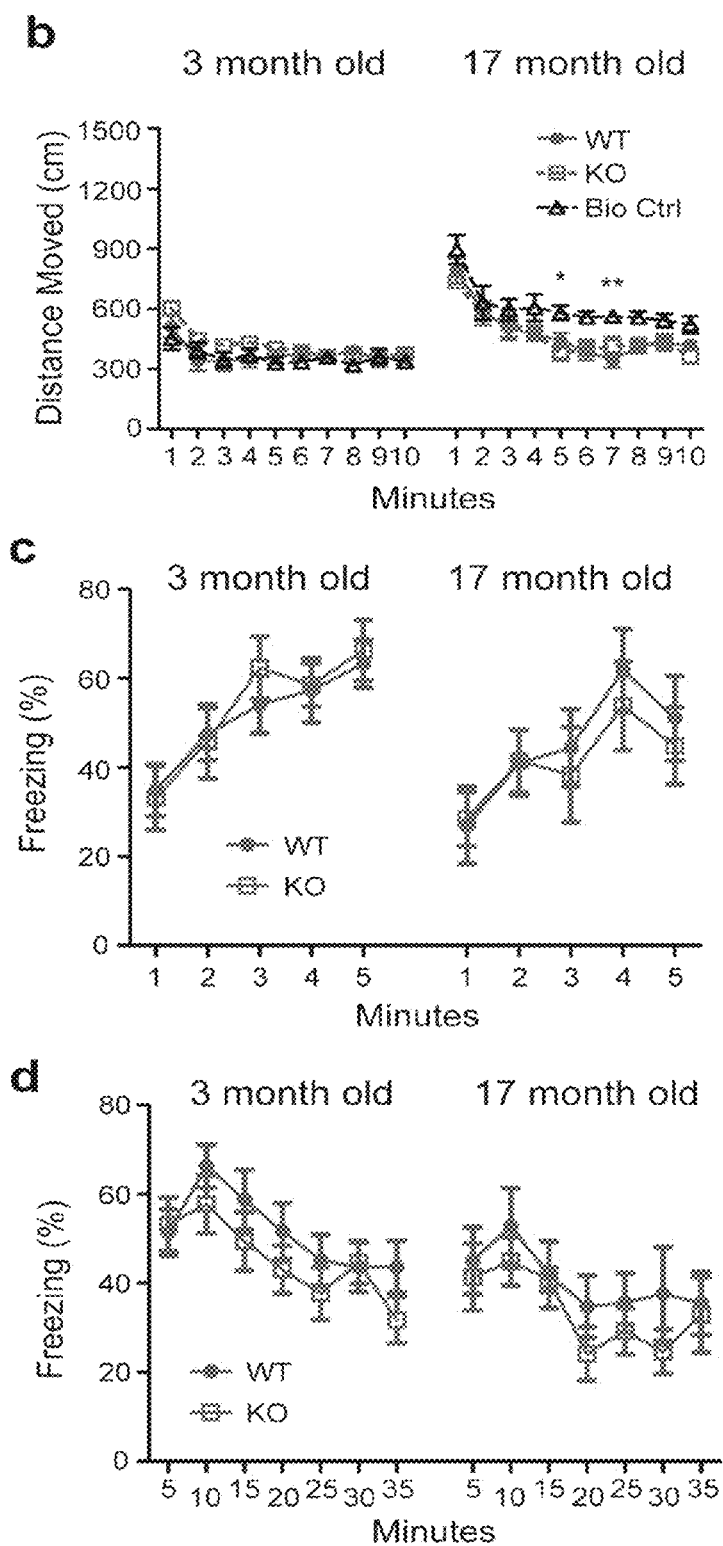
FIG. 40 demonstrates that C1q-deficient mice were overall healthy and showed normal behavior in basic behavioral tasks as well as in fear conditioning/fear extinction analysis. a, SHIRPA analysis confirmed that basic animal behavioral traits did not differ significantly between adult C1q KO mice (KO), C1q wild-type (WT) littermate mice and the strain- and age-matched biological controls (Bio Ctrl). b, Open field analysis confirmed that C1q KO mice have activity levels identical to their wild-type littermates at both young adult and old ages. As to be expected, the 3 month old biological control mice traveled slightly longer distance than the 17 month old C1q KO and wild-type littermate mice (significant difference between C1qWT/KO and the bio controls at 5 minutes: $P<0.05$, and 7 minutes: $P<0.01$; no significant difference at all other time points ($P>0.05$); Bonferoni posthoc test). c, d, Contextual Fear conditioning (c) and Fear Extinction (d) analysis revealed nearly identical learning of C1q KO and C1q wild-type littermate mice at both 3 month and 17 month of age. Both genotypes performed the Fear Conditioning task without significant statistical difference in freezing (c) and showed comparable ability to unlearn the conditioned response in the Fear Extinction task (d). e-h, Supporting data for the Morris Water Maze results presented in FIG. 4. e, g, During the probe trial, with the escape platform missing, both 3 month old (e) and 17 month old (h) C1q KO and C1q wild-type littermates as well as the young bio controls preferred the target quadrant (TQ). f, h, For velocity, no significant genotype difference was detectable ($P>0.05$), repeated measures ANOVA).
Figure 40:
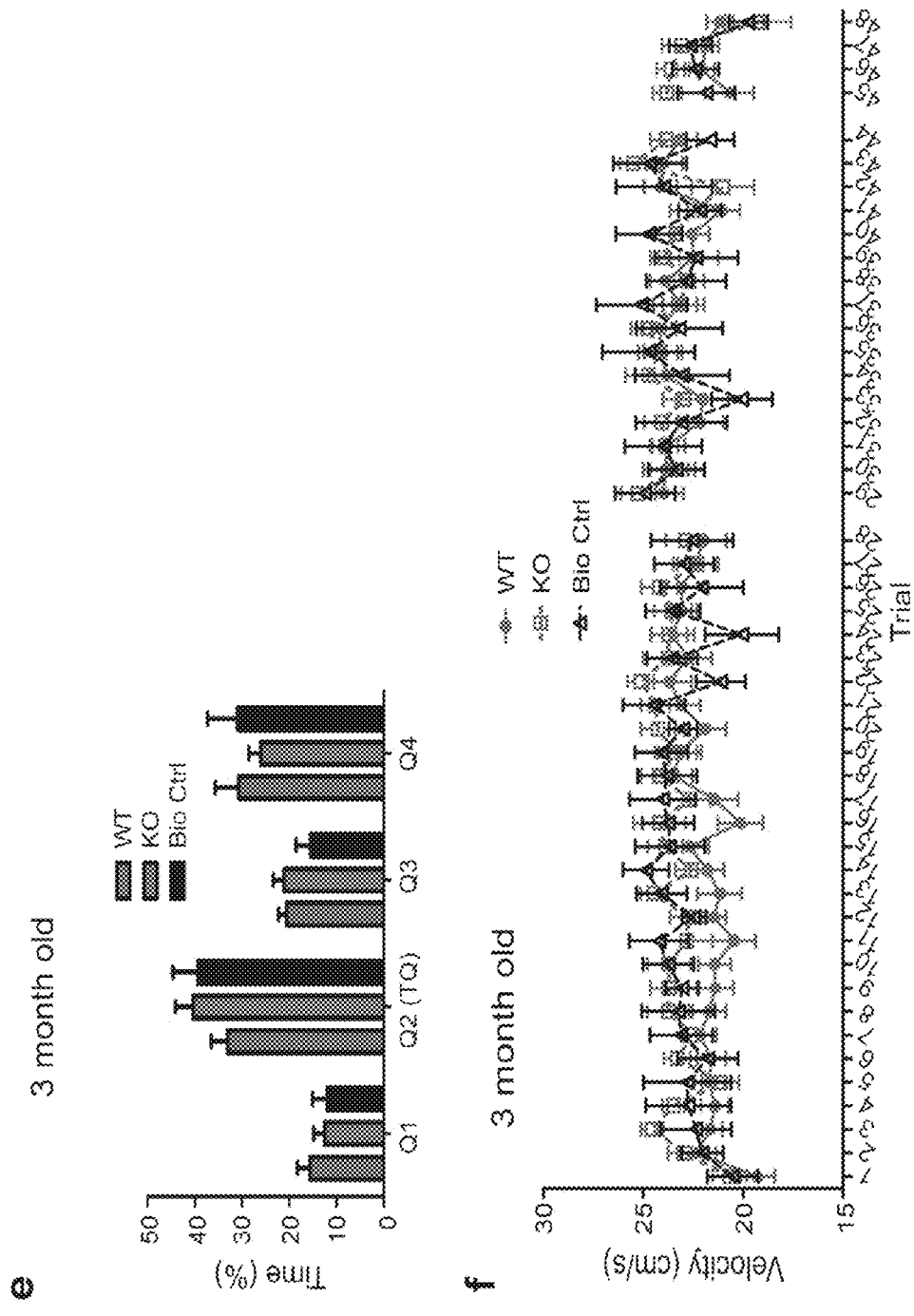
Figure 40:
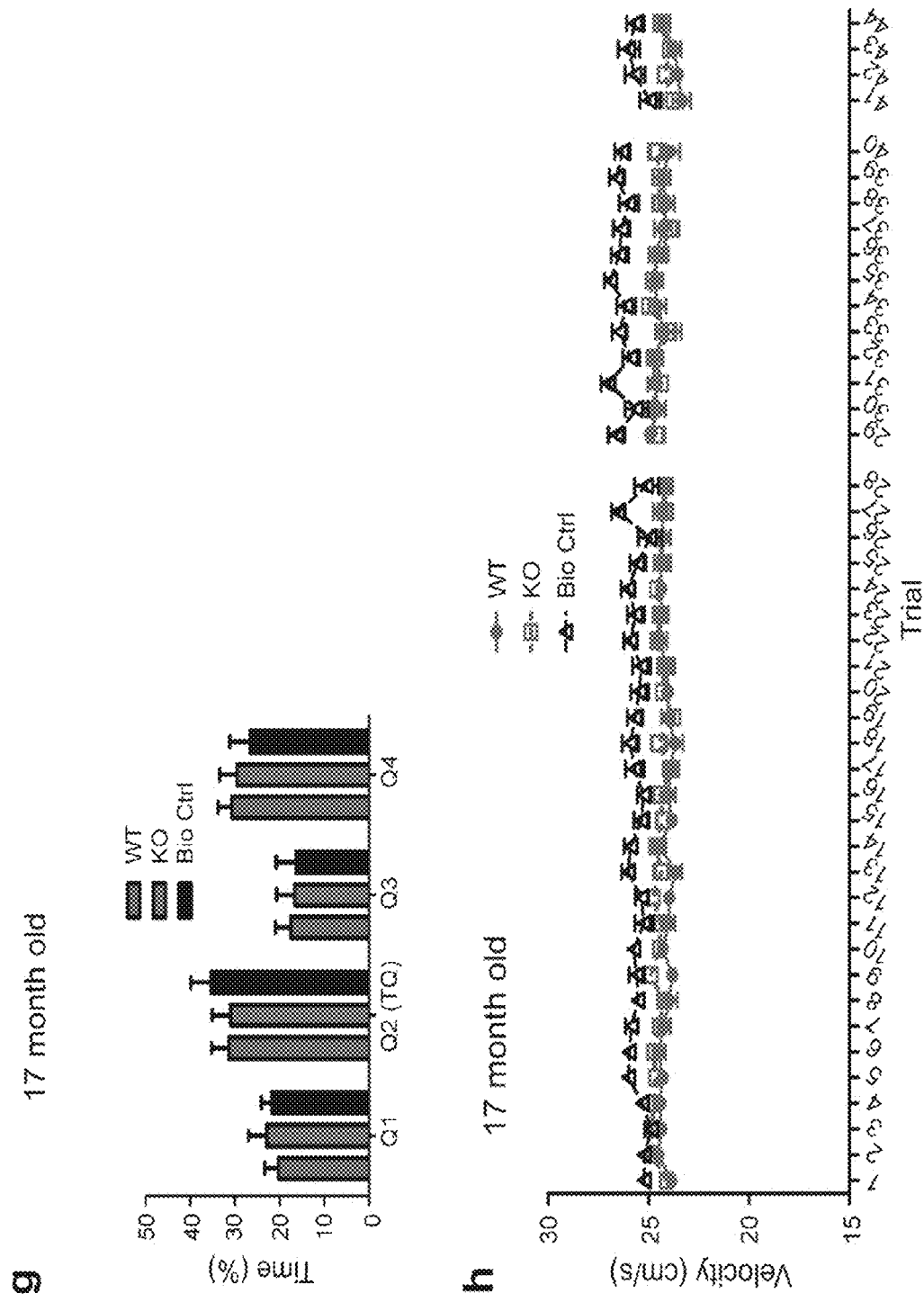

Adult C1q deficient mice were healthy overall and exhibited normal behavior in basic behavioral tasks as well as in fear conditioning/fear extinction analysis (FIG. 40). The number and morphology of dendritic spines was comparable to that of wild type mice (FIG. 36). However, as demonstrated in FIGS. 37-38, less aging-associated decline in neuronal function was observed in C1q deficient mice as compared to wild type mice both by electrophysiology measures and by behavioral studies.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

What is claimed is:

1. A method of treating a patient suffering from cognitive decline, the method comprising administering to the patient an antibody that binds to C1q, C1s, or C1r.

2. The method of claim 1, wherein the antibody binds to C1q.

3. The method of claim 1, wherein the antibody binds to C1s.

4. The method of claim 1, wherein the antibody binds to C1r.

5. The method of claim 1, wherein the cognitive decline is triggered or exacerbated by synapse loss.

6. The method of claim 1, wherein the cognitive decline is triggered or exacerbated by injury to the brain.

7. The method of claim 6, wherein the injury to the brain is sepsis, trauma, toxin, or ischemia.

8. The method of claim 1, wherein the cognitive decline is a dementia or memory loss.

9. The method of claim 1, wherein the cognitive decline is age-associated cognitive impairment.

10. The method of claim 1, wherein the cognitive decline is a worsening of mental functions over time.

11. The method of claim 10, wherein the worsening of mental functions is an inability to plan or follow instructions.

12. A method of inhibiting synapse loss in a patient suffering from cognitive decline, the method comprising administering to the patient an antibody that binds to C1q, C1s, or C1r.

13. The method of claim 12, wherein the antibody binds to C1q.

14. The method of claim 12, wherein the antibody binds to C1s.

15. The method of claim 12, wherein the antibody binds to C1r.

16. The method of claim 12, wherein the cognitive decline is triggered or exacerbated by injury to the brain.

17. The method of claim 16, wherein the injury to the brain is sepsis, trauma, toxin, or ischemia.

18. The method of claim 12, wherein the cognitive decline is a dementia or memory loss.

19. The method of claim 12, wherein the cognitive decline is age-associated cognitive impairment or mild cognitive impairment.

20. The method of claim 12, wherein the cognitive decline is a worsening of mental functions.

21. The method of claim 20, wherein the worsening of mental functions is an inability to plan or follow instructions.

* * * * *